(12) United States Patent
Kim et al.

(10) Patent No.: US 9,227,955 B2
(45) Date of Patent: Jan. 5, 2016

(54) COMPOUND HAVING ANGIOGENESIS INHIBITORY ACTIVITY, METHOD FOR PREPARING SAME, AND PHARMACEUTICAL COMPOSITION COMPRISING SAME

(75) Inventors: Ji Han Kim, Seoul (KR); Je Hak Kim, Gyeonggi-do (KR); Joon Kwang Lee, Gyeonggi-do (KR); Hahn-Sun Jung, Gyeonggi-do (KR); Nam Seok Han, Gyeonggi-do (KR); Yong Park, Gyeonggi-do (KR); Seung-Hoon Kang, Gyeonggi-do (KR); Hee Jin Jeong, Gyeonggi-do (KR); Kyung-Tae Lee, Seoul (KR); Hye Eun Choi, Seoul (KR); Yong Ha Chi, Gyeonggi-do (KR); Joo Han Lee, Seoul (KR); Soo Heui Paik, Gyeonggi-do (KR)

(73) Assignee: Boryung Pharmaceutical Co., Ltd., Seoul (KR)

( * ) Notice: Subject to any disclaimer, the term of this patent is extended or adjusted under 35 U.S.C. 154(b) by 0 days.

(21) Appl. No.: 14/235,439

(22) PCT Filed: Jul. 27, 2012

(86) PCT No.: PCT/KR2012/006037
§ 371 (c)(1),
(2), (4) Date: May 5, 2014

(87) PCT Pub. No.: WO2013/015657
PCT Pub. Date: Jan. 31, 2013

(65) Prior Publication Data
US 2014/0256711 A1 Sep. 11, 2014

(30) Foreign Application Priority Data
Jul. 27, 2011 (KR) .................. 10-2011-0074638

(51) Int. Cl.
| *C07D 213/02* | (2006.01) |
| *C07D 401/12* | (2006.01) |
| *C07D 401/14* | (2006.01) |
| *C07D 213/82* | (2006.01) |
| *C07D 495/04* | (2006.01) |
| *C07D 413/14* | (2006.01) |
| *C07D 417/14* | (2006.01) |

(52) U.S. Cl.
CPC ............ *C07D 401/14* (2013.01); *C07D 213/82* (2013.01); *C07D 401/12* (2013.01); *C07D 413/14* (2013.01); *C07D 417/14* (2013.01); *C07D 495/04* (2013.01)

(58) Field of Classification Search
CPC .......................... C07D 213/02; C07D 401/12
USPC ............... 514/212.08, 237.2, 253.13, 266.22, 514/301, 318, 323; 546/114, 194, 277.4; 544/130, 284, 365; 540/524
See application file for complete search history.

(56) References Cited

U.S. PATENT DOCUMENTS
3,912,736 A * 10/1975 Noda et al. .................. 544/279

FOREIGN PATENT DOCUMENTS
| JP | A-S50-82075 | 7/1975 |
| JP | A-2007-504210 | 3/2007 |
| WO | WO 02/068406 A2 | 9/2002 |
| WO | WO 2004/007458 A1 | 1/2004 |
| WO | WO 2005-021508 A1 | 3/2005 |
| WO | WO 2006/012374 A1 | 2/2006 |
| WO | WO 2009/000558 A1 | 12/2008 |

OTHER PUBLICATIONS

Creamer, D., et al., "Angiogenesis in psoriasis," *Angiogenisis* 5:231-236, Kluwer Academic Publishers, Netherlands (2003).
Folkman, J., "Angiogenesis in cancer, vascular, rheumatoid and other disease," *Nature Medicine* 1(1):27-30, Nature Publishing Company, United States (1995).
Ingber, D., et al., "Synthetic analogues of fumagillin that inhibit angiogenesis and suppress tumour growth," *Letters to Nature* 348:555-557, Macmillan Magazines Ltd., England (1990).
Kräling, B.M., et al., "E-Selectin is present in Proliferating Endothelial Cells in Human Hemangiomas," *American Journal of Pathology* 148(4):1181-1191, American Society for Investigative Pathology, United States (1996).
Kwon, Y.S., et al., "Inhibitory Effect of Rapamycin on Corneal Neovascularization In Vitro and In Vivo," *Investigative Ophthalmology & Visual Science* 46(2):454-460, Association for Research in Vision and Ophthalmology, United States (2005).
Miyanaga, S., et al., "Anti-invasive and anti-angiogenic activities of naturally occurring dibenzodiazepine BU-4664L and its derivatives," *Bioorganic & Medicinal Chemistry Letters* 20:963-965, Elsevier Ltd., England (Feb. 2010).
O'Reilly, M.S., et al., "Angiostatin: A Novel Angiogenesis Inhibitor That Mediates the Suppression of Metastases by a Lewis Lung Carcinoma," *Cell* 79:315-328, Cell Press, England (1994).
O'Reilly, M.S., et al., "Endostatin: An Endogenous Inhibitor of Angiogenesis and Tumor Growth," *Cell* 88:277-285, Cell Press, England (1997).
Sherwood, L.M. and Parris, E.E., "Tumor Angiogenesis: Therapeutic Implications," *The New England Journal of Medicine* 285(21):1182-1186, Massachusetts Medical Society, United States (1971).
Woodhouse, E.C., et al., "General Mechanisms of Metastasis," *Cancer Supplement* 80(8):1529-1537, American Cancer Society, United States (1997).
Kwak, NH, "Angiogenesis of Retina in Diabetic Retinopathy," *Journal of the Korean Endocrine Society*, 16(3): 339-351, Korean Endocrine Society, Korea (2001).
Kwon, HJ. Low Molecular Weight Chemicals for the Regulation of Angiogenesis. *Journal of the Korean Endocrine Society*, 16(3):352-365, Korean Endocrine Society (2001).

* cited by examiner

*Primary Examiner* — Niloofar Rahmani
(74) *Attorney, Agent, or Firm* — Sterne, Kessler, Goldstein & Fox PLLC

(57) ABSTRACT

Disclosed are an anti-angiogenic compound, represented by Chemical Formula I, or a pharmaceutically acceptable salt thereof, a preparation method thereof, and a pharmaceutically acceptable composition including the same. Because the compound of Chemical Formula I potently suppresses the angiogenesis, the compound of Chemical Formula I is applicable to the prevention and treatment of diseases caused by aberrant activity of vascular endothelial growth factor, and available as an anti-angiogenic agent.

17 Claims, 5 Drawing Sheets

COMPOUND HAVING ANGIOGENESIS INHIBITORY ACTIVITY, METHOD FOR PREPARING SAME, AND PHARMACEUTICAL COMPOSITION COMPRISING SAME

TECHNICAL FIELD

The present invention relates to a novel compound having inhibitory activity against angiogenesis, a method for preparing the same, and a pharmaceutical composition comprising the same.

The present invention relates to a pharmaceutical composition for the prevention or treatment of a disease or symptom caused by aberrant activity of VEGF (vascular endothelial growth factor).

BACKGROUND ART

In spite of extensive worldwide studies conducted on cancer, it is in practice difficult to cure cancer because of the diversity of cancer itself and the variable pathogenic mechanisms of cancer. There have been incessant attempts made to develop new anti-cancer agents that can overcome the problem with chemoresistance without causing side effects. However, pertinent, efficient drugs still remain in need of development.

The growth of a tumor is incapacitated without the formation of new vessels which supports the growth. As a tumor grows, it rapidly outgrows its blood supply, becoming oxygen insufficient therein. This tumor hypoxia leads to tumor necrosis. In addition, tumor vasculature is destroyed by the pressure of the tumor itself, aggravating the hypoxia. To detour the problem therewith, a tumor expresses proteins necessary for the formation of new vessels to encourage angiogenesis therefore.

So far, much research into the formation of new vessels has resulted in the appearance of various factors involved in angiogenesis or neovascularization, including angiogenic factors, such as VEGF (vascular endothelial growth factor), bFGF (basic fibroblast growth factor), HGF (hepatocyte growth factor), EGF (epithelial growth factor), and angiopoietin, angiogenic factor receptors with tyrosine kinase activity, such as FGFR (fibroblast growth factor receptor), Flk-1/KDR, Flt-1, Flt-3, Tie-1, Tie-2/Tek, and Eph, and endogenous angiogenesis inhibitors, such as angiostatin and endostatin, giving an insight into relationship between angiogenesis or neovascularization and human diseases as well as the mechanism of angiogenesis and neovascularization, and suggesting various methods for regulating angiogenesis. Inter alia, VEGF has aroused a great interest as a target for the selective inhibition of angiogenesis because it is found to have a close correlation with cancer progression and cure rate and its receptor Flk-1/KDR is expressed on endothelial cells with high specificity.

With regard to the relationship between cancer and vessel formation, it was first hypothesized in 1971 by Dr. Folkman that angiogenesis would play an essential role in tumor growth (J. Folkman, Tumor Angiogenesis: Therapeutic Implications. New England Journal of Medicine, 285, 1182-1186, 1971). Since the report on the selective inhibitory effect of fumagillin, a complex biomolecule from a microbial organism, on angiogenesis in 1990, keen attention has been paid to anti-angiogenic agents as therapeutics for cancer (D. Ingber, T. Fujita, et al. Synthetic analogues of fumagillin that inhibit angiogenesis and suppress tumor growth. Nature, 348, 555-557, 1990). In addition, endogenous angiogenesis inhibitors, such as angiostatin (M. S. O'Reilly, L. Holmgren, Y. Shing, C. Chen, R. A. Rosenthal, M. Moses, W. S. Lane, Y. Cao, E. H. Sago and J. Forkman., Angiostatin: a novel angiogenesis inhibitor that mediates the suppression of metastases by a Lewis Lung Carcinoma, Cell, 79, 315-328, 1994), and endostatin (M. S. O'Reilly, T. Boehm, C. Chen, et al., Endostatin: an endogenous inhibitor of angiogenesis and tumor growth. Cell, 88, 277-285, 1997) have recently been verified to have potent anticancer activity in animal models, attracting great attention to the use thereof as anticancer agents.

Moreover, angiogenesis inhibitors have advantages as anti-cancer agents over other anticancer agents in the following aspects: because angiogenesis is essential for the growth and metastasis of cancer, an angiogenesis inhibitor can block cancer growth and metastasis, simultaneously; and an angiogenesis inhibitor targets normal diploid vascular endothelial cells rather than aneuploid, cancer cells, entailing no problems with resistance attributed to the heterogeneity and genetic instability of cancer cells; an angiogenesis inhibitor can exert inhibitory activity against any kind of cancers for the growth of which angiogenesis is indispensible while other anticancer agents show a narrow therapeutic spectrum of specific or several cancers; and since angiogenesis is rare in adults, except for several cases, such as wound healing, menstruation, etc., side effects incurred by other anticancer agents would be greatly reduced upon the use of an angiogenesis inhibitor.

In addition to involvement in the growth and metastasis of cancer, angiogenesis is a direct cause of various angiogenic diseases, including rheumatoid arthritis (Kwon, Ho-Jung, Journal of the Korean Endocrine Society, Vol 16, No. 3, 2001), diabetic retinopathy (Kwoak, No-Hoon, Journal of the Korean Endocrine Society, Vol. 16, No. 3, 2001), ophthalmic diseases such as keratitis, hyperemia, macular degeneration, choroidal neovascularization, and neovascular glaucoma (Y S Kwon, H S Hong, J C Kim, J S Shin, Y S Son. Invest. Ophthalmol. Vis. Sci. February 2005 vol. 46 no. 2 454-460), and corneal neovascularization (Kim, J. H., Lee J. Y., Chung S. K., and Joo C. K. Journal of the Korean Ophthalmological Society, Vol. 40, No. 3, 662-666), psoriasis (D. Creamer, D. Sullivan, R. Bicknell and J. Barker. Angiogenesis Volume 5, Number 4, 231-236), hemangiomas, which may cause the blockage of the airway in lung, threatening life (Birgit M. Kraling et al. American Journal of Pathology, Vol. 148, No. 4, April 1996), and obesity, and thus is expected to be usefully applicable to the prevention and treatment of diseases associated with vascular proliferation as well as cancer.

PRIOR ART DOCUMENT

Non-Patent Document (Non-patent document 1) 1. Angiogenesis in cancer, vascular, rheumatoid and other disease. Folkman J. Nat Med. 1995 1(1) 27-31. Review.
(Non-patent document 2) 2. General mechanisms of metastasis. Woodhouse E. C., Chuaqui R. F., Liotta L. A. Cancer. 1997, Vol 80 (8 Suppl) 1529-1537. Review.
(Non-patent document 3) 3. Anti-invasive and anti-angiogenic activities of naturally occurring dibenzodiazepine BU-4664L and its derivatives. Miyanaga S., Sakurai H., Saiki I., Onaka H., Igarashi Y. Bioorg. Med. Chem. Lett. 2010 20 (3) 963-965.
(Non-patent document 4) 4. Tumor Angiogenesis: Therapeutic Implications. J. Folkman. New England Journal of Medicine, 285, 1182-1186, 1971.

(Non-patent document 5) 5. Synthetic analogues of fumagillin that inhibit angiogenesis and suppress tumor growth. D. Ingber, T. Fujita, et al. Nature, 348, 555-557, 1990.

(Non-patent document 6) 6. Angiostatin: a novel angiogenesis inhibitor that mediates the suppression of metastases by a Lewis Lung Carcinoma. M. S. O'Reilly, L. Holmgren, Y. Shing, C. Chen, R. A. Rosenthal, M. Moses, W. S. Lane, Y. Cao, E. H. Sago and J. Forkman. Cell, 79, 315-328, 1994.

(Non-patent document 7) 7. Endostatin: an endogenous inhibitor of angiogenesis and tumor growth. M. S. O'Reilly, T. Boehm, C. Chen, et al. Cell, 88, 277-285, 1997.

(Non-patent document 8) 8. Angiogenesis Regulation Low-Molecular Compounds. Journal of the Korean Endocrine Society, Vol. 16, No. 3, 2001.

(Non-patent document 9) 9. Study on Neovascularization in Diabetic Retinopathy. Journal of the Korean Endocrine Society, Kwoak, No-Hoon, Vol. 6, No. 3, 2001.

(Non-patent document 10) 10. Inhibitory Effect of Rapamycin on Corneal Neovascularization In Vitro and In Vivo. Y S Kwon, H S Hong, J C Kim, J S Shin, Y S Son. Invest. Ophthalmol. Vis. Sci. February 2005 vol. 46 no. 2 454-460.

(Non-patent document 11) 11. Angiogenesis in psoriasis. D. Creamer, D. Sullivan, R. Bicknell and J. Barker. Angiogenesis Volume 5, Number 4, 2002, pp. 231-236(6).

(Non-patent document 12) 12. E-Selectin Is Present in Proliferating Endothelial Cells in Human Hemangiomas. Birgit M. Kraling et al. American Journal of Pathology, Vol. 148, No. 4, April 1996.

DISCLOSURE

Technical Problem

It is an object of the present invention to provide a novel compound with anti-angiogenic activity, a method for preparing the same, and a pharmaceutical composition comprising the same.

Technical Solution

In accordance with an aspect thereof, the present invention addresses a compound represented by the following Chemical Formula I, or a pharmaceutically acceptable salt thereof:

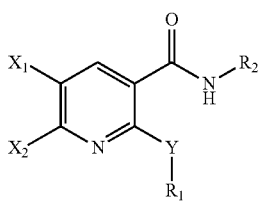

[Chemical Formula I]

wherein, $X_1$ and $X_2$ are each independently a halogen atom (F, Cl, Br, I) or a hydrogen atom, Y is —NH—; —S—; or —O—, $R_1$ is piperidinyl, piperazinyl, azabicyclo[2.2.2]octanyl, or phenyl, each being independently substituted with 1 to 5 substituents selected from the group consisting of benzyl, phenyloxy, 1,1-pyrimidinethyl, pyridine methyl, $C_{1-4}$ alkyl, $C_{3-6}$ alkene, and t-butoxycarboxyl and malon-2-yl, wherein the $C_{1-4}$ alkyl is substituted with 0 to 3 substituents selected from the group consisting of $R_3R_4N$—, hydroxyl, and a halogen atom, wherein $R_3$ and $R_4$ are each independently a $C_{1-4}$ alkyl, wherein the benzyl, the phenyloxy, the pyrimidinemethyl and the pyrimidinemethyl are each independently substituted with 0 to 4 halogen atoms, $R_2$ is a $C_{1-4}$ alkyl with 1 or 2 substituents selected from among morpholinyl substituted with 0 to 3 benzyl groups having 0 to 3 halogen substituents, phenyl substituted with 0 to 3 halogen atoms, pyridinyl, pyrimidinyl, and piperazinyl; $C_{5-10}$ alkyl; $C_{1-4}$ alkyloxycarbonylamino; $C_{1-4}$alkoxy$C_{1-4}$ alkyl; toluenesulfonamino; phenyl with 0 to 3 substituents selected from among $C_{1-4}$ alkyl, halogen, nitro and phenoxy; pyridinyl with 0 to 3 substituents selected from among C1-4 alkyloxycarbonyl and $C_{1-4}$ alkyl; azepan-2-onyl; 1,3,4-triazolyl; pyrimidinyl substituted with 0 to 3 $C_{1-4}$ alkyl groups; pyrrolidinyl; thiazolyl substituted with 0 to 2 $C_{1-4}$ alkyl groups; 2,3-dihydroxy indole substituted with 0 to 3 $C_{1-4}$ alkyl groups;

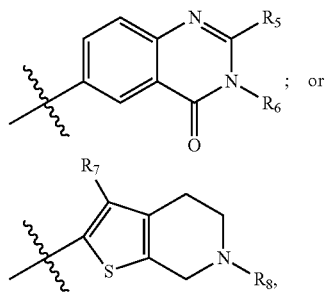

wherein $R_5$ and $R_6$ are each independently $C_{1-4}$alkyl, $C_{1-4}$alkyl sulfanyl or thiol, and $R_7$ and $R_8$ are each independently $C_{1-4}$ alkyloxycarbonyl, phenyl or benzyl.

In one preferred embodiment, $R_1$ is 1-benzylpiperidin-4-yl; 1-benzylpiperidin-3-yl; 4-phenoxyphenyl; 1-(2-hydroxyethyl)-piperidin-4-yl; 1-(2-hydroxyethyl)-piperidin-3-yl; 1-(2-hydroxyethyl)-piperazin-4-yl; 2,2,6,6-tetramethylpiperidin-4-yl; t-butoxycarbonylpiperidin-4-yl; t-butoxycarbonylpiperidin-3-yl; 1-azabicyclo[2.2.2]oct-3-yl; methylpiperidin-4-yl; methylpiperazin-4-yl; piperidin-4-yl; piperidin-3-yl; 1-(2-hydroxyethyl)-2,2,6,6-tetramethylpiperidin-4-yl; 1-arylpiperidin-4-yl(1-allylic piperidine-4-yl); [2-(N,N-dimethylamino)ethyl]piperidin-4-yl; (t-butyloxycarbonyl)piperidin-3-yl: (malon-2-yl)piperidin-4-yl; (pyridin-2-yl)methylpiperidin-4-yl; (pyridin-3-yl)methylpiperidin-4-yl; or 1-(6-chloro-5-fluoropyrimidin-4-yl)ethyl piperidin-4-yl. More preferably, $R_1$ is 1-benzylpiperidin-4-yl; 1-benzylpiperidin-3-yl; 1-(2-hydroxyethyl)-piperidin-4-yl; piperidin-3-yl; or t-butoxycarbonylpiperidin-3-yl.

In one preferred embodiment, $R_2$ is 3-chlorophenyl; 4-phenoxyphenyl; 3,3-dimethyl-2,3-dihydro-1H-indol-6-yl; 4-(4-fluorobenzyl)-morpholin-2-ylmethyl; 1,3,4-triazol-2-yl; 4,6-dimethylpyrimidin-2-yl; (S)-pyrrolidin-3-yl; 2-(morpholin-1-yl)ethyl; t-butoxycarbonylamino; (3-methoxycarbonyl) pyridin-6-yl; p-toluenesulfonamino; pyridin-4-ylmethyl; 1,2-diphenylethyl; 2-methoxyethyl; 5-methylthiazol-2-yl; 3-methylpyridin-2-yl; azepan-2-on-3-yl; 4-fluorobenzyl; 2-ethylhexyl; 3-methyl-2-methylsulfanyl-3,4-dihydro-quinazolin-4-on-6-yl; (3,4-dimethoxy)phenyl;

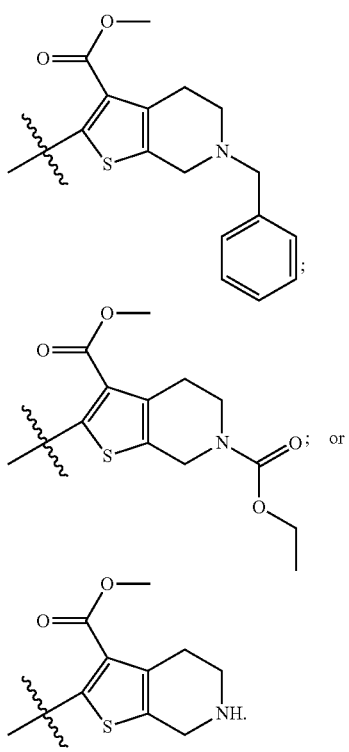

More preferably, $R_2$ is 3-chlorophenyl; 4-phenoxyphenyl; 5-methylthiazol-2-yl; or

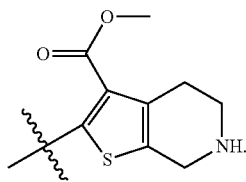 [SMILES: *c1sc2c(c1C(=O)OC)CCNC2]

Unless otherwise stated, "compounds of Chemical Formula I" include all racemates thereof, optical isomers thereof, and solvates (hydrates) thereof, whether crystalline or amorphous.

Representative, concrete examples of the compounds of Chemical Formula I or pharmaceutically acceptable salts thereof include:

2-(1-benzylpiperidin-4-ylamino)-N-(3-chlorophenyl)nicotinamide [103],
N-(3-chlorophenyl)-2-(4-phenoxyanilino)nicotinamide [104],
2-(1-benzylpiperidin-4-ylamino)-N-(4-phenoxyphenyl)nicotinamide [110],
2-(4-phenoxyanilino)-N-(4-phenoxyphenyl)nicotinamide [111],
N-(3-chlorophenyl)-2-(2,2,6,6-tetramethylpiperidin-4-ylamino)nicotinamide [201],
N-(3-chlorophenyl)-2-(1-tert-butoxycarbamoylpiperidin-4-ylamino)nicotinamide [208],
2-(1-azabicyclo[2.2.2]oct-3-ylamino)-N-(3-chlorophenyl)nicotinamide [210],
N-(3-chlorophenyl)-2-(1-methylpiperidin-4-ylamino)nicotinamide [214],
N-(3-chlorophenyl)-2-[1-(2-hydroxyethyl)piperidin-4-ylamino]nicotinamide [218],
N-(3-chlorophenyl)-2-(4-methylpiperazin-1-ylamino)nicotinamide [240],
N-(3-chlorophenyl)-2-[4-(2-hydroxyethyl)piperazin-1-ylamino)nicotinamide [241],
(R)-2-(1-benzylpiperidin-3-ylamino)-N-(3-chlorophenyl)nicotinamide [267]
(S)-2-(1-benzylpiperidin-3-ylamino)-N-(3-chlorophenyl)nicotinamide [273],
(R)—N-(3-chlorophenyl)-2-(1-tert-butoxycarbamoylpiperidin-3-ylamino)nicotinamide [270],
(S)—N-(3-chlorophenyl)-2-(1-tert-butoxycarbamoylpiperidin-3-ylamino)nicotinamide [276],
2-(1-benzylpiperidin-4-ylamino)-6-chloro-N-(3-chlorophenyl)nicotinamide [301],
2-(1-benzylpiperidin-4-ylamino)-6-chloro-N-(3-chlorophenyl)-5-fluoronicotinamide [302],
6-chloro-N-(3-chlorophenyl)-2-[1-(2-hydroxyethyl)benzylpiperidin-4-ylamino]nicotinamide [311],
6-chloro-N-(3-chlorophenyl)-5-fluoro-2-[1-(2-hydroxyethyl)piperidin-4-ylamino]nicotinamide [312],
2-(1-benzylpiperidin-4-ylamino)-N-(3,3-dimethyl-2,3-dihydro-1H-indol-6-yl)nicotinamide [117],
N-(3,3-dimethyl-2,3-dihydro-1H-indol-6-yl)-2-(4-phenoxyanilino)nicotinamide [118],
N-(3-chlorophenyl)-2-(4-piperidylamino)nicotinamide [224],
(R)—N-(3-chlorophenyl)-2-(3-piperidylamino)nicotinamide [269],
(S)—N-(3-chlorophenyl)-2-(3-piperidylamino)nicotinamide [275],
N-(3-chlorophenyl)-2-(1-(2-hydroxyethyl)-2,2,6,6-tetramethylpiperidin-4-ylamino)nicotinamide [242],
2-(1-arylpiperidin-4-ylamino)-N-(3-chlorophenyl)nicotinamide [243],
N-(3-chlorophenyl)-2-[1-(2-N,N-diethylamino-ethyl)piperidin-4-ylamino]nicotinamide [244],
N-(3-chlorophenyl)-2-[1-(pyridin-2-ylmethyl)piperidin-4-ylamino]nicotinamide [248],
N-(3-chlorophenyl)-2-[1-(pyridin-3-ylmethyl)piperidin-4-ylamino]nicotinamide [249],
2-{1-[1-(6-chloro-5-fluoropyrimidin-2-yl)ethyl]piperidin-4-ylamino}-N-(3-chlorophenyl)nicotinamide [250],
(R)—N-(3-chlorophenyl)-2-[1-(2-hydroxyethyl)piperidin-3-ylamino]nicotinamide [268],
(S)—N-(3-chlorophenyl)-2-[1-(2-hydroxyethyl)piperidin-3-ylamino]nicotinamide [274],
2-{4-[3-(3-chlorophenylcarbamoyl)pyridin-2-ylamino]piperidin-1-yl}malonic acid [246],
2-(1-benzylpiperidin-4-yloxy)-N-(3-chlorophenyl)nicotinamide [289],
2-(1-benzylpiperidin-4-ylsulfanyl)-N-(3-chlorophenyl)nicotinamide [290],
2-(1-benzylpiperidin-4-ylamino)-N-[4-(4-fluorobenzyl)morpholin-2-ylmethyl]nicotinamide [404],
2-(1-benzylpiperidin-4-ylamino)-N-(1,3,4-triazol-2-yl)nicotinamide [406],
2-(1-benzylpiperidin-4-ylamino)-N-(4,6-dimethylpyrimidin-2-yl)nicotinamide [407],
2-(1-benzylpiperidin-4-ylamino)-N—(S)-pyrrolidin-3-ylnicotinamide [408],
2-(1-benzylpiperidin-4-ylamino)-N-2-(morpholin-1-yl)ethylnicotinamide [409],
N'-[2-(1-benzylpiperidin-4-ylamino)pyridine-3-carbonyl]hydrazine carboxylic acid tert-butyl ester [410],
Methyl 6-{[2-(1-benzylpiperidin-4-ylamino)pyridine-3-carbonyl]amino}nicotinate [412], 2-(1-benzylpiperidin-4-ylamino)-N-(para-toluene-sulfonamino)nicotinamide [424],
2-(1-benzylpiperidin-4-ylamino)-N-(pyridin-4-ylmethyl)nicotinamide [425],
2-(1-benzylpiperidin-4-ylamino)-N-(1,2-diphenylethyl)nicotinamide [426],
2-(1-benzylpiperidin-4-ylamino)-N-(2-methoxyethyl)nicotinamide [427],
2-(1-benzylpiperidin-4-ylamino)-N-(5-methylthiazol-2-yl)nicotinamide [428],
2-(1-benzylpiperidin-4-ylamino)-N-(3-methylpyridin-2-yl)nicotinamide [429],
2-(1-benzylpiperidin-4-ylamino)-N-(azepan-2-on-3-yl)nicotinamide [430],
2-(1-benzylpiperidin-4-ylamino)-N-(4-fluorobenzyl)nicotinamide [431],
2-(1-benzylpiperidin-4-ylamino)-N-(2-ethylhexyl)nicotinamide [436],
2-(1-benzylpiperidin-4-ylamino)-N-(3-methyl-2-methylsulfanyl-3,4-dihydroquinazolin-4-on-6-yl)nicotinamide [439],
6-benzyl-2-{[2-(1-benzylpiperidin-4-ylamino)pyridine-3-carbonyl]amino}-4,5,6,7-tetrahydro-thieno[2,3-c]pyridine-3-carboxylic acid methyl ester [440],
6-ethoxycarbamaate-2-{[2-(1-benzylpiperidin-4-ylamino)pyridine-3-carbonyl]amino}-4,5,6,7-tetrahydro-thieno[2,3-c]pyridine-3-carboxylic acid methyl ester [441],
2-{[2-(1-benzylpiperidin-4-ylamino)pyridine-3-carbonyl]amino}-4,5,6,7-tetrahydro-thieno[2,3-c]pyridine-3-carboxylic acid methyl ester [442],
2-(1-benzyl piperidin-4-ylamino)-N-(3,4-dimethoxyphenyl)nicotinamide [443],
2-{[2-(1-benzylpiperidin-4-ylamino)-6-chloropyridine-3-carbonyl]amino}-4,5,6,7-tetrahydrothieno[2,3-c]pyridine-3-carboxylic acid methyl ester [501],
2-{[2-(1-benzylpiperidin-4-ylamino)-6-chloropyridine-3-carbonyl]amino}-4,5,6,7-tetrahydrothieno[2,3-c]pyridine-3-carboxylic acid methyl ester [502],
2-{[2-(1-(2-hydroxyethyl)piperidin-4-ylamino)pyridine-3-carbonyl]amino}-4,5,6,7-tetrahydrothieno[2,3-c]pyridine-3-carboxylic acid methyl ester [503],
2-{[6-chloro-2-(1-(2-hydroxyethyl)piperidin-4-ylamino)pyridine-3-carbonyl]amino}-4,5,6,7-tetrahydrothieno[2,3-c]pyridine-3-carboxylic acid methyl ester [504],
2-{[6-chloro-5-fluoro-2-(1-(2-hydroxyethyl)piperidin-4-ylamino)pyridine-3-carbonyl]amino}-4,5,6,7-tetrahydrothieno[2,3-c]pyridine-3-carboxylic acid methyl ester [505],
2-{[2-(2,2,6,6-tetramethylpiperidin-4-ylamino)pyridine-3-carbonyl]amino}-4,5,6,7-tetrahydrothieno[2,3-c]pyridine-3-carboxylic acid methyl ester [506],
2-{[2-(2,2,6,6-tetramethylpiperidin-4-ylamino)6-chloropyridine-3-carbonyl]amino}-4,5,6,7-tetrahydrothieno[2,3-c]pyridine-3-carboxylic acid methyl ester [507],
2-{[6-chloro-5-fluoro-2-(2,2,6,6-tetramethylpiperidin-4-ylamino)pyridine-3-carbonyl]amino}-4,5,6,7-tetrahydrothieno[2,3-c]pyridine-3-carboxylic acid methyl ester [508],
2-{[2-(1-benzylpiperidin-3-ylamino)pyridine-3-carbonyl]amino}-4,5,6,7-tetrahydrothieno[2,3-c]pyridine-3-carboxylic acid methyl ester [509],
2-{[2-(1-benzylpiperidin-3-ylamino)-6-chloropyridine-3-carbonyl]amino}-4,5,6,7-tetrahydrothieno[2,3-c]pyridine-3-carboxylic acid methyl ester [510],
2-{[2-(1-benzylpiperidin-3-ylamino)-6-chloro-5-fluoropyridine-3-carbonyl]amino}-4,5,6,7-tetrahydrothieno[2,3-c]pyridine-3-carboxylic acid methyl ester [511],
6-chloro-N-(2-ethylhexyl)-2-[1-(2-hydroxyethyl)piperidin-4-ylamino]nicotinamide [515],
N-(2-ethylhexyl)-2-(2,2,6,6-tetramethylpiperidin-4-ylamino)nicotinamide [517],
6-chloro-N-(2-ethylhexyl)-5-fluoro-2-(2,2,6,6-tetramethylpiperidin-4-ylamino)nicotinamide [519],
2-(1-benzylpiperidin-3-ylamino)-N-(2-ethylhexyl)nicotinamide [520],
2-(1-benzylpiperidin-3-ylamino)-6-chloro-N-(2-ethylhexyl)-5-fluoronicotinamide [522], and pharmaceutically acceptable salts thereof.

The representative compounds of Chemical Formula I have the following structural formulas:

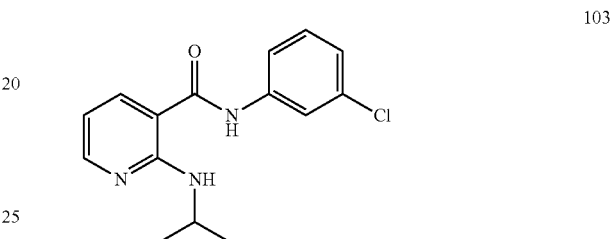

103

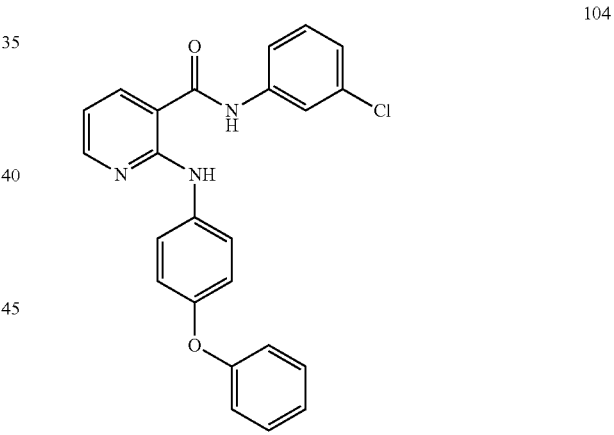

104

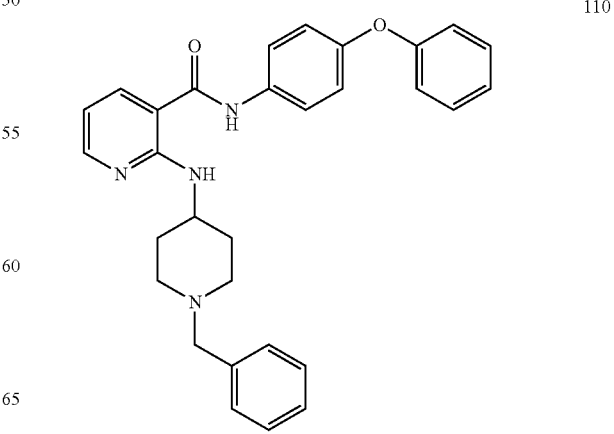

110

111 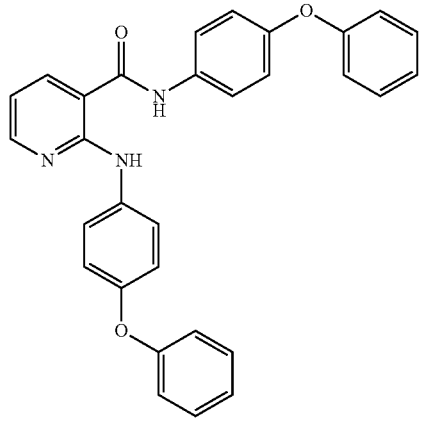
117 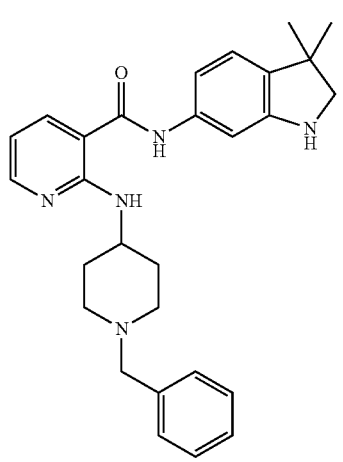
118 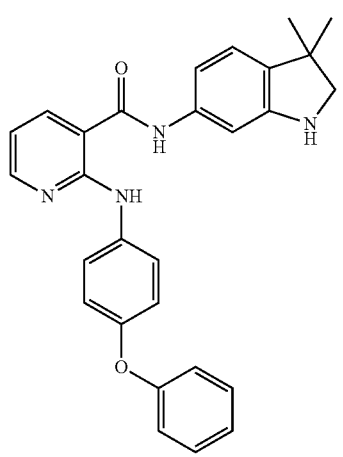
201 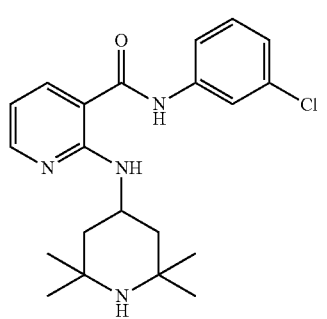
208 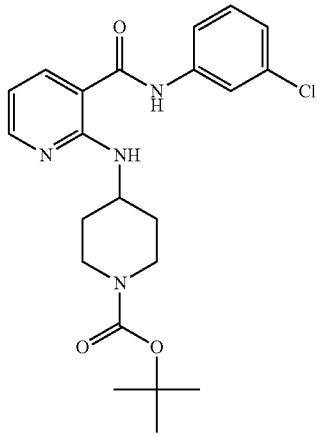
210 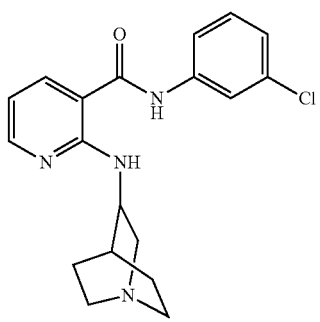
214 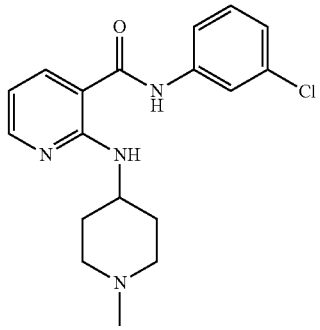
218 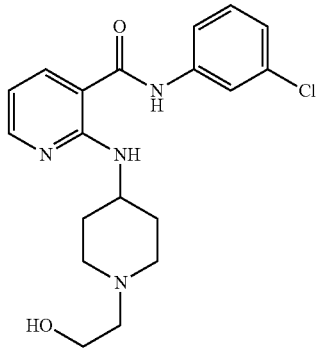

| | |
|---|---|
| 224 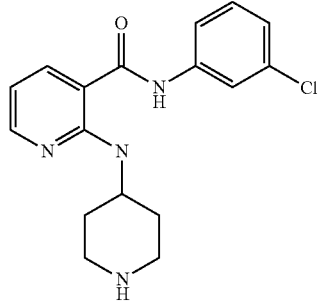 | 243 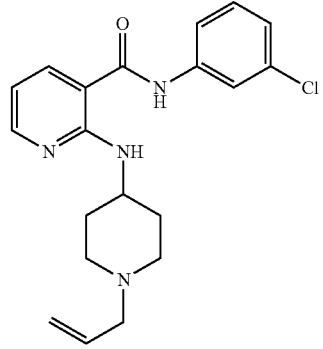 |
| 240 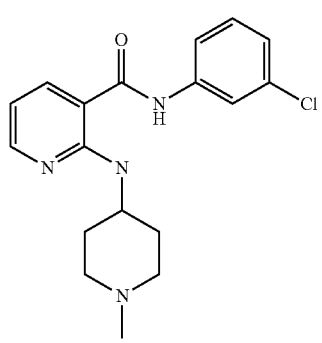 | 244 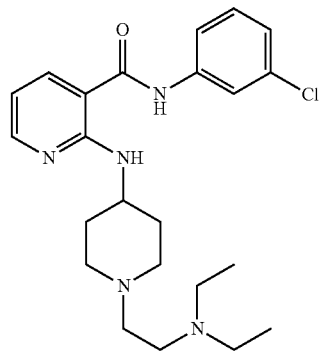 |
| 241 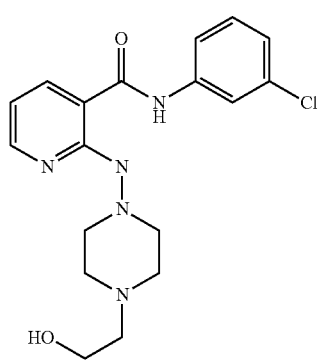 | 246 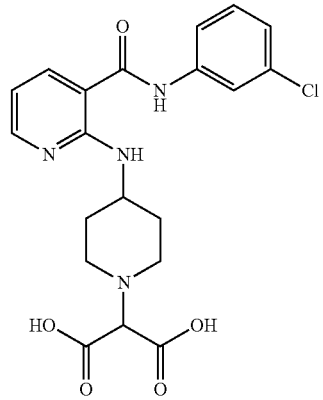 |
| 242 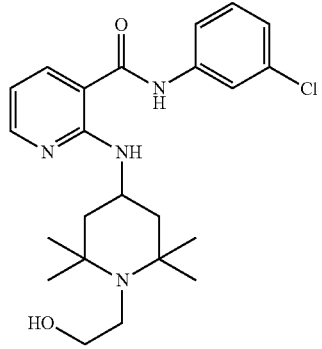 | 248 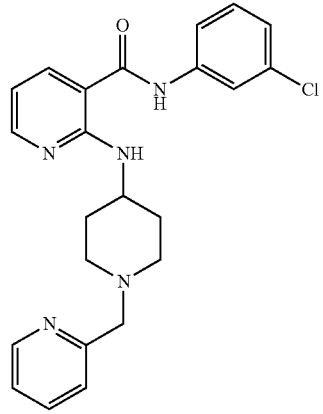 |

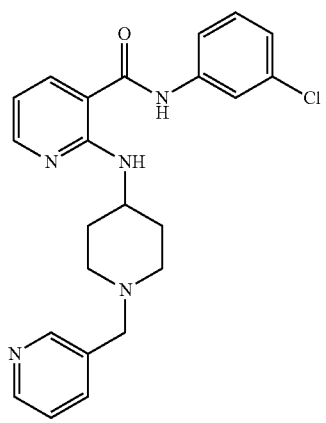
249
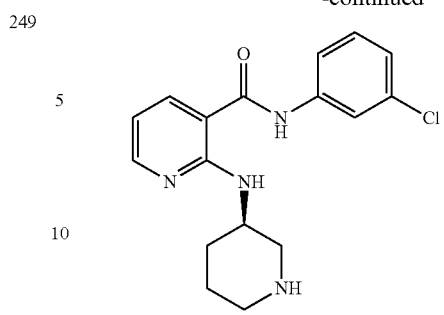
269
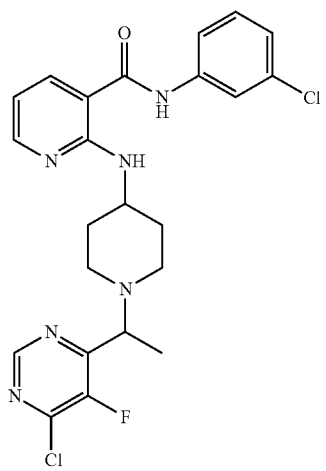
250
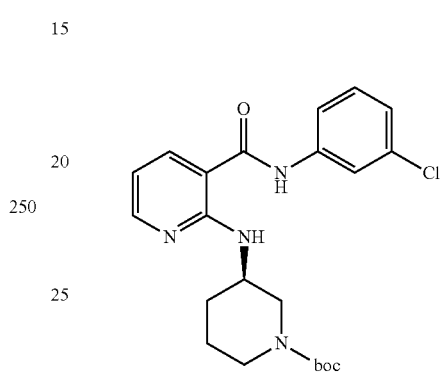
270
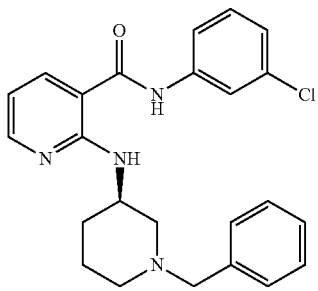
267
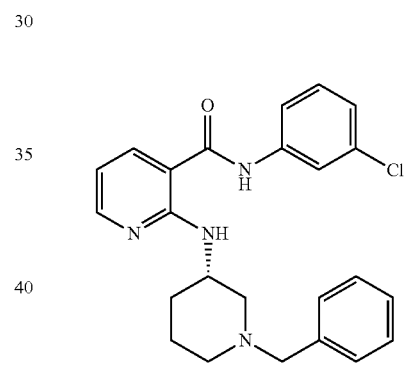
273
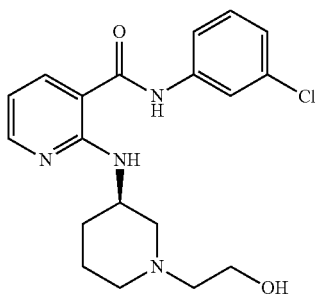
268
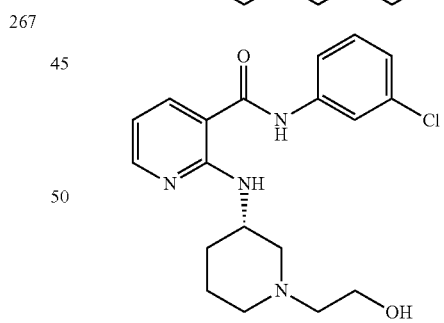
274
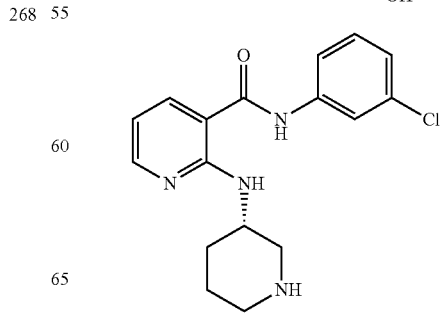
275

276 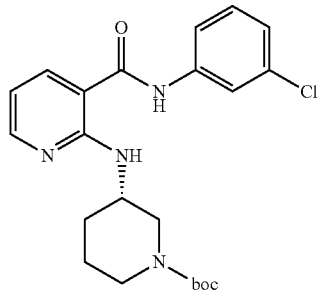
289 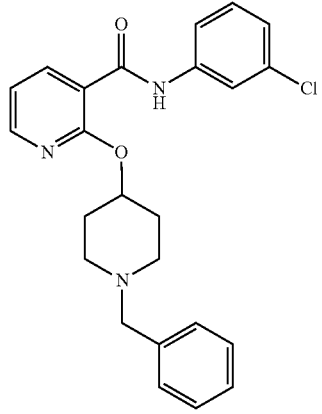
290 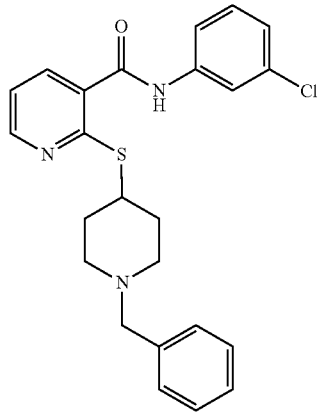
301 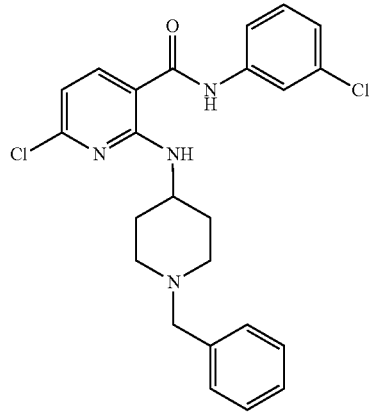
302 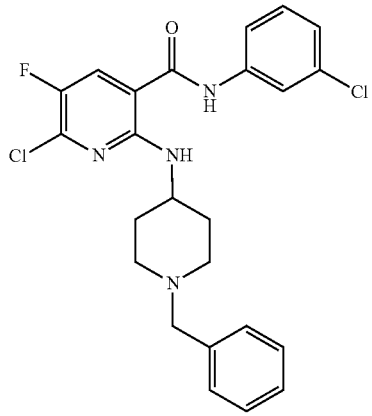
311 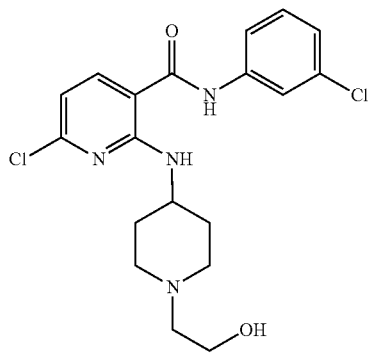
312 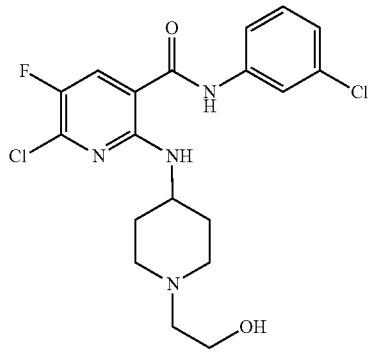
404 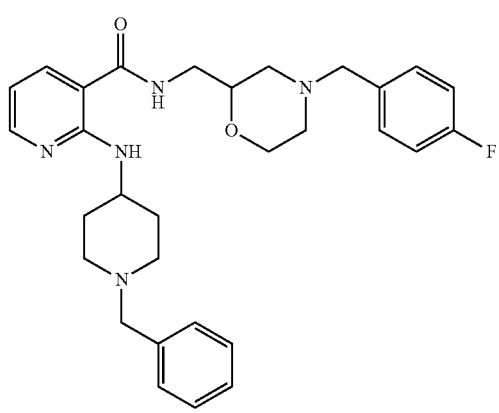

406 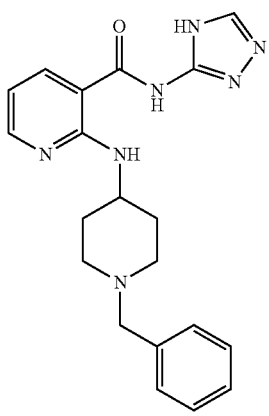
407 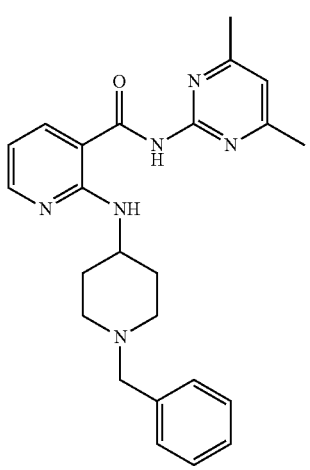
408 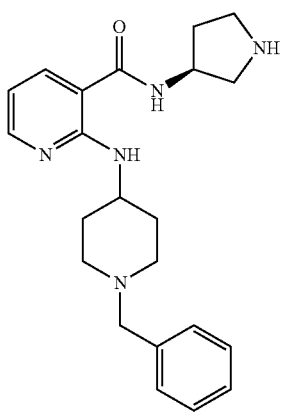
409 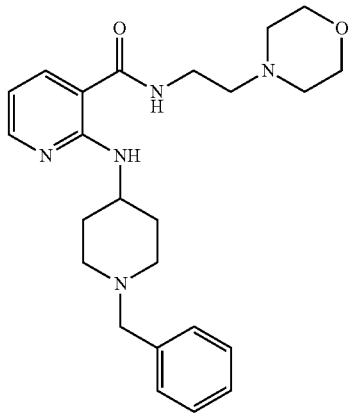
410 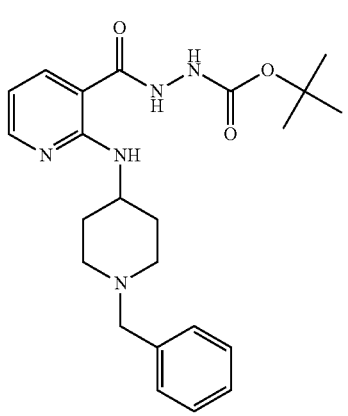
412 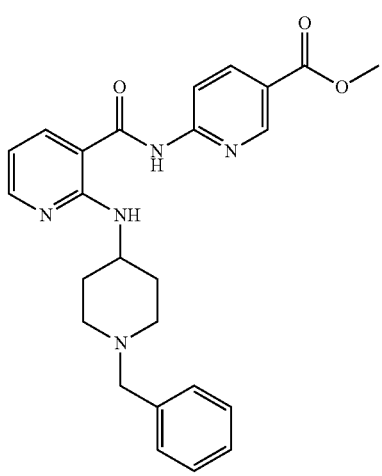

424
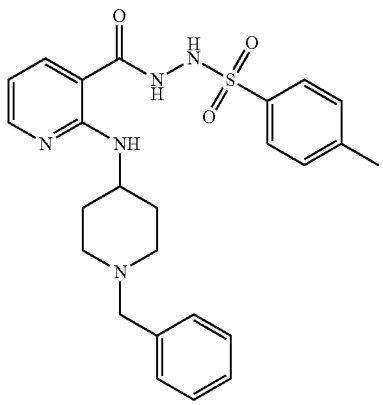
425
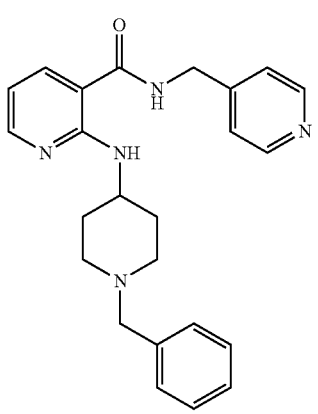
426
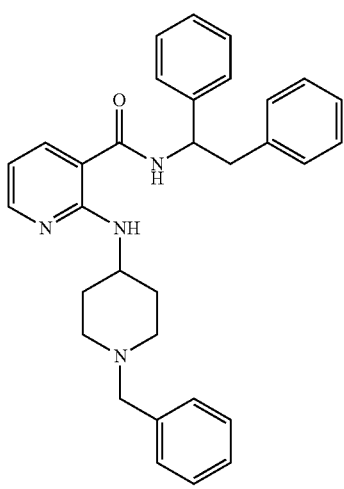
427
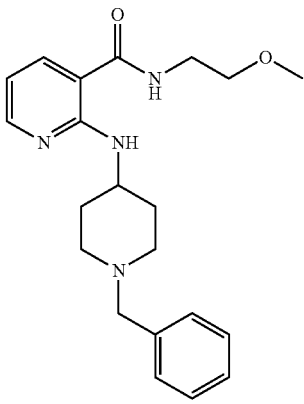
428
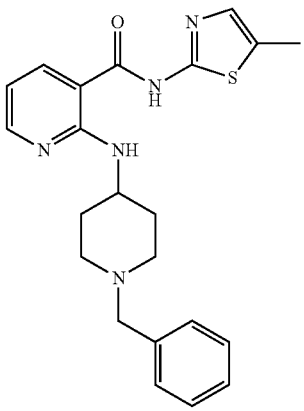
429
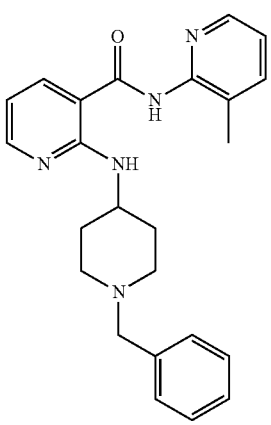
430
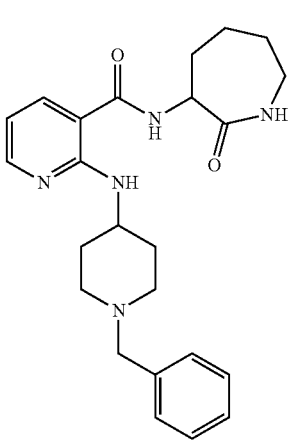

431
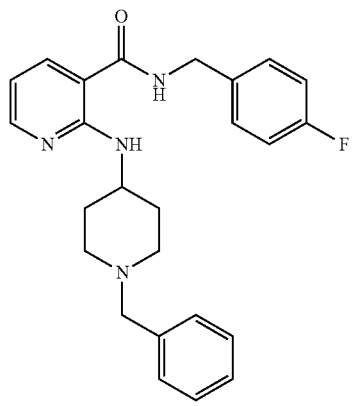
436
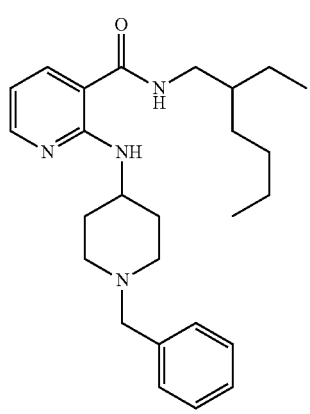
439
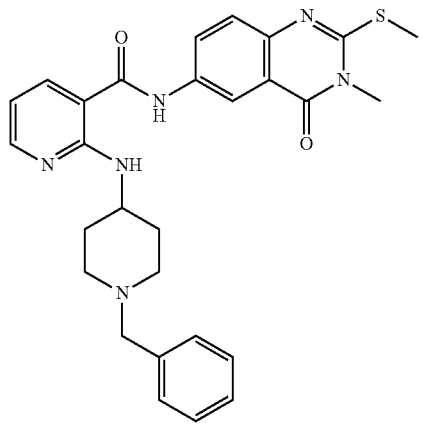
440
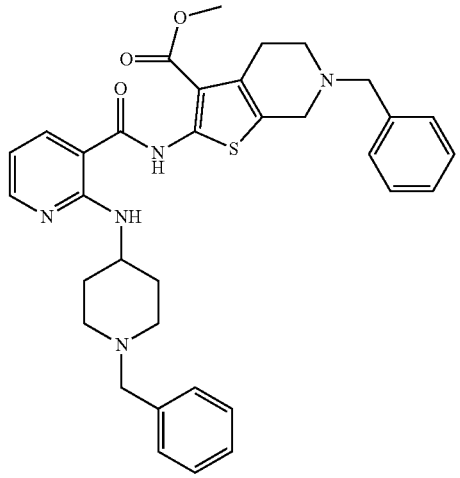
441
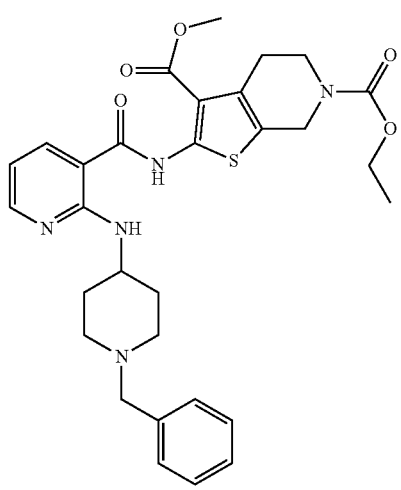
442
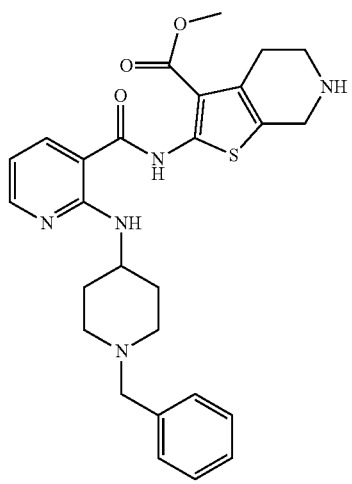

443
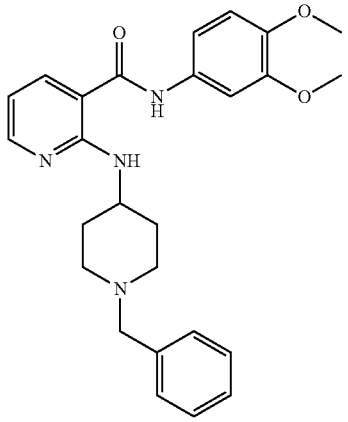
501
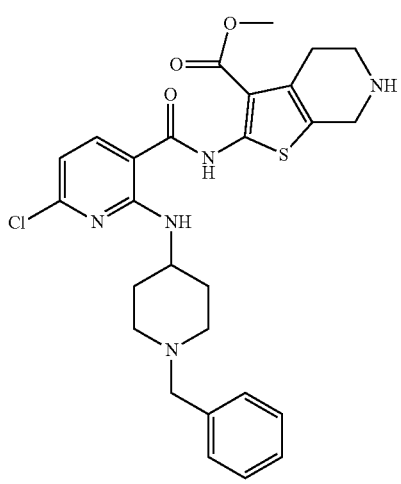
502
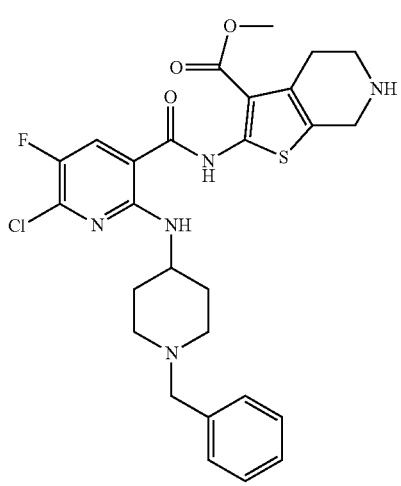
503
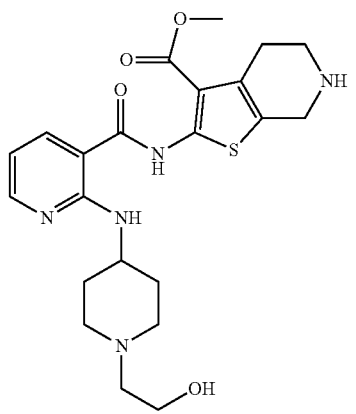
504
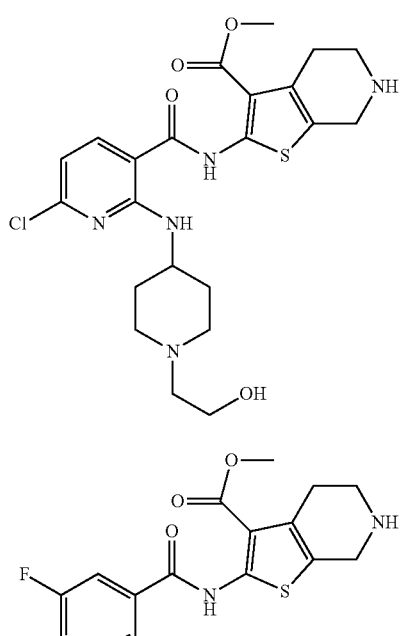
505
505
506
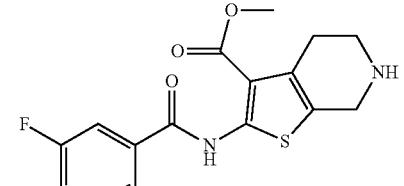

507 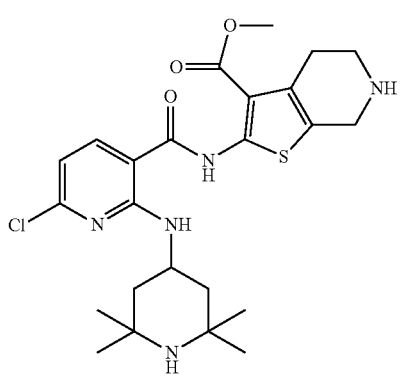
508 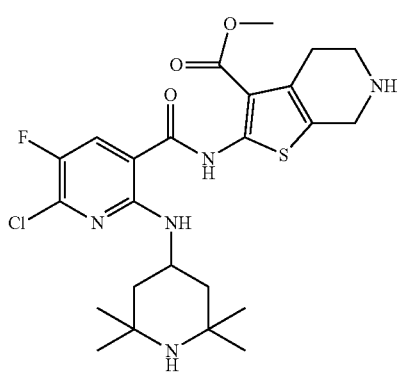
509 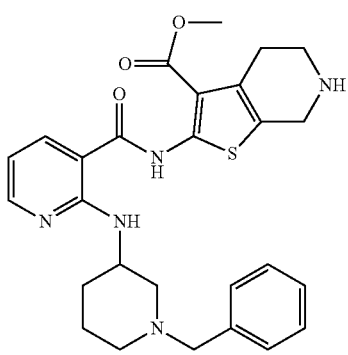
510 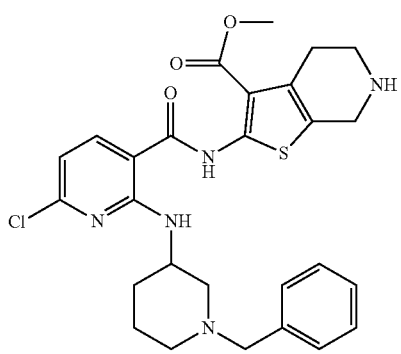
511 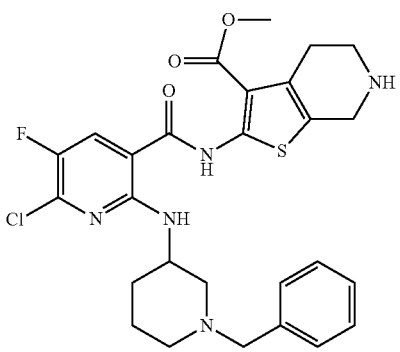
515 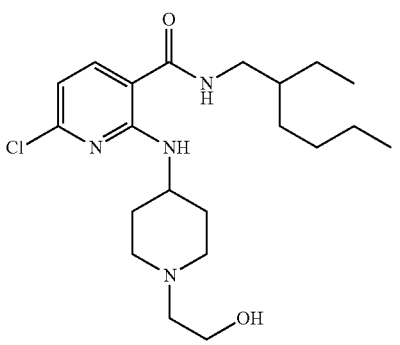
517 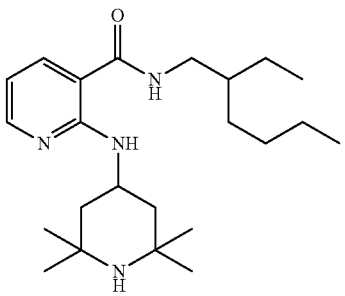
519 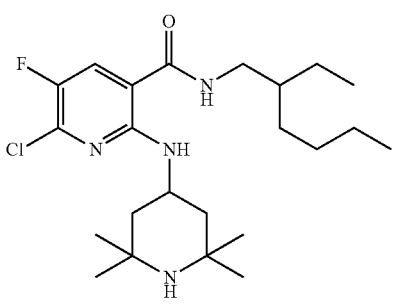
520 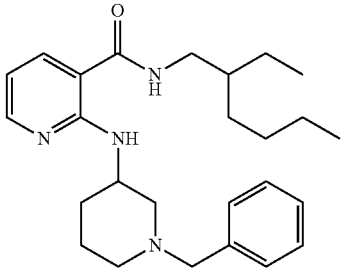

-continued

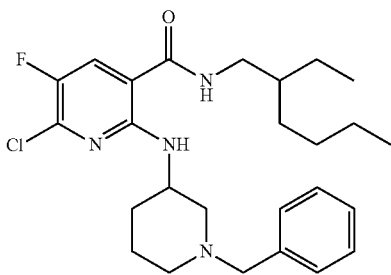

522

More preferred compounds of Chemical Formula I in accordance with the present invention or pharmaceutically acceptable salts thereof are:

2-(1-benzylpiperidin-4-ylamino)-N-(3-chlorophenyl)nicotinamide [103], 2-(1-benzylpiperidin-4-ylamino)-N-(4-phenoxyphenyl) nicotinamide [110], N-(3-chlorophenyl)-2-[1-(2-hydroxyethyl)piperidin-4-ylamino]nicotinamide [218], (S)-2-(1-benzylpiperidin-3-ylamino)-N-(3-chlorophenyl)nicotinamide [273], (S)—N-(3-chlorophenyl)-2-(1-tert-butoxycarbamoylpiperidin-3-ylamino)nicotinamide [276], 6-chloro-N-(3-chlorophenyl)-5-fluoro-2-[1-(2-hydroxyethyl)piperidin-4-ylamino]nicotinamide [312], (S)—N-(3-chlorophenyl)-2-(3-piperidylamino)nicotinamide [275], 2-(1-benzylpiperidin-4-ylsulfanyl)-N-(3-chlorophenyl) nicotinamide [290], 2-(1-benzylpiperidin-4-ylamino)-N-(5-methylthiazol-2-yl) nicotinamide [428], 2-{[2-(1-benzylpiperidin-4-ylamino)pyridine-3-carbonyl] amino}-4,5,6,7-tetrahydro-thieno[2,3-c]pyridine-3-carboxylic acid methyl ester [442], 2-{[2-(1-benzylpiperidin-3-ylamino)pyridine-3-carbonyl] amino}-4,5,6,7-tetrahydrothieno[2,3-c]pyridine-3-carboxylic acid methyl ester [509], and pharmaceutically acceptable salts thereof.

Higher preference would be made for 2-(1-benzylpiperidin-4-ylamino)-N-(3-chlorophenyl)nicotinamide [103] or a pharmaceutically acceptable salt thereof.

As used herein, the term "pharmaceutically acceptable salt" is intended to refer to a salt of an inorganic or organic acid typically used in the preparation of medicines in the art. The inorganic acid can be hydrochloric acid, bromic acid, sulfuric acid, or phosphoric acid; and examples of the organic acid include citric acid, acetic acid, lactic acid, stannic acid, fumaric acid, formic acid, propionic acid, oxalic acid, trifluoroacetic acid, methanesulfonic acid, benzenesulfonic acid, maleic acid, benzoic acid, gluconic acid, glycolic acid, succinic acid, 4-morpholineethane sulfonic acid, camphorsulfonic acid, 4-nitrobenzenesulfonic acid, hydroxyl-O-sulfonic acid, 4-toluenesulfonic acid, galacturonic acid, embonic acid, glutamic acid, aspartic acid.

In another aspect, the present invention provides a method for preparing the compound of Chemical Formula I, comprising reacting a compound of Chemical Formula II with a compound of Chemical Formula III in the presence of a base (hereinafter referred to as "Preparation Method 1"):

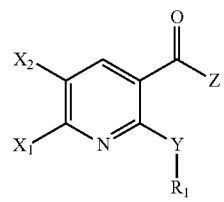

[Chemical Formula II]

$H_2N$—$R_2$ [Chemical Formula III]

wherein, $X_1$, $X_2$, $R_1$ and $R_2$ are respectively as defined hereinabove,

Z is chloro or bromo.

In Preparation Method 1, the compound of Chemical Formula II and the compound of Chemical Formula III may be commercially available, or may be synthesized using known methods. For example, the compound of Chemical Formula II can be synthesized according to the teachings of Organic Synthesis Collective Volume 1, (1941) 12 (F. K. Thayer), Organic Synthesis Collective Volume 1, 147 (1941) (B. Helferich and W. Schaefer), and Organic Synthesis Collective Volumn 2, 292 (1943) (John R. Ruhoff). The compound of Chemical Formula III can be made according to the teachings of Journal of Medicinal Chemistry, Vol. 22, 1171 (1979) (E. W. Byrnes and et al.), and Journal of the Chemical Society. Perkin Transactions 1. 1984, 229 (Lars J. S. Knutsen and et al.).

The base used in Preparation Method 1 can be appropriately selected from among various organic bases known to those skilled in the art. It is preferably, for example, a tertiary organic base selected from among triethylamine, N,N-diisopropylethylamine, N-methylmorpholine, DBU (1,8-Diazabicyclo[5.4.0]undec-7-ene), N-methylpiperidine, 4-dimethylaminopyridine, N,N-dimethylaniline, 2,6-lutidine, 4-N,N-dimethylaminopyridine, and pyridine. In Preparation Method 1, the base is used at a molar ratio of 1~5:1 to the compound of Chemical Formula II, and preferably used at a molar ratio of 3:1.

So long as it is typically used for amide coupling reaction in the art, any solvent can be adopted as the reaction solvent of Preparation Method 1. For example, acetonitrile, chloroform, methylenechloride, tetrahydrofuran, N,N-dimethylformamide, and N-methylpyrrolidinone can be preferably used, alone or in combination.

The reaction of Preparation Method 1 can be carried out at various temperatures, but preferably at −10° C. to room temperature (30° C.). More preferably, after addition of the base at 0° C. to 10° C., the reaction can be performed at room temperature or ambient temperature. However, the reaction temperature can depend on the base used, reaction solvents, and amounts thereof.

In a further aspect, the present invention provides a method for preparing the compound of Chemical Formula I, comprising reacting a compound of Chemical Formula IV with a compound of Chemical Formula V in the presence of a base (hereinafter referred to "Preparation Method 2"):

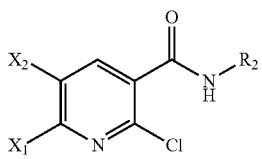

[Chemical Formula IV]

Y—R$_1$ [Chemical Formula V]

wherein,

X$_1$, X$_2$, and R$_2$ are respectively as defined hereinabove, and Y is —NH$_2$, —SH, or —OH.

In Preparation Method 2, the base can be an inorganic base typically available for those skilled in the art or an organic base existing as a solid phase at ambient temperature. Preferably, it is selected from the group consisting of potassium carbonate, potassium hydrogen carbonate, sodium carbonate, sodium hydrogen carbonate, sodium hydroxide, potassium hydroxide, calcium hydroxide, barium hydroxide, sodium methoxide, sodium ethoxide, sodium-t-butoxide, potassium-t-butoxide, sodium hydride, potassium hydride, sodium borohydride, sodium cyanoborohydride, and 4-N,N-dimethylaminopyridine.

In Preparation Method 2, the base is used at a molar ratio of 1~2:1 to the compound of Chemical Formula IV, and preferably used at a molar ratio of 1.2~1.5:1.

The reaction solvent useful in Preparation Method 2 is an organic solvent that refluxes at 100° C. or higher, known to those skilled in the art. Preferably, xylene, toluene, DMF, DMSO, dioxane, lutidine, pyridine, and N,N-dimethylaniline can be used, alone or in combination. Xylene means any of ortho-xylene, meta-xylene, and para-xylene. Lutidine means any of 2,3-lutidine, 2,4-lutidine, 2,5-lutidine, 2,6-lutidine, 3,4-lutidine, and 3,5-lutidine. More preferred solvent is ortho-xylene (o-xylene).

The reaction of Preparation Method 2 can be carried out at room temperature or in a range of reflux temperatures, with the latter being preferred.

In yet another aspect, the present invention provides a pharmaceutical composition for the prevention or treatment of a disease caused by the aberrant activity of vascular endothelial growth factor, comprising the compound of Chemical Formula I or a pharmaceutically acceptable salt thereof. The pharmaceutically acceptable salt is as described above.

Also, contemplated in accordance with still another aspect thereof is a method for preventing or treating a disease or symptom caused by aberrant activity of vascular endothelial growth factor (VEGF), comprising administering a therapeutically effective amount of the compound of Chemical Formula I or a pharmaceutically acceptable salt thereof to a mammal in need thereof, including a human.

The disease or symptom caused by the aberrant activity of vascular endothelial growth factor includes cancer, rheumatoid arthritis, diabetic retinopathy, keratitis, hyperemia, macular degeneration, choroidal neovascularization, neovascular glaucoma, ophthalmic diseases of corneal neovascularization, psoriasis, airway obstructive hemangiomas in lung, and obesity by angiogenesis.

In preferred embodiments, the disease or symptom caused by the aberrant activity of vascular endothelial growth factor is cancer.

In accordance with a still further aspect thereof, the preset invention addresses a pharmaceutical composition for the suppression of vessel formation, comprising a compound of Chemical Formula I or a pharmaceutically acceptable salt thereof. The pharmaceutical composition for the suppression of vessel formation in accordance with the present invention is preferably an anticancer agent.

In addition, the pharmaceutical composition of the present invention may further comprise one or more active ingredients exhibiting an activity equal to or similar to that of the compound of Chemical Formula I or a pharmaceutically acceptable salt thereof.

In addition to the active ingredient, the composition in accordance with the present invention may comprise at least one pharmaceutically acceptable carrier. Examples of the pharmaceutically acceptable carrier include saline solution, sterile water, Ringer's solution, buffered saline solution, dextrose solution, maltodextrin solution, glycerol, ethanol, and a mixture of two or more thereof. If necessary, the composition may further include other conventional additives, such as antioxidants, buffers, and bacteriostatic agents. Also, the composition may additionally include diluents, dispersants, surfactants, binders and lubricants in order to be formulated into injection formulations, such as aqueous solution, suspension and emulsion, pills, capsules, granules or tablets. Furthermore, the composition may be preferably formulated depending on its components or purposes, using a suitable method known in the art, for example, the method described in Remington's Pharmaceutical Science (latest edition), Mack Publishing Company, Easton Pa.

According to the intended use, the composition may be administered orally or via parenteral routes (e.g., intravenous, subcutaneous, intraperitoneal or topical). The specific therapeutically effective dose level for any particular patient may vary depending on a variety of factors, including the patient's weight, age, gender, general health status and diet, the time of administration, route of administration, rate of excretion of the composition, and severity of the illness. The compound of Chemical Formula I or a pharmaceutically acceptable salt thereof can be administered in a daily dosage ranging from about 5 to 75 mg, and preferably 5 to 50 mg. The daily dosage can be preferably given in a single dose.

For application to the prevention and treatment of a disease caused by aberrant activity of vascular endothelial growth factor, the composition can be used alone or in combination with other therapies including surgery, hormonal therapy, chemical therapy and/or biological reaction regulators.

In accordance with a yet further aspect thereof, the present invention addresses a method for preventing or treating a disease, comprising administering a compound of Chemical Formula I, at least one of the enumerated compounds above, or a pharmaceutically acceptable salt thereof to a subject including a mammal.

In accordance with yet another aspect thereof, the present invention addresses a method for preventing or treating a disease, comprising administering a compound of Chemical Formula I, at least one of the enumerated compounds above, or a pharmaceutically acceptable salt thereof to a subject including a mammal, wherein the disease is selected from the group consisting of cancer, rheumatoid arthritis, diabetic retinopathy, keratitis, hyperemia, macular degeneration, choroidal neovascularization, neovascular glaucoma, ophthalmic diseases of corneal neovascularization, psoriasis, airway obstructive hemangiomas in lung, and obesity by angiogenesis.

Advantageous Effects

Because the present invention is capable of potently suppressing the activity of vascular endothelial growth factor, the compounds of the present invention are applicable to the prevention and treatment of diseases caused by aberrant activity of vascular endothelial growth factor, and available as an anti-angiogenic agent.

MODE FOR INVENTION

Figure 1:
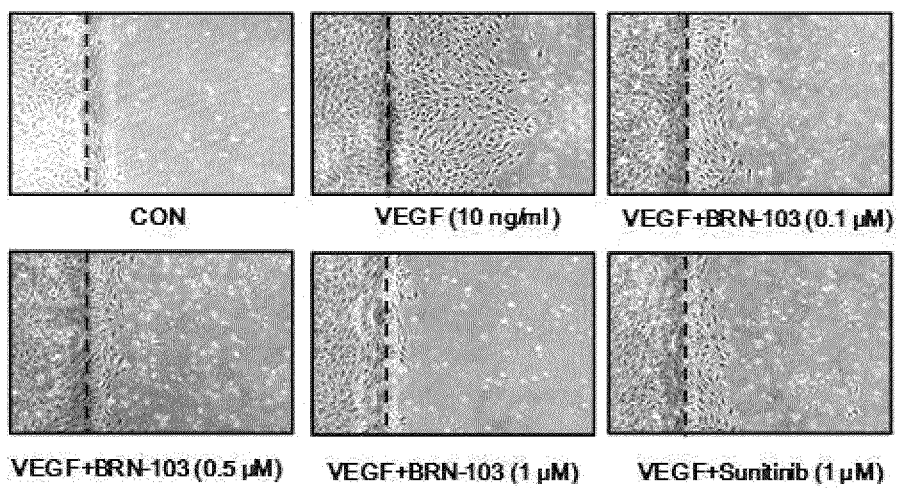
FIGS. 1 and 2 are photographs showing results of Experimental Example 2-2.

A better understanding of the present invention can be obtained through the following examples which are set forth to illustrate, but are not to be construed as limiting the present invention.

In the following Examples, unless specifically stated, all reagents and solvents were purchased from Aldrich, ICI, Wako or Junsei, and $^1$H-NMR and Mass data were measured using Gemini 200 (Verian) and 1100MSD (Hewlett Packard), respectively.

The 'desiccant' used in the Examples was 'sodium sulfate' unless otherwise stated.

PREPARATION EXAMPLES

Intermediates for the preparation of compounds of Table 1 were synthesized in the following Preparation Examples.

Preparation Example 1

Preparation of Methyl 2-amino-4,5,6,7-tetrahydro-thieno[2,3-c]pyridine-3-carboxylate hydrochloride (reference: WO 2010/112124)

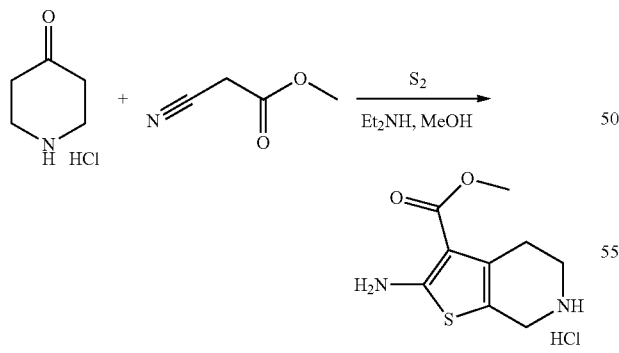

To a solution of piperidin-2-one hydrochloride (5 g, 37.43 mmol, 1.05 eq), methyl cyanoacetate (37.43 mmol, 1.05 eq), and sulfur (35.65 mmol 1.05 eq) in methanol (20 ml) was added diethylamine (35.65 mmol). The reaction mixture was stirred at room temperature for 5 hrs, and the precipitate thus formed was washed with isopropanol (10 ml) and methanol (20 ml) and hot-air dried to afford the title compound. Yield 42.6%, basified Cpd $^1$H NMR (CDCl$_3$) δ 6.01 (s, 2H), 3.79-3.77 (m, 5H), 3.07 (t, 2H), 2.72 (m, 2H) ppm.

Preparation Example 2

Preparation of Methyl 2-amino-6-benzyl-4,5,6,7-tetrahydro-thieno[2,3-c]pyridine-3-carboxylate (Reference: WO 2010/112124)

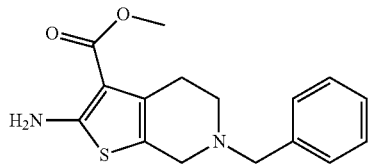 [SMILES: COC(=O)c1c(N)sc2c1CCN(Cc1ccccc1)C2]

The title compound was prepared in the same manner as in Preparation Example 1, with the exception that 1-benzylpiperidin-2-one, instead of piperidin-2-one hydrochloride, was used in the same molar amount. Yield 81.4% $^1$H NMR (CDCl$_3$) δ 7.37-7.30 (m, 5H), 6.01 (s, 2H), 3.78 (s, 3H), 3.68 (s, 2H), 3.41 (s, 2H), 2.85-2.75 (m, 4H) ppm.

Preparation Example 3

Preparation of 2-Amino-4,7-dihydro-5H-thieno[2,3-c]pyridine-3,6-dicarboxylic acid 6-ethyl ester 3-methyl ester (Reference: WO 2010/112124)

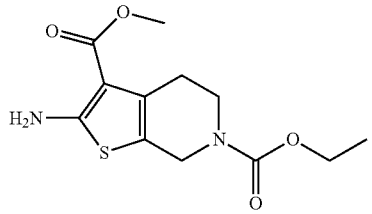 [SMILES: CCOC(=O)N1CCc2c(sc(N)c2C(=O)OC)C1]

The title compound was prepared in the same manner as in Preparation Example 1, with the exception that piperidin-2-one-1-yl ethoxycarbamate, instead of piperidin-2-one hydrochloride, was used in the same molar amount. Yield: 78.1%, $^1$H NMR (CDCl$_3$) δ 6.05 (s, 2H), 4.40 (s, 2H), 4.17 (q, 2H), 3.80 (s, 3H), 3.67 (t, 2H), 2.81 (t, 2H), 1.28 (t, 3H) ppm.

Preparation Example 4

Preparation of 2-amino-4,7-dihydro-5H-thieno[2,3-c]pyridine-3,6-dicarboxylic acid 6-tert-butyl ester 3-methyl ester (Reference: WO 2010/112124)

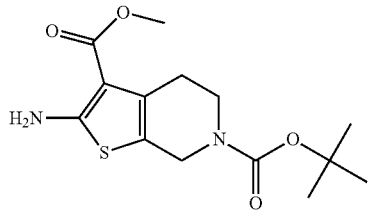 [SMILES: COC(=O)c1c(N)sc2c1CCN(C(=O)OC(C)(C)C)C2]

The title compound was prepared in the same manner as in Preparation Example 1, with the exception that piperidin-2-one-1-yl tert-butoxycarbamate, instead of piperidin-2-one hydrochloride, was used in the same molar amount. Yield: 80.9%, $^1$H NMR (CDCl$_3$) δ 6.07 (s, 2H), 4.35 (s, 2H), 3.79 (s, 3H), 3.61 (t, 2H), 2.78 (t, 2H), 1.47 (s, 9H) ppm.

Preparation Example 5

Preparation of 2-chloro-N-(3-chlorophenyl)nicotinamide

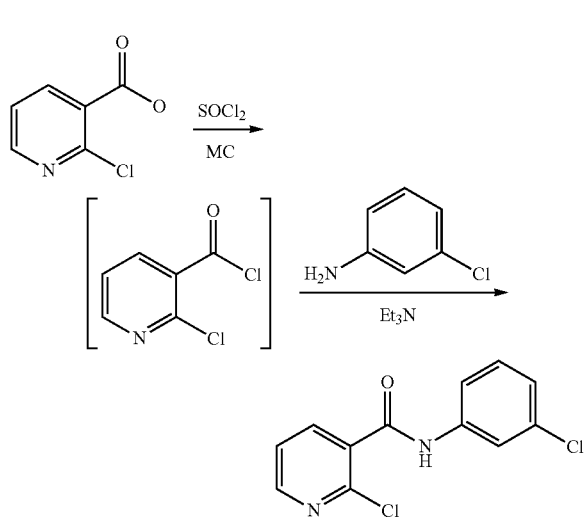

Step 1. Preparation of 2-chloronicotinyl chloride

A solution of 2-chloronicotinic acid (10 g, 63.47 mmol, 1 eq) in 70 ml of methylene chloride was stirred in an ice bath. Thionyl chloride (76.16 mmol, 1.2 eq) was added dropwise over 30 min to the solution, after which the ice bath was removed, and the solution was stirred at room temperature for 30 min and then under reflux for 1 hr. The reaction mixture was cooled and used in the next step without further purification.

Step 2. Preparation of 2-chloro-N-(3-chlorophenyl)nicotinamide

The solution obtained in step 1 was placed in an ice bath and triethylamine (152.32 mmol, 2.4 eq) was added over 30 min, and then stirred at room temperature for 30 minutes. Again, 3-chloroaniline (76.16 mmol, 1.2 eq) was added to the reaction mixture for 30 min, followed by stirring under reflux for 3 hrs. When the reaction was completed under the monitoring of thin layer silica chromatography, the reaction mixture was cooled to room temperature and the reaction was terminated using with pure water. Then resultant solution was extracted two or three times with MC (methylene chloride, 50 ml). A pool of the organic layers was washed with 70 ml of 1N-HCl and neutralized with sodium bicarbonate. After being dried over sodium sulfate, the organic layer pool was concentrated in reduced pressure. Purification by column chromatography (mobile phase; 30 (v/v) % EA in hexane) afforded the title compound. Total yield: 81.6% $^1$H NMR (CDCl$_3$+4 drop CD$_3$OD) δ 8.41 (dd, 1H), 8.00 (dd, 1H), 7.74 (st, 1H), 7.49 (d, 1H), 7.35 (dd, 1H), 7.27 (t, 1H), 7.13 (d, 1H) ppm.

Preparation Example 6

Preparation of 2-Chloro-N-(4-phenoxyphenyl)nicotinamide

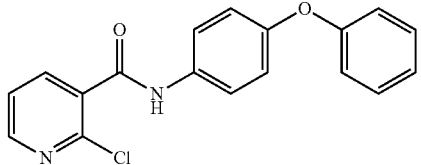 [SMILES: O=C(Nc1ccc(Oc2ccccc2)cc1)c1cccnc1Cl]

The title compound was synthesized in the same manner as in step 2 of Preparation Example 5, with the exception that 4-phenoxyaniline, instead of 3-chloroaniline, was used in the same molar amount. Total yield: 91.2% $^1$H NMR (CDCl$_3$) δ 8.52 (dd, 1H), 8.22 (dd, 1H), 8.17 (s, 1H), 7.62 (d, 2H), 7.46-7.32 (m, 3H), 7.15-7.0 (m, 5H) ppm.

Preparation Example 7

Preparation of N-(1-Acetyl-3,3-dimethyl-2,3-dihydro-1H-indol-6-yl)-2-chloronicotinamide

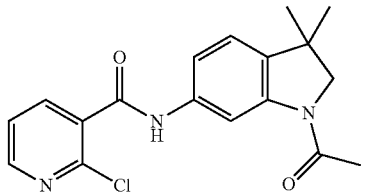 [SMILES: CC(=O)N1CC(C)(C)c2ccc(NC(=O)c3cccnc3Cl)cc21]

The title compound was prepared in the same manner as in step 2 of Preparation Example 5, with the exception that 1-acetyl-6-amino-3,3-dimethyl-2,3-dihydro-1H-indole, instead of 3-chloroaniline, was used in the same molar amount. Total yield: 80.4% $^1$H NMR (CDCl$_3$) δ 9.01 (s, 1H), 8.42 (d, 1H), 8.07 (d, 1H), 8.05 (s, 1H), 7.93 (d, 1H), 7.33 (dd, 1H), 7.14 (d, 1H), 3.75 (s, 2H), 2.07 (s, 3H), 1.37 (s, 6H) ppm.

Preparation Example 8

Preparation of 2,6-Dichloro-N-(3-chlorophenyl)nicotinamide

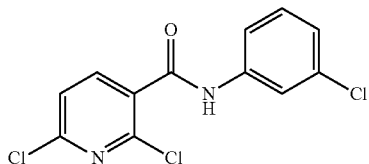 [SMILES: O=C(Nc1cccc(Cl)c1)c1ccc(Cl)nc1Cl]

Step 1. Preparation of 2,6-dichloronicotinyl chloride

The title compound was prepared in the same manner as in step 1 of Preparation Example 5, with the exception that 2,6-dichloronicotinic acid, instead of 2-chloronicotinic acid, was used in the same molar amount.

Step 2. Preparation of 2,6-dichloro-N-(3-chlorophenyl) nicotinamide

The title compound was prepared in the same manner as in step 2 of Preparation Example 5, with the exception that 2,6-dichloronicotinyl chloride obtained in step 1, instead of 2-chloronicotinyl chloride, was used in the same molar amount. Total Yield: 75.3% $^1$H NMR (CDCl$_3$+2 drops DMSO-d$_6$) δ 9.82 (s, 1H), 7.89 (d, 1H), 7.77 (st, 1H), 7.52 (dt, 1H), 7.34 (d, 1H), 7.23 (t, 1H), 7.08 (dq, 1H) ppm.

Preparation Example 9

Preparation of 2,6-Dichloro-N-(3-chlorophenyl)-5-fluoronicotinamide

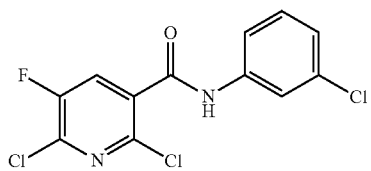 [SMILES: O=C(Nc1cccc(Cl)c1)c1cc(F)c(Cl)nc1Cl]

Step 1. Preparation of 2,6-dichloro-5-fluoronicotinyl chloride

The title compound was prepared in the same manner as in step 1 of Preparation Example 5, with the exception that 2,6-dichloro-5-fluoronicotinic acid, instead of 2-chloronicotinic acid, was used in the same molar amount.

Step 2. Preparation of 2,6-dichloro-N-(3-chlorophenyl)-5-fluoronicotinamide

The title compound was prepared in the same manner as in step 2 of Preparation Example 5, with the exception that 2,6-dichloro-5-fluoronicotinyl chloride obtained in step 1, instead of 2-chloronicotinyl chloride, was used in the same molar amount. Total yield: 78.4% $^1$H NMR (CDCl$_3$) δ 8.35 (s, 1H), 8.08 (d, 1H), 7.76 (s, 1H), 7.48-7.19 (m, 3H) ppm.

Preparation Example 10

Preparation of 2-[(2-Chloropyridine-3-carbonyl)-amino]-4,7-dihydro-5H-thieno[2,3-c]pyridine-3,6-didicarboxylic acid 6-tert-butyl ester 3-methyl ester

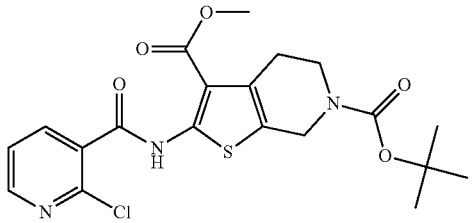 [SMILES: COC(=O)c1c(NC(=O)c2cccnc2Cl)sc2c1CCN(C(=O)OC(C)(C)C)C2]

The title compound was prepared in the same manner as in step 2 of Preparation Example 5, with the exception that 2-amino-4,7-dihydro-5H-thieno[2,3-c]pyridine-3,6-dicarboxylic acid 6-tert-butyl ester 3-methyl ester obtained from Preparation Example 4, instead of 3-chloroaniline, was used in the same molar amount. Total yield: 56.7% $^1$H NMR (CDCl$_3$) δ 8.58 (d, 1H), 8.23 (d, 1H), 7.44 (m, 1H), 4.57 (s, 2H), 3.92 (s, 3H), 3.69 (t, 2H), 2.92 (t, 2H), 1.49 (s, 9H) ppm.

Preparation Example 11

Preparation of 2-[(2,6-Dichloropyridine-3-carbonyl)-amino]-4,7-dihydro-5H-thieno[2,3-c]pyridine-3,6-dicarboxylic acid 6-tert-butyl ester 3-methyl ester

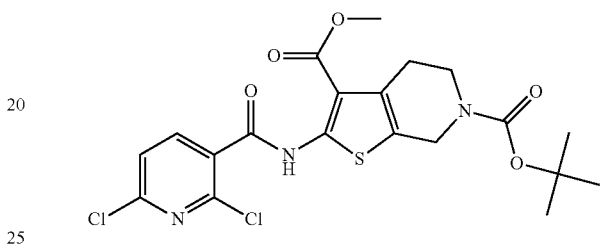

The title compound was prepared in the same manner as in step 2 of Preparation Example 5, with the exception that 2,6-dichloronicotinyl chloride, instead of 2-chloronicotinyl chloride, and 2-amino-4,7-dihydro-5H-thieno[2,3-c]pyridine-3,6-dicarboxylic acid 6-tert-butyl ester 3-methyl ester obtained in Preparation Example 4, instead of 3-chloroaniline, were used in the same molar amounts. Total yield: 43.4% $^1$H NMR (CDCl$_3$) δ 7.65 (d, 1H), 7.39 (m, 1H), 3.82 (s, 2H), 3.78 (s, 3H), 3.48 (t, 2H), 2.98 (t, 2H), 1.60 (s, 9H) ppm.

Preparation Example 12

Preparation of N-(1-Acetyl-3,3-dimethyl-2,3-dihydro-1H-indol-6-yl)-2-chloronicotinamide{2-[(2,6-dichloro-5-fluoro-pyridine-3-carbonyl)-amino]-4,7-dihydro-5H-thieno[2,3-c]pyridine-3,6-dicarboxylic acid 6-tert-butyl ester 3-methyl ester}

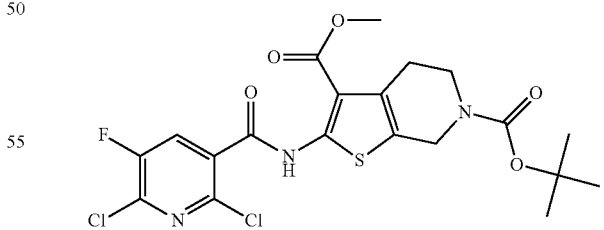

The title compound was prepared in the same manner as in step 2 of Preparation Example 5, with the exception that 2,6-dichloro-5-fluoronicotinyl chloride obtained in Preparation Example 9, instead of 2-chloronicotinyl chloride, and 2-amino-4,7-dihydro-5H-thieno[2,3-c]pyridine-3,6-dicarboxylic acid 6-tert-butyl ester 3-methyl ester obtained in Preparation Example 4, instead of 3-chloroaniline, were used in the same molar amounts. Yield: 49.7% $^1$H NMR (CDCl$_3$) δ 8.12 (d, 1H), 4.56 (s, 2H), 3.92 (s, 3H), 3.69 (t, 2H), 2.92 (t, 2H), 1.50 (s, 9H) ppm.

Preparation Example 13

Preparation of N-(2-ethylhexyl)-2-chloronicotinamide

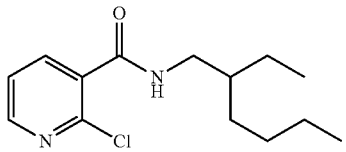 [SMILES: CCCCC(CC)CNC(=O)c1cccnc1Cl]

The title compound was prepared in the same manner as in step 2 of Preparation Example 5, with the exception that 2-ethylhexylamine, instead of 3-chloroaniline, was used in the same molar amount. Total yield: 92.4% $^1$H NMR (CDCl$_3$) δ 8.41 (d, 1H), 8.04 (d, 1H), 7.31 (m, 1H), 6.50 (br, 1H), 3.41 (t, 2H), 1.58 (m, 1H), 1.48-1.28 (m, 8H), 0.97-0.88 (m, 6H) ppm.

Preparation Example 14

Preparation of 2,6-Dichloro-N-(2-W ethylhexyl)-nicotinamide

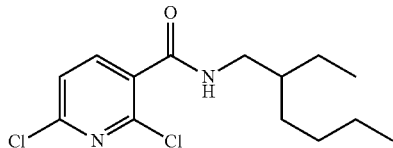 [SMILES: CCCCC(CC)CNC(=O)c1ccc(Cl)nc1Cl]

The title compound was prepared in the same manner as in step 2 of Preparation Example 5, with the exception that 2,6-dichloronicotinyl chloride of Preparation Example 8, instead of 2-chloronicotinyl chloride, and 2-ethylhexylamine, instead of 3-chloroaniline, were used in the same molar amounts. Total yield: 89.6% $^1$H NMR (CDCl$_3$) δ 8.09 (d, 1H), 7.37 (d, 1H), 6.55 (br, 1H), 3.43 (t, 2H), 1.59 (m, 1H), 1.49-1.29 (m, 8H), 0.97-0.88 (m, 6H) ppm.

Preparation Example 15

Preparation of N-(2-Ethylhexyl)-2,6-dichloro-5-fluoronicotinamide

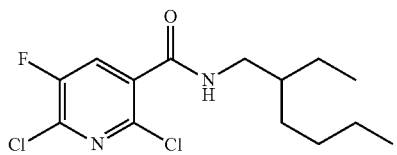 [SMILES: CCCCC(CC)CNC(=O)c1cc(F)c(Cl)nc1Cl]

The title compound was prepared in the same manner as in step 2 of Preparation Example 5, with the exception that 2,6-dichloro-5-fluoronicotinyl chloride of Preparation Example 8, instead of 2-chloronicotinyl chloride, and 2-eth-ylhexylamine, instead of 3-chloroaniline, were used in the same molar amounts. Total yield: 90.1% $^1$H NMR (CDCl$_3$) δ 8.0 (d, 1H), 6.65 (br, 1H), 3.44 (t, 2H), 1.58 (m, 1H), 1.48-1.27 (m, 8H), 0.97-0.88 (m, 6H) ppm.

Preparation Example 16

Preparation of 2-(1-Benzylpiperidin-4-ylamino)nicotinic acid

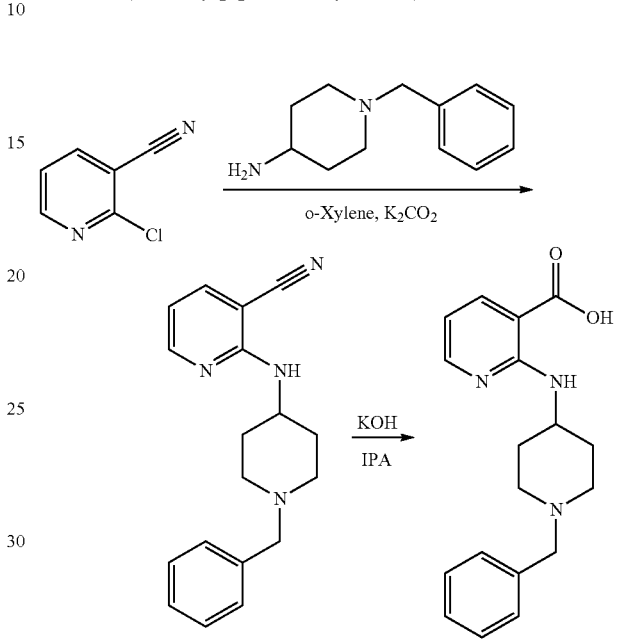

Step 1. Preparation of 2-(1-benzylpiperidin-4-ylamino) nicotinonitrile

In 500 ml of ortho-xylene, 100 g of 2-chloronicotinonitrile, 108.82 g of anhydrous potassium carbonate, and 133.83 ml of 4-amino-1-benzylpiperidine were together stirred for 24 hrs under reflux. This reaction mixture was cooled to room temperature, added with 500 ml of ethyl acetate and 1,000 ml of pure water, and adjusted to a pH of about 2-3 with conc. HCl. The aqueous fraction thus formed was obtained, washed again with 300 ml of ethylacetate, and adjusted to a pH of about 9-10 with sodium hydroxide in an ice bath while stirring. After completion of addition of sodium hydroxide, the fraction was stirred for an additional 1 hr, filtered, washed with water, and hot air dried to afford 137.4 g of the title compound (yield: 71.5%). $^1$H NMR (CDCl$_3$) δ 8.26 (dd, 1H), 7.63 (dd, 1H), 7.36-7.28 (m, 5H), 6.59 (m, 1H), 5.0 (d, 1H), 4.14-3.97 (m, 1H), 3.53 (s, 2H), 2.88 (d, 2H), 2.22 (t, 2H), 2.1-1.98 (m, 2H), 1.68-1.47 (m, 2H) ppm.

Step 2. Preparation of 2-(1-benzylpiperidin-4-ylamino) nicotinic acid

To a solution of 100 g of 2-(1-benzylpiperidin-4-ylamino) nicotinonitrile obtained in step 1 in 200 ml of isopropanol was added 63.22 g of potassium hydroxide, followed by stirring for 12 hrs under reflux. The reaction mixture was cooled to a room temperature, mixed with 800 ml of pure water and 500 ml of ethylacetate, and adjusted to a pH of 2-3 with conc. HCl. The aqueous layer was obtained, washed with 500 ml of ethylacetate, and adjusted to a pH of 6-8 with sodium hydroxide in an ice bath while stirring. The mixture was stirred for an additional 1 hr and precipitates were formed during stirring, and the precipitates were filtered and washed with distilled water. The precipitates were slurried with 300 ml of pure water, stirred for 30 min, and filtered. The precipitates were again slurried with 150 ml of acetone, stirred for 30 min, and filtered. This precipitates were washed with a small amount of acetone and hot air dried to afford 93.7 g of the title compound (Yield: 88.1%). $^1$H NMR (CDCl$_3$) δ 8.89 (d, 1H), 8.29 (d, 1H), 8.10 (d, 1H), 7.57-7.42 (m, 5H), 4.35 (s, 2H), 4.30 (m, 1H), 3.47 (d, 2H), 2.73 (t, 2H), 2.39 (d, 2H), 2.01-1.80 (m, 2H) ppm.

Preparation Example 17

Preparation of 4-Amino-1-(2-hydroxyethyl) piperidine

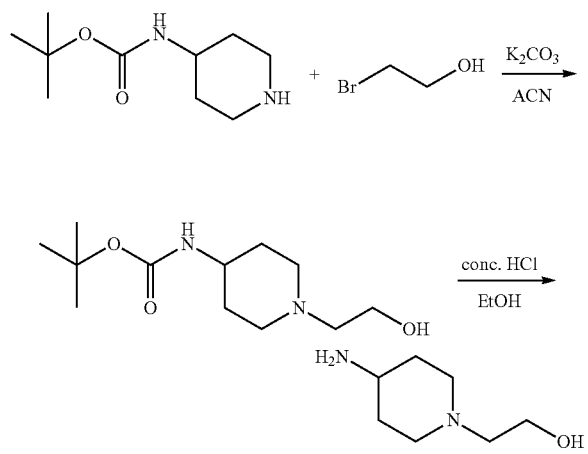

Reference: J. Med. Chem. 50 (2007) 3561

Step 1. Preparation of tert-butyl 1-(2-hydroxyethyl)piperidin-4-ylcarbamate

A solution of 0.5 g of tert-butyl 4-piperidinylcarbamate, 0.21 ml of 2-bromoethanol and 2.76 g of K$_2$CO$_3$ in 10 ml of acetonitrile was stirred for 5 hrs under reflux. The reaction mixture was cooled to a room temperature, filtered to remove solids, and concentrated. The concentrate was purified by silica gel column chromatography (mobile phase: 20 (v/v) % EA in hexane) to afford 0.58 g of the title compound (Yield: 94%). $^1$H NMR (CDCl$_3$) δ 4.76 (d, 1H), 3.65 (t, 2H), 3.48 (m, 1H), 2.92 (m, 2H), 2.59 (t, 2H), 2.26 (m, 2H), 1.94 (m, 2H), 1.52 (m, 2H), 1.44 (s, 9H) ppm.

Step 2: Preparation of 4-amino-1-(2-hydroxyethyl) piperidine

To a solution of 0.58 g of tert-butyl 1-(2-hydroxyethyl) piperidin-4-ylcarbamate obtained in step 1 in 10 ml of ethanol was added 1 ml of conc. HCl, followed by stirring for 2 hrs under reflux. The reaction mixture was cooled to room temperature, and concentrated in a reduced pressure to remove solvent. The residue was added with 10 ml of distilled water, neutralized with saturated sodium hydrogen carbonate aqueous solution, and extracted twice with 10 ml of methylene chloride. After being dried over a desiccant, the fraction was concentrated in a reduced pressure to afford 0.33 g of the title compound (Yield: 95%). $^1$H NMR (CDCl$_3$) δ 3.68 (s, 2H), 3.60 (t, 2H), 2.86 (d, 2H), 2.69 (m, 1H), 2.53 (t, 2H), 2.11 (t, 2H), 1.82 (d, 2H), 1.42 (t, 2H) ppm.

Preparation Example 18

Preparation of 3-Amino-1-benzylpiperidine

Reference: J. Med. Chem. 23 (1980) 848

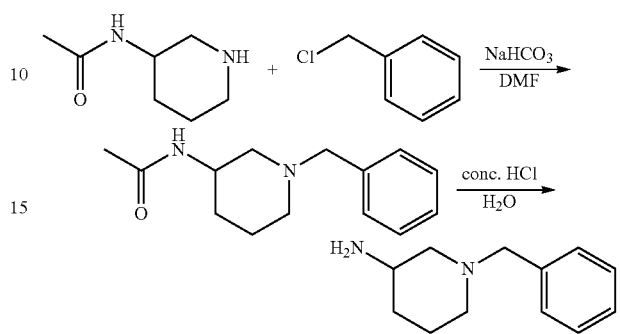

Step 1. Preparation of 3-(N-acetamino)-1-benzylpiperidine

A solution of 2 g of 3-(N-acetamino)piperidine and 1.3 g of sodium bicarbonate in 7 ml of DMF (dimethylformamide) was stirred for 30 min in an ice bath. To the reaction mixture was added, dropwise, 1.7 ml of benzyl chloride for 15 min, and stirred at room temperature for 15 hrs. The solvent was removed by concentration in a reduced pressure, followed by adding pure water. The solid thus formed was filtered and recrystallized using diethylether to afford 2.13 g of the title compound (Yield: 87.5%). $^1$H NMR (CDCl$_3$) δ 7.31 (m, 5H), 4.15-4.03 (m, 1H), 3.49 (s, 2H), 2.59 (d, 1H), 2.43 (d, 2H), 2.19 (m, 1H), 1.98 (s, 3H), 1.92 (d, 2H), 1.74-1.52 (m, 4H) ppm.

Step 2: Preparation of 3-Amino-1-benzylpiperidine

A solution of 2.13 g of 3-(N-acetamido)-1-benzylpiperidine in 10 ml of 6 N HCl was stirred for 1 hr under reflux. The reaction mixture was cooled to room temperature, and 6 N ammonium hydroxide was added until the pH was adjusted to 9-10. After 4 rounds of extraction with 15 ml of chloroform per round, the extract was dried over sodium sulfate and concentrated in a reduced pressure to afford 1.21 g of the title compound (Yield: 96.3%). $^1$H NMR (CDCl$_3$) δ 7.31 (m, 5H), 3.51 (s, 2H), 2.93-2.61 (m, 3H), 2.06 (t, 1H), 1.90-1.52 (m, 4H), 1.20-1.02 (m, 1H) ppm.

Preparation Example 19

Preparation of 4-(1-Bromoethyl)-6-chloro-5-fluoropyrimidine

Reference: Org. Process Res. Dev. 5 (2001) 28

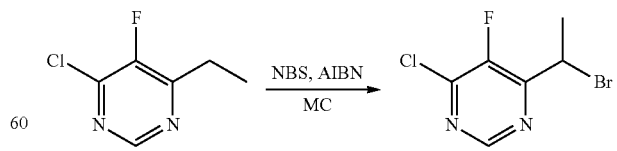

A solution of 5 g of 6-chloro-4-ethyl-5-fluoropyrimidine, 6.65 g of NBS, and 0.51 g of AIBN in 50 ml of methylene chloride was stirred for 12 hrs under reflux. The reaction was cooled to room temperature and 30 ml of pure water was added. The organic layer was collected, and the aqueous fraction was extracted with 30 ml of methylene chloride. The organic layers thus obtained were pooled and washed with 30 ml of 10% sodium metabisulfite, and then with pure water. After dehydration with a desiccant, the obtained product was concentrated under reduced pressure to afford 6.95 g of the title compound (Yield: 95.1%). $^1$H NMR (CDCl$_3$) δ 8.80 (s, 1H), 5.35 (q, 1H), 2.08 (d, 3H) ppm.

Preparation Example 20

Preparation of 6-Amino-3-methyl-2-methylsulfanyl-3H-quinazolin-4-one

Reference: Bioorg. Med. Chem. 14 (2006) 8608

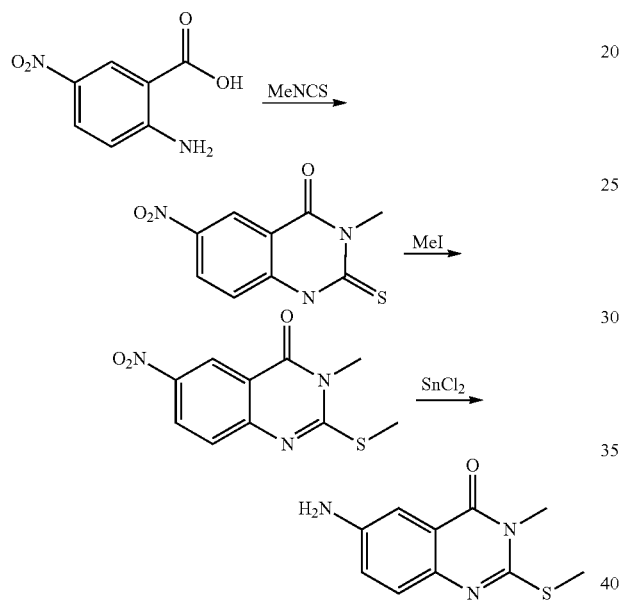

Step 1. Preparation of 3-methyl-6-nitro-2-thioxo-2,3-dihydro-1H-quinazolin-4-one A solution of 3.48 g of 5-nitroanthranilic acid, 1.68 g of methylisothiocyanate, and 3.72 ml of triethylamine in 70 ml of ethanol was stirred for 4 hrs under reflux. The reaction mixture was cooled to room temperature, and concentrated in a reduced pressure to remove the solvent. The residue was recrystallized in diethyl ether to afford 3.91 g of the title compound (Yield 86.2%)$^1$H NMR (DMSO-d$_6$) δ 8.19 (d, 1H), 8.16 (sd, 1H), 8.05 (dd, 1H), 3.67 (s, 3H) ppm.

Step 2. Preparation of 2-methylthio-3-methyl-6-nitro-3H-quinazolin-4-one

A solution of 3.91 g of 3-methyl-6-nitro-2-thioxo-2,3-dihydro-1H-quinazolin-4-one obtained in step 1, 8.24 ml of methane iodide, and 2.73 g of anhydrous potassium carbonate in 82 ml of acetone was stirred for 8 hrs under reflux. While remaining hot, the reaction mixture was filtered to remove precipitates, and washed with acetone. The filtrate was concentrated in a reduced pressure, and the residue was slurried with 20 ml of isopropanol and stirred for 30 min. The resultant mixture was filtered and dried to afford 2.84 g of the title compound (yield: 68.7%). $^1$H NMR (DMSO-d$_6$) δ 8.30 (d, 1H), 8.26 (sd, 1H), 8.16 (dd, 1H), 3.56 (s, 3H), 2.71 (s, 3H) ppm.

Step 3. Preparation of 6-amino-2-methylthio-3-methyl-3H-quinazolin-4-one

A solution of 1.5 g of 2-methylthio-3-methyl-6-nitro-3H-quinazolin-4-one obtained in step 2, 6.73 g of tin (II) chloride dihydrate, and 0.11 g of sodium borohydride in 10 ml of ethanol was stirred for 3 hrs under reflux. The reaction mixture was added with 20 ml of pure water, and neutralized with an aqueous 2N-sodium hydroxide solution. After removal of ethanol by concentrating in reduced pressure, the residue was extracted twice with 15 ml of diethyl ether. The extract was dried over a desiccant and concentrated in a reduced pressure to afford 0.55 g of the title compound (Yield: 41.7%). $^1$H NMR (CDCl$_3$) δ 8.02 (d, 1H), 6.71 (s, 1H), 6.68 (d, 1H), 3.57 (s, 3H), 2.62 (s, 3H) ppm.

EXAMPLES

Compounds of Table 1 were synthesized in the following Examples.

Example 1

Preparation of 2-(1-Benzylpiperidin-4-ylamino)-N-(3-chlorophenyl)nicotinamide [103]

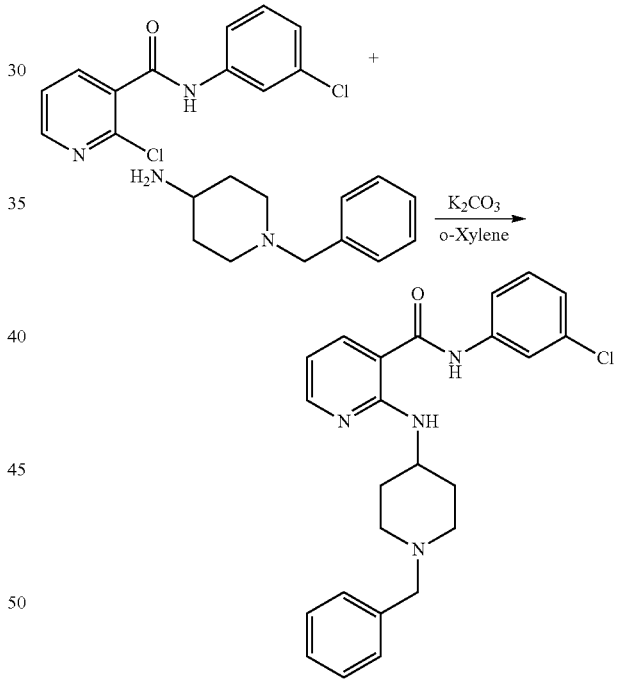

A solution of 2-chloro-(N-3-chlorophenyl)nicotinamide (280 mg, 1.05 mmol, 1.05 eq) prepared in Preparation Example 5, 4-amino-1-benzylpiperidine (1.0 mmol), and anhydrous potassium carbonate (1.3 mmol) in ortho-xylene was stirred for 24 hrs under reflux. The reaction mixture was cooled to a room temperature, added with ethylacetate, and extracted twice with 1N HCl. The aqueous layer thus formed was washed with 30 ml of ethylacetate, adjusted to a pH of about 9-10 by adding 2 N sodium hydroxide, and extracted two or three times with 20 ml of methylene chloride. The organic layer was dried over a desiccant, and concentrated in a reduced pressure. A desired fraction obtained by purification through silica gel chromatography was concentrated in a reduced pressure and dried in a vacuum to afford the title compound. Yield: 66.5% ¹H NMR (DMSO-d₆) δ8.15~8.30 (m, 2H), 8.03 (d, 1H), 7.90 (s, 1H), 7.66 (d, 1H), 7.60 (d, 1H), 7.30~7.60 (m, 6H), 7.19 (d, 1H), 6.70 (m, 1H), 4.10 (bs, 1H), 3.95 (s, 1H), 2.85~3.15 (m, 2H), 2.70~2.85 (m, 2H), 1.90~2.15 (m, 2H), 1.60~1.85 (m, 2H) ppm.

Example 2

Preparation of N-(3-Chlorophenyl)-2-(4-phenoxyanilino)nicotinamide [104]

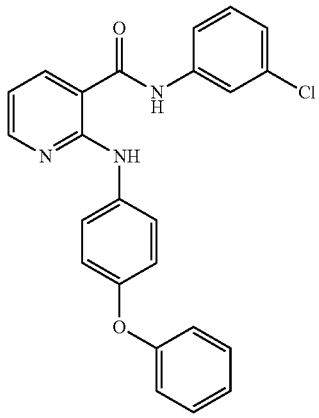 [SMILES: O=C(Nc1cccc(Cl)c1)c1cccnc1Nc1ccc(Oc2ccccc2)cc1]

The title compound was prepared in the same manner as in Example 1, with the exception that 4-phenoxyaniline, instead of 4-amino-1-benzylpiperidine, was used in the same molar amount (Yield: 72.3%). ¹H NMR (DMSO-d₆) δ 8.37 (d, 1H), 8.21 (d, 1H), 7.92 (s, 1H), 7.60~7.76 (m, 3H), 7.30~7.43 (m, 3H), 7.21 (d, 1H), 7.06 (t, 1H), 6.90~7.05 (m, 5H) ppm.

Example 3

Preparation of 2-(1-Benzylpiperidin-4-ylamino)-N-(4-phenoxyphenyl)nicotinamide [110]

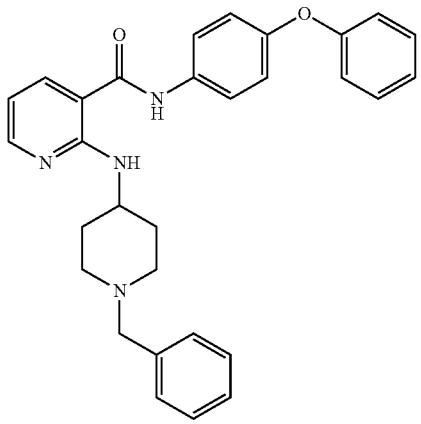 [SMILES: O=C(Nc1ccc(Oc2ccccc2)cc1)c1cccnc1NC1CCN(Cc2ccccc2)CC1]

The title compound was prepared in the same manner as in Example 1, with the exception that 2-chloro-(N-4-phenoxyphenyl)nicotinamide of Preparation Example 6, instead of 2-chloro-(N-3-chlorophenyl)nicotinamide, was used in the same molar amount (Yield: 69.1%). ¹H NMR (DMSO-d₆) δ 10.23 (s, 1H), 8.32 (s, 1H), 8.21 (d, 1H), 8.09 (d, 2H), 7.66 (d, 1H), 7.70 (d, 2H), 7.2~07.45 (m, 6H), 6.95~7.18 (m, 5H), 3.90~4.10 (m, 1H), 3.47 (s, 2H), 2.675~2.80 (m, 2H), 2.05~2.25 (m, 2H), 1.95~2.05 (m, 2H), 1.35~1.60 (m, 2H) ppm.

Example 4

Preparation of 2-(4-Phenoxyanilino)-N-(4-phenoxyphenyl)nicotinamide [111]

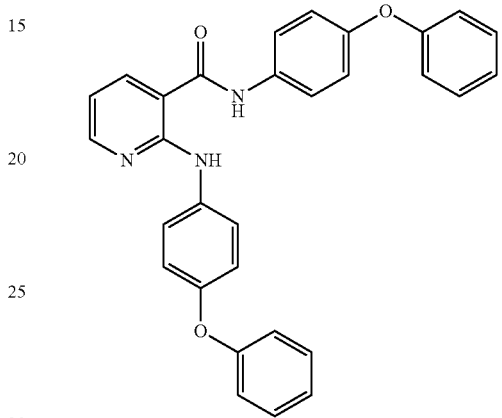

The title compound was prepared in the same manner as in Example 1, with the exception that 2-chloro-(N-4-phenoxyphenyl)nicotinamide of Preparation Example 6, instead of 2-chloro-(N-3-chlorophenyl)nicotinamide, and 4-phenoxyaniline, instead of 4-amino-1-benzylpiperidine, were used in the same molar amounts (Yield: 77.8%). ¹H NMR (DMSO-d₆) δ 10.50 (s, 1H), 10.33 (s, 1H), 8.35 (d, 1H), 8.25 (d, ¹H), 7.69~7.82 (m, 4H), 7.30~7.46 (m, 4H), 6.88~7.18 (m, 11H) ppm.

Example 5

Preparation of N-(3-Chlorophenyl)-2-(2,2,6,6-tetramethylpiperidin-4-ylamino)nicotinamide [201]

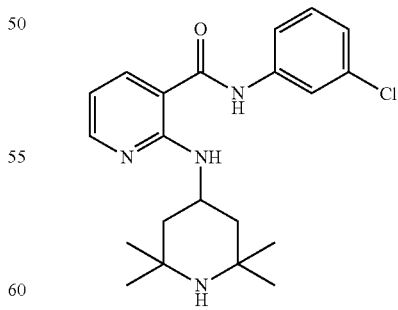

The title compound was prepared in the same manner as in Example 1, with the exception that 4-amino-2,2,6,6-tetramethylpiperidine, instead of 4-amino-1-benzylpiperidine, was used (Yield: 82.1%). ¹H NMR (CDCl₃) δ 8.26 (d, 1H), 7.80 (d, 1H), 7.68-7.63 (m, 2H), 7.35 (d, 1H), 7.28 (t, 1H), 7.13 (d, 1H), 6.56-6.47 (m, 1H), 4.65-4.46 (m, 1H), 2.05 (d, 2H), 1.30 (s, 6H), 1.14 (s, 6H), 1.02 (t, 2H) ppm.

Example 6

Preparation of N-(3-Chlorophenyl)-2-(1-tert-butoxycarbamoylpiperidin-4-ylamino)nicotinamide [208]

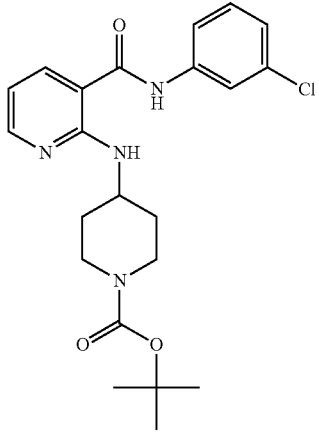 [SMILES: CC(C)(C)OC(=O)N1CCC(Nc2ncccc2C(=O)Nc2cccc(Cl)c2)CC1]

The title compound was prepared in the same manner as in Example 1, with the exception that 4-amino-1-Boc-piperidine, instead of 4-amino-1-benzylpiperidine, was used in the same molar amount (Yield: 42.3%). $^1$H NMR (CDCl$_3$) δ 8.23 (d, 1H), 8.03 (d, 1H), 7.75 (d, 1H), 7.63 (s, 1H), 7.40 (d, 1H), 7.27 (t, 1H), 7.12 (d, 1H), 4.26-4.10 (m, 1H), 3.96 (d, 2H), 2.98 (t, 2H), 1.98 (d, 2H), 1.50-1.36 (m, 11H) ppm.

Example 7

Preparation of 2-(1-Azabicyclo[2.2.2]oct-3-ylamino)-N-(3-chlorophenyl)nicotinamide [210]

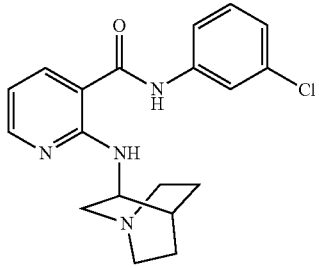 [SMILES: O=C(Nc1cccc(Cl)c1)c1cccnc1NC1CN2CCC1CC2]

The title compound was prepared in the same manner as in Example 1, with the exception that 3-amino-1-azabicyclo[2.2.2]octane, instead of 4-amino-1-benzylpiperidine, was used in the same molar amount (Yield: 24.5%). $^1$H NMR (CDCl$_3$) δ 8.19 (d, 1H), 7.95 (d, 1H), 7.86 (d, 1H), 7.10-7.03 (m, 2H), 6.86-6.79 (m, 1H), 6.58-6.50 (m, 1H), 4.40 (s, 1H), 4.03 (d, 1H), 3.80-3.61 (m, 2H), 3.33 (d, 1H), 3.18-2.95 (m, 2H), 2.47-2.36 (m, 1H), 1.95-1.69 (m, 4H) ppm.

Example 8

Preparation of N-(3-Chlorophenyl)-2-(1-methylpiperidin-4-ylamino)nicotinamide [214]

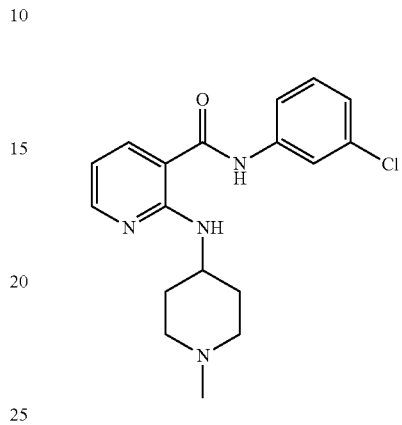

The title compound was prepared in the same manner as in Example 1, with the exception that 4-amino-1-methylpiperidine, instead of 4-amino-1-benzylpiperidine, was used in the same molar amount (Yield: 87.3%). $^1$H NMR (CDCl$_3$) δ 8.26 (d, 1H), 8.01 (d, 1H), 7.75-7.65 (m, 2H), 7.41-7.12 (m, 3H), 6.68-6.62 (m, 1H), 4.16-4.05 (m, 1H), 3.75-3.4 (m, 2H), 2.86 (d, 2H), 2.37 (s, 3H), 2.15-2.05 (m, 2H), 1.76-1.60 (m, 2H) ppm.

Example 9

Preparation of N-(3-Chlorophenyl)-2-[1-(2-hydroxyethyl)piperidin-4-ylamino]nicotinamide [218]

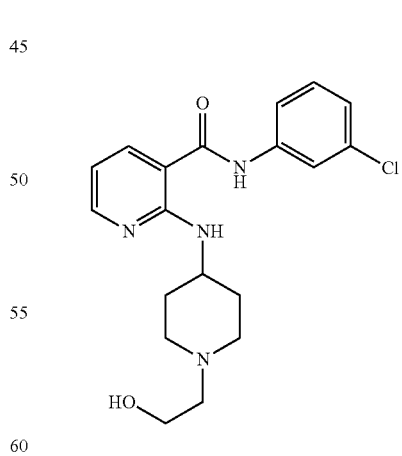

The title compound was prepared in the same manner as in Example 1, with the exception that 4-amino-1-(2-hydroxyethyl)piperidine obtained in Preparation Example 17, instead of 4-amino-1-benzylpiperidine, was used in the same molar amount (Yield: 64.6%). $^1$H NMR (CDCl$_3$) δ 8.18 (d, 1H), 7.96 (d, 1H), 7.74 (d, 1H), 7.61 (s, 1H), 7.47 (d, 1H), 7.22 (t, 1H), 7.06 (d, 1H), 6.48-6.41 (m, 1H), 3.54 (t, 2H), 3.03 (d, 2H), 2.74 (t, 2H), 2.48 (t, 2H), 2.22 (t, 1H), 2.05-1.94 (m, 2H), 1.59-1.35 (m, 2H) ppm.

Example 10

Preparation of N-(3-Chlorophenyl)-2-(4-methylpiperazin-1-ylamino)nicotinamide [240]

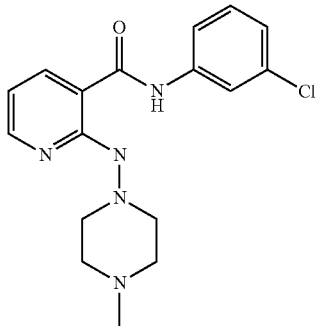 [SMILES: CN1CCN(Nc2ncccc2C(=O)Nc2cccc(Cl)c2)CC1]

The title compound was prepared in the same manner as in Example 1, with the exception that 1-amino-4-methylpiperazine, instead of 4-amino-1-benzylpiperidine, was used in the same molar amount (Yield: 93.8%). $^1$H NMR (CDCl$_3$) δ 8.47-8.37 (m, 2H), 7.93 (s, 1H), 7.51 (d, 1H), 7.28 (t, 1H), 7.21-7.08 (m, 2H), 3.27 (t, 4H), 2.62 (t, 4H), 2.37 (s, 3H) ppm.

Example 11

Preparation of N-(3-Chlorophenyl)-2-[4-(2-hydroxyethyl)piperazin-1-ylamino)nicotinamide [241]

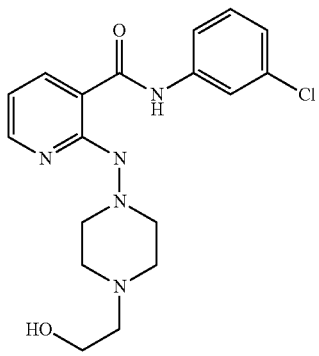 [SMILES: O=C(Nc1cccc(Cl)c1)c1cccnc1NN1CCN(CCO)CC1]

The title compound was prepared in the same manner as in Example 1, with the exception that 1-amino-4-(2-hydroxyethyl)piperazine, instead of 4-amino-1-benzylpiperidine, was used in the same molar amount (Yield: 77.3%). $^1$H NMR (CDCl$_3$) δ 8.47-8.37 (m, 2H), 7.91 (s, 1H), 7.51 (d, 1H), 7.28 (t, 1H), 7.21-7.08 (m, 2H), 3.66 (t, 2H), 3.29 (t, 4H), 2.75 (t, 2H), 2.65 (t, 2H) ppm.

Example 12

Preparation of N-(3-chlorophenyl)-2-(1-tert-butoxycarbamoylpiperidin-3-ylamino)nicotinamide 12-A) Preparation of (R)—N-(3-chlorophenyl)-2-(1-tert-butoxycarbamoylpiperidin-3-ylamino)nicotinamide [270]

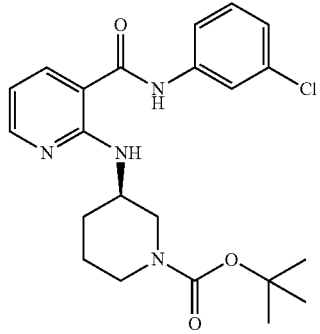 [SMILES: CC(C)(C)OC(=O)N1CCC[C@@H](Nc2ncccc2C(=O)Nc2cccc(Cl)c2)C1]

The title compound was prepared in the same manner as in Example 1, with the exception that (R)-3-amino-1-Boc-piperidine, instead of 4-amino-1-benzylpiperidine, was used in the same molar amount (Yield: 43.8%). $^1$H NMR (CDCl$_3$) δ 8.24 (br, 2H), 8.08 (d, 1H), 7.78 (d, 1H), 7.70 (s, 1H), 7.39 (d, 1H), 7.25 (t, 1H), 7.12 (d, 1H), 6.57-6.51 (m, 1H), 4.21-4.06 (m, 1H), 3.95-3.86 (m, 1H), 3.62-3.49 (m, 2H), 3.30-3.18 (m, 2H), 2.04-1.86 (m, 1H), 1.68-1.56 (m, 2H), 1.42 (s, 9H) ppm.

12-B) Preparation of (S)—N-(3-chlorophenyl)-2-(1-tert-butoxycarbamoylpiperidin-3-ylamino)nicotinamide [276]

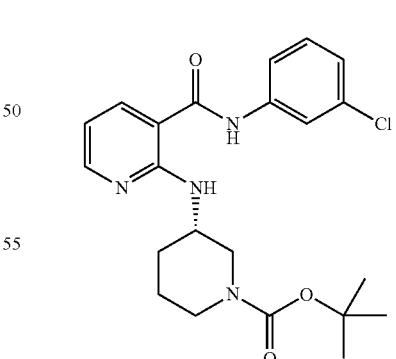

The title compound was prepared in the same manner as in Example 1, with the exception that (S)-3-amino-1-Boc-piperidine, instead of 4-amino-1-benzylpiperidine, was used in the same molar amount (Yield: 51.7%). $^1$H NMR (CDCl$_3$) δ 8.24 (d, 1H), 8.08 (d, 1H), 7.71 (d, 1H), 7.69 (s, 1H), 7.16 (d, 1H), 7.27 (t, 1H), 7.12 (d, 1H), 6.59-6.51 (m, 1H), 4.21-4.06

(m, 1H), 3.95-3.86 (m, 1H), 3.62-3.52 (m, 1H), 3.30-3.18 (m, 2H), 2.04-1.96 (m, 1H), 1.98-1.56 (m, 3H), 1.42 (s, 9H) ppm.

Example 13

Preparation of 2-(1-Benzylpiperidin-4-ylamino)-6-chloro-N-(3-chlorophenyl)nicotinamide [301]

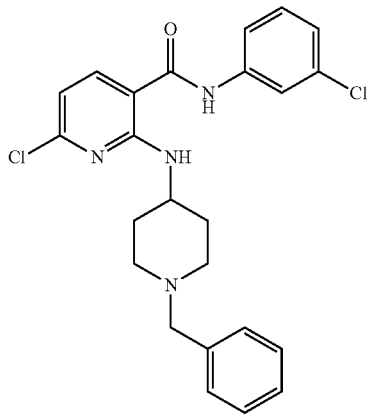 [SMILES: O=C(Nc1cccc(Cl)c1)c1ccc(Cl)nc1NC1CCN(Cc2ccccc2)CC1]

The title compound was prepared in the same manner as in Example 1, with the exception that 2,6-dichloro-N-(3-chlorophenyl)nicotinamide obtained in Preparation Example 8, instead of 2-chloro-N-(3-chlorophenyl)nicotinamide, was used in the same molar amount (Yield: 48.7%). $^1$H NMR (CDCl$_3$) δ 8.21 (d, 1H), 7.75 (s, 1H), 7.64 (s, 1H), 7.60 (d, 1H), 7.39-7.25 (m, 6H), 7.14 (d, 1H), 4.15-3.98 (m, 1H), 3.53 (s, 2H), 2.79 (d, 2H), 2.21 (t, 2H), 2.06-1.93 (m, 2H), 1.67-1.48 (m, 2H) ppm.

Example 14

Preparation of 2-(1-Benzylpiperidin-4-ylamino)-6-chloro-N-(3-chlorophenyl)-5-fluoronicotinamide

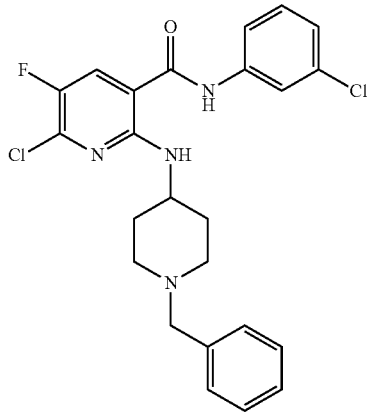 [SMILES: O=C(Nc1cccc(Cl)c1)c1cc(F)c(Cl)nc1NC1CCN(Cc2ccccc2)CC1]

The title compound was prepared in the same manner as in Example 1, with the exception that 2,6-dichloro-N-(3-chlorophenyl)-5-fluoronicotinamide obtained in Preparation Example 9, instead of 2-chloro-N-(3-chlorophenyl)nicotinamide, was used in the same molar amount (Yield: 66.6%). $^1$H NMR (CDCl$_3$) δ 8.73 (s, 1H), 7.88 (d, 1H), 7.76 (s, 1H), 7.48 (d, 1H), 7.27 (t, 1H), 7.12 (d, 1H), 4.96 (d, 1H), 4.02 (m, 1H), 3.56 (s, 2H), 2.89 (d, 2H), 2.22 (t, 2H), 2.09 (d, 2H), 1.59 (m, 2H) ppm.

Example 15

Preparation of 6-Chloro-N-(3-chlorophenyl)-2-[1-(2-hydroxyethyl)benzylpiperidin-4-ylamino]nicotinamide

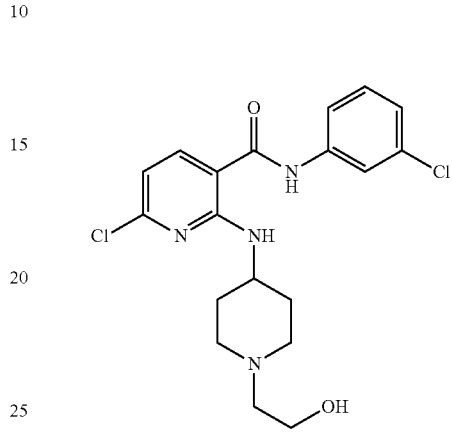

The title compound was prepared in the same manner as in Example 13, with the exception that 4-amino-1-(2-hydroxyethyl)piperidine obtained in Preparation Example 17, instead of 4-amino-1-benzylpiperidine, was used in the same molar amount. (Yield: 74.5%). $^1$H NMR (CDCl$_3$) δ 8.32 (d, 1H), 7.78 (d, 1H), 7.67 (s, 1H), 7.41 (d, 1H), 7.27 (t, 1H), 7.13 (d, 1H), 6.53 (d, 1H), 4.17-4.08 (m, 1H), 3.74 (t, 2H), 3.12 (d, 2H), 2.78 (t, 2H), 2.61 (t, 2H), 2.12 (d, 2H), 1.88-1.68 (m, 2H) ppm.

Example 16

Preparation of 6-chloro-N-(3-chlorophenyl)-5-fluoro-2-[1-(2-hydroxyethyl)piperidin-4-ylamino]nicotinamide [312]

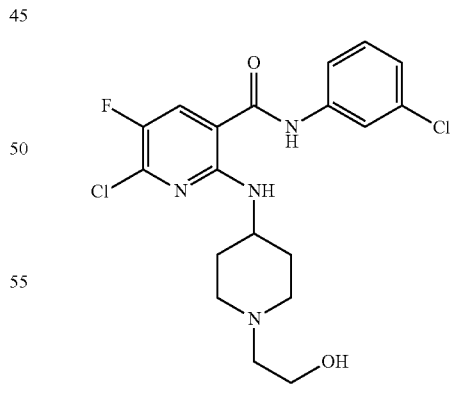

The title compound was prepared in the same manner as in Example 1, with the exception that 2,6-dichloro-N-(3-chlorophenyl)-5-fluoronicotinamide obtained in Preparation Example 9, instead of 2-chloro-N-(3-chlorophenyl)nicotinamide, and 4-amino-1-(2-hydroxyethyl)piperidine obtained in Preparation Example 17, instead of 4-amino-1-benzylpiperidine, were used in the same molar amounts (Yield: 81.1%).

$^1$H NMR (CDCl3) δ 8.73 (s, 1H), 7.88 (d, 1H), 7.76 (s, 1H), 7.48 (d, 1H), 7.29 (t, 1H), 7.12 (d, 1H), 4.98 (d, 1H), 4.04 (m, 1H), 3.62 (t, 2H), 2.92 (d, 2H), 2.59 (t, 2H), 2.32 (t, 2H), 2.12 (d, 2H), 1.62 (m, 2H) ppm.

Example 17

Preparation of 2-(1-Benzylpiperidin-4-ylamino)-N-(3,3-dimethyl-2,3-dihydro-1H-indol-6-yl)nicotinamide [117]

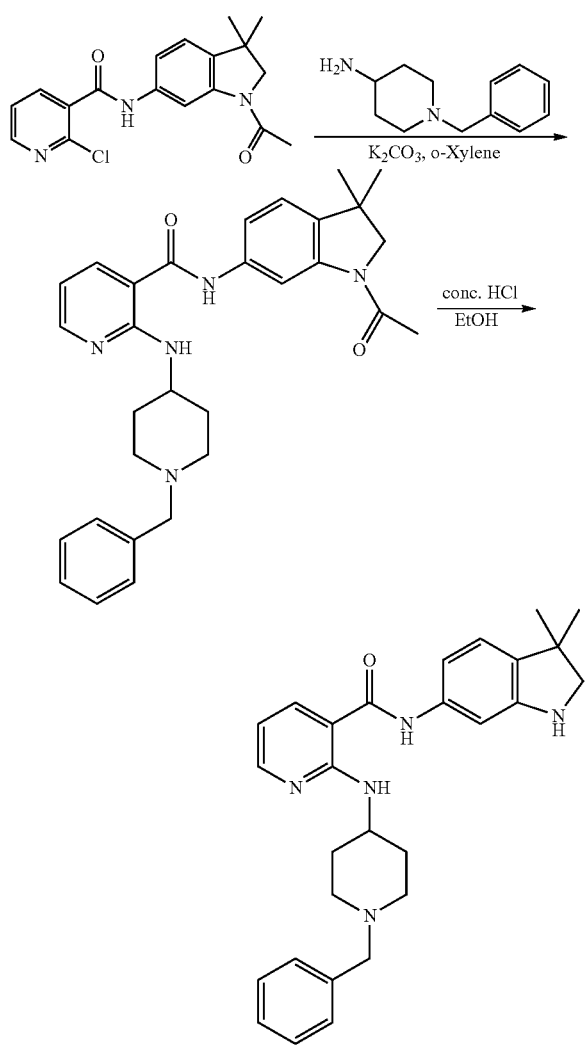

Step 1. Preparation of N-(1-acetyl-3,3-dimethyl-2,3-dihydro-1H-indol-6-yl)-2-(1-benzylpiperidin-4-ylamino)nicotinamide A solution of N-(1-acetyl-3,3-dimethyl-2,3-dihydro-1H-indol-6-yl)-2-chloronicotinamide (361 mg, 1.05 mmol, 1.05 eq), prepared in Preparation Example 7, 4-amino-1-benzylpiperidine (1.0 mmol), and anhydrous potassium carbonate (1.3 mmol) in ortho-xylene was stirred for 24 hrs under reflux. The reaction mixture was cooled to a room temperature, concentrated in a reduced pressure, and immediately used in the next step without further purification.

Step 2. Preparation of 2-(1-benzylpiperidin-4-ylamino)-N-(3,3-dimethyl-2,3-dihydro-1H-indol-6-yl)nicotinamide The residue obtained in step 1 was placed in 10 ml of ethanol and conc. HCl aqueous solution (excess) and stirred for 4 hrs under reflux. The reaction mixture was cooled to a room temperature, and concentrated in a reduced pressure to remove the solvent. The residue was dissolved in 10 ml of distilled water, and adjusted to a pH of 9~10 by dropwise adding a 20 (wt/wt) % sodium hydroxide aqueous solution. This mixture was extracted with 20 ml of chloroform, dried over sodium sulfate to remove water, and concentrated in a reduced pressure. Purification through column chromatography (mobile phase: 10 (v/v) % acetone in chloroform) afforded the title compound. (Total yield: 46.1%) $^1$H NMR (CDCl3), δ 8.21 (d, 1H), 7.97 (d, 1H), 7.64 (d, 1H), 7.20-7.40 (m, 4H), 6.99 (d, 2H), 6.67 (d, 1H), 6.49 (dd, 1H), 4.06 (bs, 1H), 3.52 (s, 2H), 3.32 (s, 2H), 2.85 (d, 2H), 2.25 (t, 2H), 1.95-2.10 (m, 2H), 1.48-1.72 (m, 2H), 1.29 (s, 6H) ppm.

Example 18

Preparation of N-(3,3-Dimethyl-2,3-dihydro-1H-indol-6-yl)-2-(4-phenoxyanilino)nicotinamide [118]

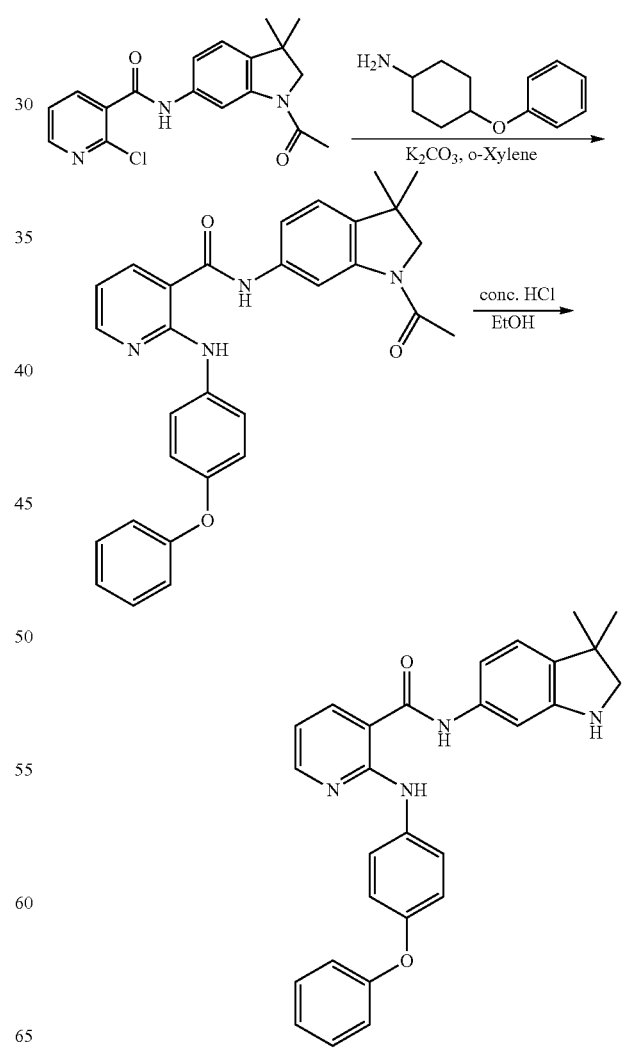

The title compound was prepared in the same manner as in steps 1 and 2 of Example 17, with the exception that 4-phenoxyaniline, instead of 4-amino-1-benzylpiperidine, was used in the same molar amount (Total yield: 54.3%). ¹H NMR (CDCl₃), δ 10.20 (s, 1H), 8.32 (d, 1H), 7.78 (d, 1H), 7.72 (s, 1H), 7.62 (d, 3H), 7.31 (t, 3H), 6.95-7.11 (m, 5H), 6.68-6.85 (m, 1H), 3.34 (s, 2H), 1.32 (s, 6H) ppm.

Example 19

Preparation of N-(3-chlorophenyl)-2-(4-piperidylamino)nicotinamide [224]

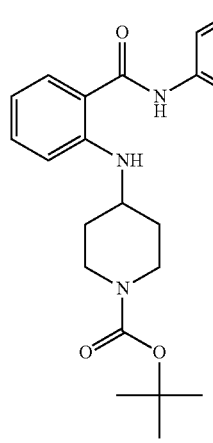

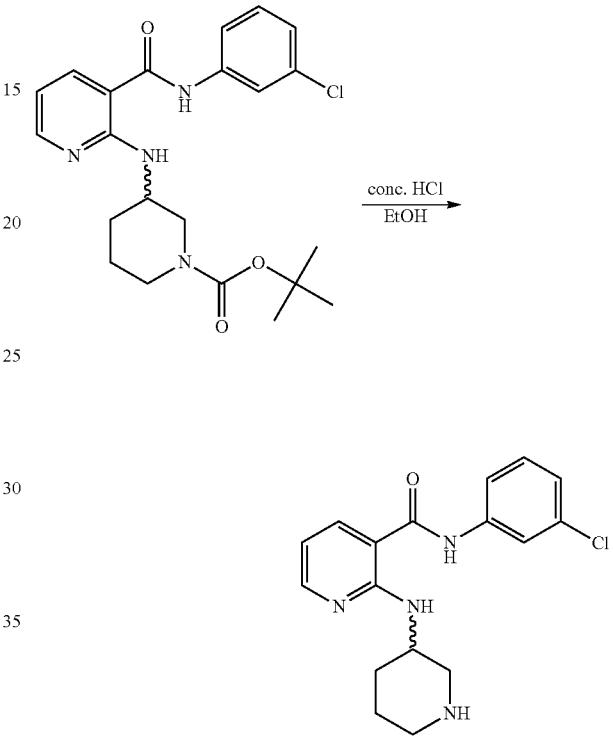

A solution of 1.0 g of N-(3-chlorophenyl)-2-(1-tert-butoxycarbamoylpiperidin-4-ylamino)nicotinamide obtained in Example 6, in 10 ml of ethanol was mixed with 5 ml of a conc. HCl aqueous solution and stirred for 8 hrs under reflux. The reaction solution was cooled to a room temperature, concentrated in a reduced pressure to remove the solvent, and adjusted to a pH of 9~10 by dropwise adding saturated sodium hydrogen carbonate aqueous solution. After three rounds of extraction with 30 ml of ethylacetate per round, the extracts were dried over a desiccant to remove water, and concentrated in a reduced pressure and dried in vacuum to afford 0.69 g of the title compound (Yield: 89.9%). ¹H NMR (CDCl₃) δ 8.23 (d, 1H), 7.99 (d, 2H), 7.7 (d, 1H), 7.66 (s, 1H), 7.36 (d, 1H), 7.27 (t, 1H), 7.10 (d, 1H), 6.53-5.45 (m, 1H), 4.18-4.05 (m, 1H), 3.43 (t, 1H), 3.09 (d, 2H), 2.74 (t, 2H), 2.15-2.01 (m, 2H), 1.57-1.36 (m, 2H) ppm.

Example 20

Preparation of N-(3-Chlorophenyl)-2-(3-piperidylamino)nicotinamide

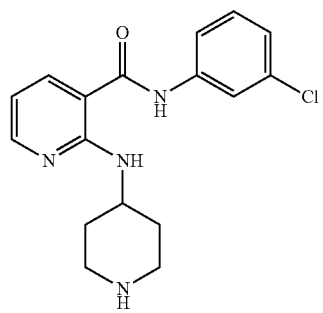

20-A) Preparation of (R)—N-(3-chlorophenyl)-2-(3-piperidylamino)nicotinamide [269]

The title compound was prepared in the same manner as in steps of Example 19 with the exception that 0.5 g of (R)—N-(3-chlorophenyl)-2-(1-tert-butoxycarbamoylpiperidin-3-ylamino)nicotinamide prepared in Example 12-A as a starting material to afford 0.35 g of the title compound (Yield: 91.2%). ¹H NMR 8.26 (d, 1H), 8.08 (d, 1H), 7.72 (d, 1H), 7.67 (s, 1H), 7.37 (d, 1H), 7.26 (t, 1H), 7.11 (d, 1H), 6.57-6.51 (m, 1H), 4.18-4.08 (m, 1H), 3.72 (br, 1H), 3.21 (d, 1H), 2.97-2.88 (m, 1H), 2.79-2.60 (m, 2H), 2.14-1.96 (m, 2H), 1.82-1.68 (m, 1H), 1.66-1.48 (m, 2H) ppm.

20-B) Preparation of (S)—N-(3-chlorophenyl)-2-(3-piperidylamino)nicotinamide [275]

The title compound was prepared in the same manner as in steps of Example 19 with the exception that 0.5 g of (S)—N-(3-chlorophenyl)-2-(1-tert-butoxycarbamoylpiperidin-3-ylamino)nicotinamide prepared in Example 12-B as a starting material to afford 0.34 g of the title compound (Yield: 88.6%). ¹H NMR 8.22 (d, 1H), 8.03 (d, 1H), 7.71 (d, 1H), 7.67 (s, 1H), 7.37 (d, 1H), 7.26 (t, 1H), 7.11 (d, 1H), 6.52-6.46 (m, 1H), 4.18-4.08 (m, 1H), 3.17 (d, 1H), 2.95 (m, 1H), 2.74-2.53 (m, 2H), 2.14-1.96 (m, 2H), 1.82-1.68 (m, 1H), 1.66-1.48 (m, 2H) ppm.

Example 21

Preparation of N-(3-Chlorophenyl)-2-(1-(2-hydroxyethyl)-2,2,6,6-tetramethylpiperidin-4-ylamino)nicotinamide [242]

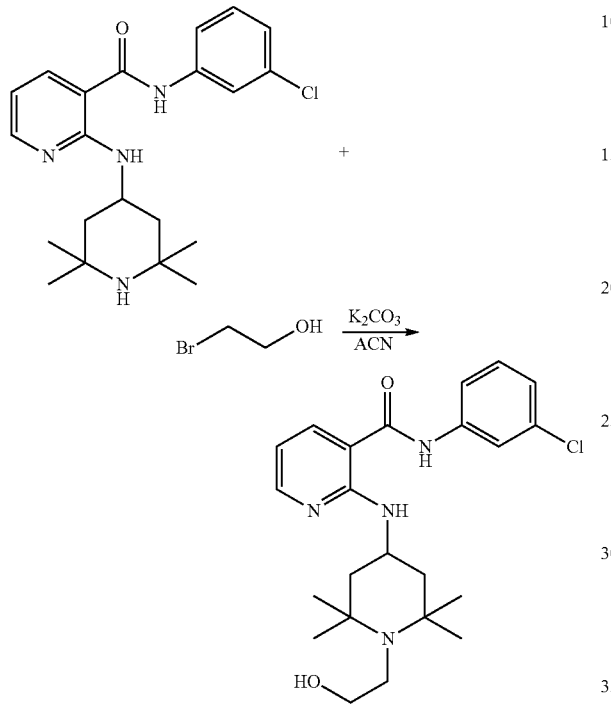

A solution of N-(3-chlorophenyl)-2-(2,2,6,6-tetramethylpiperidin-4-ylamino)nicotinamide (330 mg, 1 mmol, 1 eq), 2-bromoethanol (1.2 mmol), and anhydrous potassium carbonate (1.2 mmol) in 5 ml of acetonitrile was stirred for 18 hrs under reflux. The reaction mixture was cooled to a room temperature and filtered. The filtrate was concentrated in a reduced pressure. Silica gel column chromatography (mobile phase: 10 (v/v) % methanol in chloroform) afforded the title compound. Yield: 37.1% $^1$H NMR (CDCl$_3$) δ 8.22 (d, 1H), 7.79 (d, 1H), 7.69 (d, 1H), 7.65 (s, 1H), 7.37 (d, 1H), 7.27 (t, 1H), 7.10 (d, 1H), 6.51-6.45 (m, 1H), 4.64-4.45 (m, 1H), 3.88 (t, 2H), 3.49 (t, 2H), 2.08-1.96 (m, 3H), 1.28 (s, 6H), 1.13 (s, 6H), 1.0 (t, 2H) ppm.

Example 22

Preparation of 2-(1-Arylpiperidin-4-ylamino)-N-(3-chlorophenyl) nicotinamide [243]

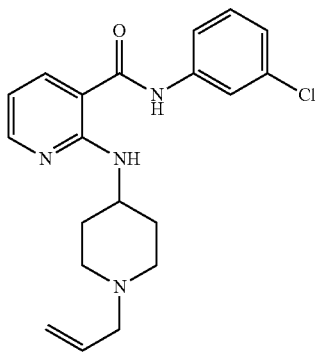 [SMILES: C=CCN1CCC(Nc2ncccc2C(=O)Nc2cccc(Cl)c2)CC1]

The title compound was prepared in the same manner as in Example 21, with the exception that N-(3-chlorophenyl)-2-(4-piperidylamino)nicotinamide of Example 19, instead of N-(3-chlorophenyl)-2-(2,2,6,6-tetramethylpiperidin-4-ylamino)nicotinamide, and arylbromide, instead of 2-bromoethanol, were used in the same molar amounts (Yield: 36.8%). $^1$H NMR (CD$_3$OD) δ 8.22 (d, 1H), 8.08 (d, 1H), 7.86 (s, 1H), 7.53 (d, 1H), 7.34 (t, 1H), 7.15 (d, 1H), 6.76-6.68 (m, 1H), 5.79 (t, 1H), 4.72-4.62 (m, 2H), 4.33-4.20 (m, 1H), 4.07 (dd, 1H), 3.58-3.4 (m, 3H), 3.19 (t, 2H), 2.32 (d, 2H), 1.89-1.68 (m, 2H) ppm.

Example 23

Preparation of N-(3-chlorophenyl)-2-[1-(2-N,N-diethylamino-ethyl)piperidin-4-ylamino]nicotinamide [244]

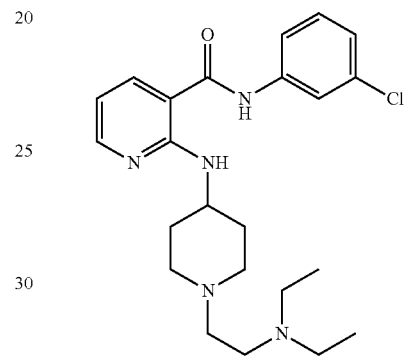

The title compound was prepared in the same manner as in Example 22, with the exception that 2-chloroethyl-N,N-diethylamine, instead of arylbromide, was used in the same molar amount (Yield: 47.5%). $^1$H NMR (CDCl$_3$) δ 8.19 (d, 1H), 8.06 (s, 1H), 7.93 (d, 1H), 7.65 (d, 1H), 7.59 (s, 1H), 7.33 (d, 1H), 7.21 (s, 1H), 7.06 (d, 1H), 6.48-6.40 (m, 1H), 4.07-3.93 (m, 1H), 2.79 (d, 2H), 2.59-2.40 (m, 8H), 2.18 (t, 2H), 1.98 (d, 2H), 1.62-1.46 (m, 2H), 0.97 (t, 6H) ppm.

Example 24

Preparation of N-(3-Chlorophenyl)-2-[1-(pyridin-2-ylmethyl)piperidin-4-ylamino]nicotinamide [248]

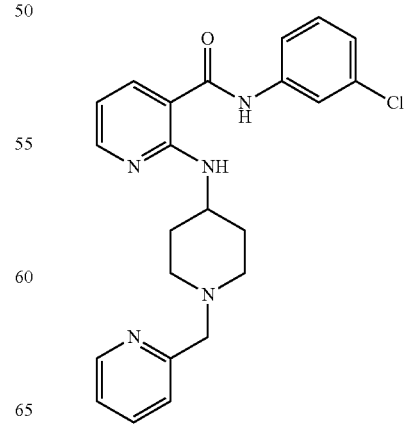

The title compound was prepared in the same manner as in Example 22, with the exception that 2-chloromethylpyridine, instead of arylbromide, was used in the same molar amount (Yield: 56.6%). $^1$H NMR (CD$_3$OD) δ 8.49 (d, 1H), 8.26 (d, 1H), 8.02 (d, 1H), 7.89-7.80 (m, 2H), 7.59-7.52 (m, 2H), 7.37-7.31 (m, 2H), 7.14 (d, 1H), 6.68-6.60 (m, 1H), 4.09-3.97 (m, 1H), 3.71 (s, 2H), 2.88 (d, 2H), 2.39 (t, 2H), 2.12-2.01 (m, 2H), 1.73-1.57 (m, 2H) ppm.

Example 25

Preparation of N-(3-chlorophenyl)-2-[1-(pyridin-3-ylmethyl)piperidin-4-ylamino]nicotinamide [249]

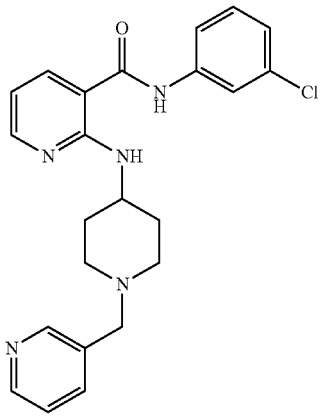 [SMILES: O=C(Nc1cccc(Cl)c1)c1cccnc1NC1CCN(Cc2cccnc2)CC1]

The title compound was prepared in the same manner as in Example 22, with the exception that 3-chloromethylpyridine, instead of arylbromide, was used in the same molar amount (Yield: 43.8%). $^1$H NMR (CDCl$_3$) δ 8.49 (m, 1H), 8.26 (d, 1H), 7.99 (d, 1H), 7.77-7.65 (m, 3H), 7.41-7.25 (m, 3H), 7.17-7.11 (m, 1H), 6.55-6.49 (m, 1H), 4.23-4.08 (m, 1H), 3.10 (d, 2H), 2.76 (d, 2H), 2.06 (m, 2H), 1.68 (s, 2H), 1.43 (q, 2H) ppm.

Example 26

Preparation of 2-{1-[1-(6-chloro-5-fluoropyrimidin-4-yl)ethyl]piperidin-4-ylamino}-N-(3-chlorophenyl)nicotinamide [250]

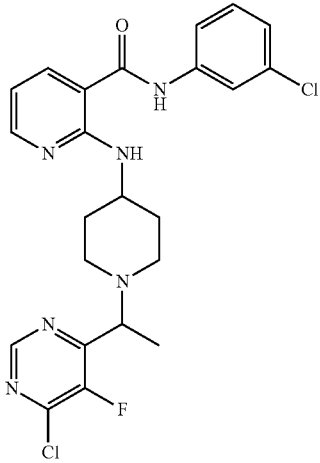

The title compound was prepared in the same manner as in Example 22, with the exception that 4-(1-bromoethyl)-6-chloro-5-fluoropyrimidine prepared in Preparation Example 19, instead of arylbromide, was used in the same molar amount (Yield: 44.9%). $^1$H NMR (CDCl$_3$) δ 8.22 (d, 1H), 8.18 (s, 1H), 8.06 (d, 1H), 7.72 (d, 1H), 7.61 (s, 1H), 7.33 (d, 1H), 7.22 (t, 1H), 7.08 (d, 1H), 6.55-6.47 (m, 1H), 5.34 (q, 1H), 4.43-4.23 (m, 3H), 3.28 (t, 2H), 2.13 (d, 2H), 1.98 (d, 3H), 1.67-1.46 (m, 2H) ppm.

Example 27

Preparation of N-(3-chlorophenyl)-2-[1-(2-hydroxyethyl)piperidin-3-ylamino]nicotinamide 27-A) Preparation of (R)—N-(3-chlorophenyl)-2-[1-(2-hydroxyethyl)piperidin-3-ylamino]nicotinamide [268]

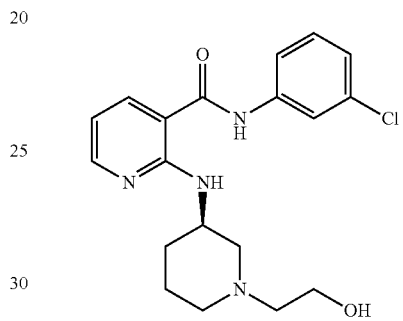

The title compound was prepared in the same manner as in Example 21, with the exception that (R)—N-(3-chlorophenyl)-2-(3-piperidylamino)nicotinamide of Example 20-A, instead of N-(3-chlorophenyl)-2-(2,2,6,6-tetramethylpiperidin-4-ylamino)nicotinamide, was used in the same molar amount (Yield: 64.7%). $^1$H NMR (CDCl$_3$) δ 8.48 (br, 1H), 8.40 (s, 1H), 8.17 (d, 1H), 7.76 (d, 1H), 7.59 (s, 1H), 7.42 (d, 1H), 7.19 (t, 1H), 7.03 (d, 1H), 6.48-6.40 (m, 1H), 4.35-4.23 (m, 1H), 3.61 (t, 2H), 3.13 (br, 2H), 2.69 (d, 1H), 2.60-2.36 (m, 4H), 1.85-1.58 (m, 3H) ppm.

27-B) Preparation of (S)—N-(3-chlorophenyl)-2-[1-(2-hydroxyethyl)piperidin-3-ylamino]nicotinamide [274]

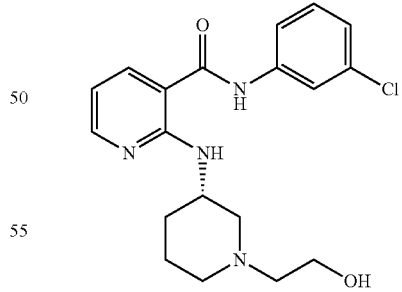

The title compound was prepared in the same manner as in Example 21, with the exception that (S)—N-(3-chlorophenyl)-2-(3-piperidylamino)nicotinamide of Example 20-B, instead of N-(3-chlorophenyl)-2-(2,2,6,6-tetramethylpiperidin-4-ylamino)nicotinamide, was used in the same molar amount (Yield: 60.8%). $^1$H NMR (CDCl$_3$) δ 8.50 (br, 1H), 8.22 (d, 1H), 7.97 (s, 1H), 7.73 (d, 1H), 7.61 (s, 1H), 7.45 (d, 1H), 7.25 (t, 1H), 7.09 (d, 1H), 6.53-6.47 (m, 1H), 4.33 (br, 1H), 3.61 (t, 2H), 2.76-2.45 (m, 6H), 1.85-1.58 (m, 4H) ppm.

Example 28

Preparation of 2-(1-benzylpiperidin-3-ylamino)-N-(3-chlorophenyl)nicotinamide 28-A) Preparation of (R)-2-(1-benzylpiperidin-3-ylamino)-N-(3-chlorophenyl)nicotinamide [267]

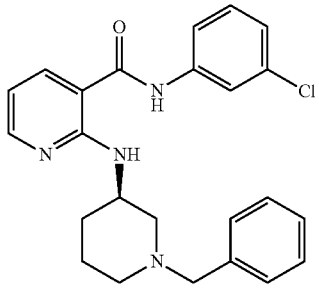 [SMILES: O=C(Nc1cccc(Cl)c1)c1cccnc1N[C@@H]1CCCN(Cc2ccccc2)C1]

The title compound was prepared in the same manner as in Example 21, with the exception that (S)—N-(3-chlorophenyl)-2-(3-piperidylamino)nicotinamide of Example 20-A, instead of N-(3-chlorophenyl)-2-(2,2,6,6-tetramethylpiperidin-4-ylamino)nicotinamide, and benzylchloride, instead of 2-bromoethanol, were used in the same molar amounts (Yield: 64.4%). ¹H NMR (CDCl₃) δ 8.33 (d, 1H), 8.24 (d, 1H), 7.83 (s, 1H), 7.74 (s, 1H), 7.68 (d, 1H), 7.47-7.13 (m, 7H), 6.53-6.46 (m, 1H), 4.39-4.27 (m, 1H), 2.69 (d, 1H), 2.53-2.34 (m, 3H), 1.85-1.58 (m, 6H) ppm.

28-B) Preparation of (S)-2-(1-benzylpiperidin-3-ylamino)-N-(3-chlorophenyl)nicotinamide [273]

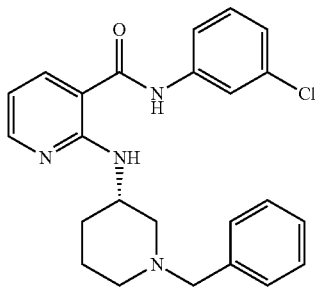 [SMILES: O=C(Nc1cccc(Cl)c1)c1cccnc1N[C@H]1CCCN(Cc2ccccc2)C1]

The title compound was prepared in the same manner as in Example 21, with the exception that (S)—N-(3-chlorophenyl)-2-(3-piperidylamino)nicotinamide of Example 20-B, instead of N-(3-chlorophenyl)-2-(2,2,6,6-tetramethylpiperidin-4-ylamino)nicotinamide, and benzylchloride, instead of 2-bromoethanol, were used in the same molar amounts (Yield: 68.2%).

¹H NMR (CDCl₃) δ 8.33 (d, 1H), 8.22 (d, 1H), 7.86 (s, 1H), 7.82 (s, 1H), 7.71 (d, 1H), 7.45-7.12 (m, 7H), 6.53-6.46 (m, 1H), 4.32 (br, 1H), 2.68 (d, 1H), 2.53-2.34 (m, 3H), 1.97 (s, 2H), 1.81-1.55 (m, 4H) ppm.

Example 29

Preparation of 2-(4-(3-(3-Chlorophenylcarbamoyl)pyridin-2-ylamino)piperidin-1-yl)maloic acid [246]

Step 1. Preparation of diethyl 2-(4-(3-(3-chlorophenylcarbamoyl)pyridin-2-ylamino)piperidin-1-yl)malonate A solution of 0.25 g of N-(3-chlorophenyl)-2-(4-piperidylamino)nicotinamide obtained in Example 19, 0.2 ml of diethyl 2-bromomalonate, and 0.16 g of anhydrous potassium carbonate in 5 ml of acetonitrile was stirred for 24 hrs under reflux. The reaction mixture was cooled to a room temperature, mixed with 10 ml of ethylacetate, and extracted three times with 1N aqueous HCl solution. The aqueous layer thus obtained was washed again with 15 ml of ethylacetate, adjusted to a pH of about 9 with saturated sodium hydrogen carbonate aqueous solution, and used in the next step without further purification.

Step 2. Preparation of 2-(4-(3-(3-chlorophenylcarbamoyl)pyridin-2-ylamino)piperidin-1-yl)malonic acid The mixture obtained in step 1 was added with 0.16 g of sodium hydroxide, and heated at 50° C. for 3 hrs while stirring. The reaction mixture was cooled to a room temperature, and extracted three times with 10 ml of ethyl acetate. After two rounds of extraction with saturated saline, water was removed using a desiccant. The resulting solution was concentrated in a reduced pressure and purified by silica gel chromatography (mobile phase: 30 (v/v) % hexane in EA) to afford 0.05 g of the title compound (Total yield: 15%). $^1$H NMR (CDCl$_3$+4 drops CD$_3$OD) δ 8.12 (d, 1H) 7.80 (d, 1H), 7.63 (s, 1H), 7.4 (d, 1H), 7.22 (t, 1H), 7.05 (d, 1H), 6.53-6.47 (m, 1H), 4.12-3.98 (m, 1H), 3.10-3.0 (m, 2H), 2.71 (t, 2H), 2.03 (d, 2H), 1.99 (s, 1H), 1.49-1.3 (m, 2H) ppm.

Example 30

Preparation of 2-(1-Benzylpiperidin-4-yloxy)-N-(3-chlorophenyl)nicotinamide [289]

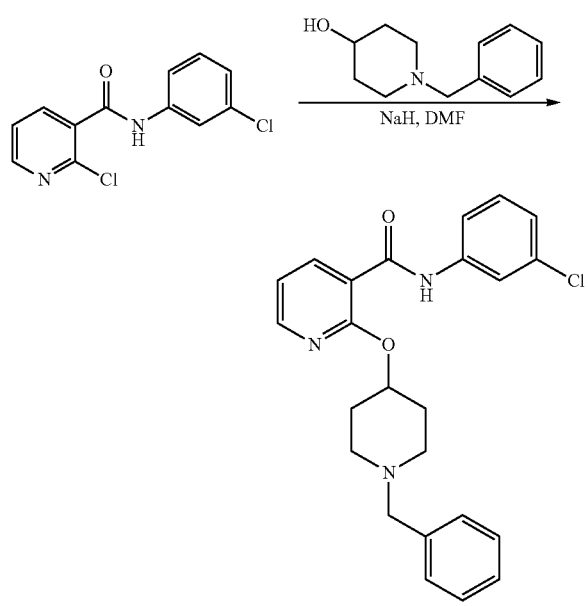

A solution of 1-benzyl-4-hydroxypiperidine (209 mg, 1.1 mmol, 1.1 eq) and 95 w % sodium hydride (1.2 mmol) in 5 ml of dimethylformamide was stirred at a room temperature for 30 min, mixed with 2-chloro-N-(3-chlorophenyl)nicotinamide (1.0 mmol), and stirred for 20 hrs under reflux. The reaction mixture was cooled to a room temperature, and added with 20 ml of pure water to terminate the reaction. After two rounds of extraction with 20 ml of ethylacetate per round, water was removed with a desiccant and the resulting product was concentrated under reduced pressure. Then, the residue obtained by the concentration was subjected to silica gel column chromatography (mobile phase: 30 (v/v) % hexane in EA) to obtain the desired fraction. The desired fraction was dried in a reduced pressure to afford 0.25 g of the title compound (Yield: 33.7%). $^1$H NMR (CDCl$_3$) δ 8.60 (d, 1H), 8.29 (d, 1H), 7.88 (s, 1H), 7.48 (d, 1H), 7.36-7.27 (m, 6H), 7.17-7.05 (m, 2H), 5.51-5.38 (m, 1H), 3.59 (s, 2H), 2.89-2.80 (m, 2H), 2.42 (t, 2H), 2.29-2.23 (m, 2H), 2.06-1.87 (m, 2H) ppm.

Example 31

Preparation of 2-(1-Benzylpiperidin-4-ylsulfanyl)-N-(3-chlorophenyl)nicotinamide [290]

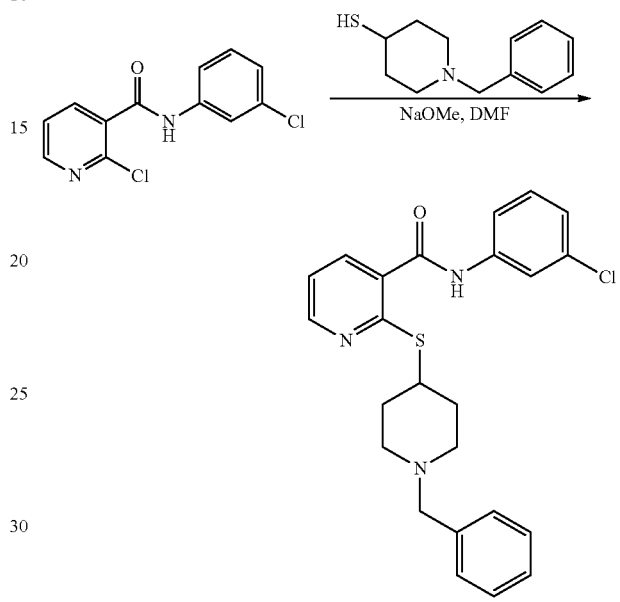

The title compound was prepared in the same manner as in Example 30, with the exception that 1-benzyl-4-mercaptopiperidine, instead of 1-benzyl-4-hydroxypiperidine, was used in the same molar amount while sodium methoxide serving as a base. Yield: 42.8%, $^1$H NMR (CDCl$_3$) δ 8.52-8.46 (m, 2H), 7.88 (d, 1H), 7.46 (d, 1H), 7.32-7.25 (m, 6H), 7.18, 7.02 (m, 2H), 4.08-3.96 (m, 1H), 2.52 (s, 2H), 2.88-2.82 (m, 2H), 2.25 (t, 2H), 2.16-1.97 (m, 2H), 1.88-1.68 (m, 2H)

Example 32

Preparation of 2-(1-Benzylpiperidin-4-ylamino)-N-[4-(4-fluorobenzyl)morpholin-2-ylmethyl]nicotinamide [404]

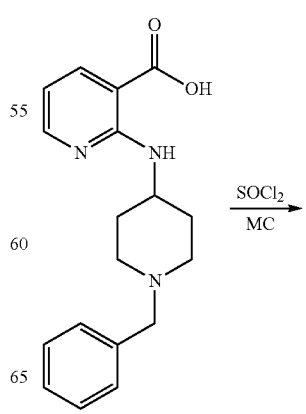

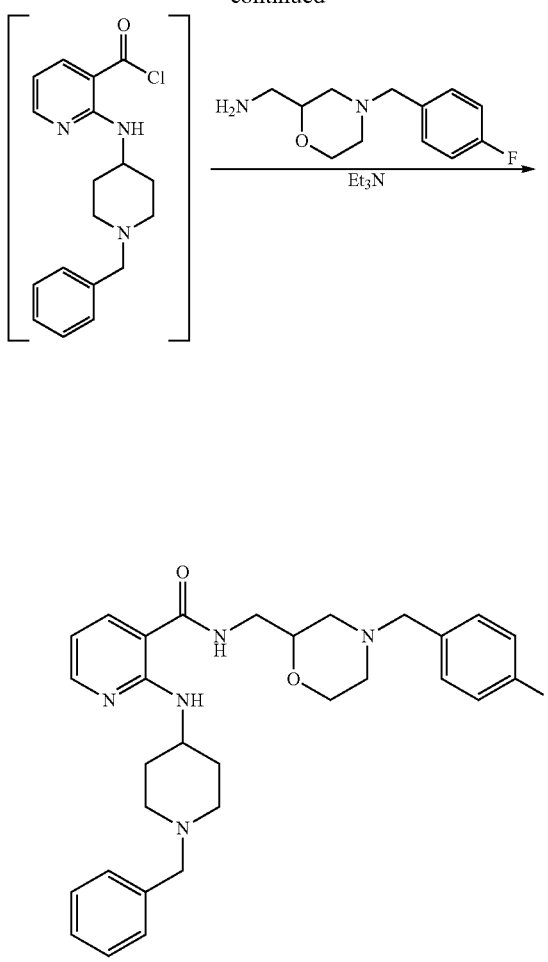

Step 1: Preparation of 2-(1-benzylpiperidin-4-ylamino) nicotinyl chloride

A solution of 2-(1-benzylpiperidin-4-ylamino)nicotinic acid (311 mg, 1.0 mmol, 1.0 eq) prepared in Preparation Example 16, and thionyl chloride (1.5 mmol) in 5 ml of methylene chloride was stirred for 1 hr under reflux. The reaction mixture was cooled to room temperature and immediately used in the next step without further purification.

Step 2: Preparation of 2-(1-benzylpiperidin-4-ylamino)-N-[4-(4-fluorobenzyl)morpholin-2-ylmethyl]nicotinamide The solution obtained in step 1 was cooled to 4-5° C. in an ice bath, followed by dropwise adding triethylamine (0.42 ml, 3.0 mmol) for 5 min. To the reaction solution was added with 4-(4-fluorobenzyl)morpholin-2-ylmethylamine (1.2 mmol), and stirred for 30 min at a room temperature and then for an additional 4 hrs under reflux. The reaction mixture was cooled to a room temperature, and washed with saturated aqueous sodium hydrogen carbonate solution and then with saturated saline. After water was removed with a desiccant, the resulting solution was concentrated in a reduced pressure. In order to obtain a desired fraction, the residue was subjected to silica column chromatography (mobile phase: 30 (v/v) % Hexane in EA) to afford the title compound (Total yield: 53.0%) $^1$H NMR (CDCl$_3$) δ 8.20 (d, 1H), 8.12 (d, 1H), 7.54 (d, 1H), 7.36-7.24 (m, 7H), 7.01 (t, 2H), 6.46-6.38 (m, 1H), 4.08-3.98 (m, 1H), 3.87 (d, 1H), 3.73-3.61 (m, 4H), 3.53 (s, 2H), 3.45 (s, 2H), 3.32-3.19 (m, 2H), 2.85-2.61 (m, 4H), 2.32-2.14 (m, 3H), 2.08-1.88 (m, 3H) ppm.

Example 33

Preparation of 2-(1-benzylpiperidin-4-ylamino)-N-(1,3,4-triazol-2-yl)nicotinamide [406]

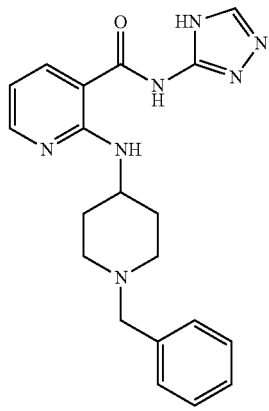 [SMILES: O=C(Nc1nnc[nH]1)c1cccnc1NC1CCN(Cc2ccccc2)CC1]

The title compound was prepared in the same manner as in Example 32, with the exception that 2-amino-1,3,4-triazole, instead of 4-(4-fluorobenzyl)morpholin-2-ylmethylamine, was used in the same molar amount (Total yield: 20.8%). $^1$H NMR (CDCl$_3$) δ 8.57 (m, 1H), 8.23 (m, 1H), 7.97 (m, 2H), 7.32 (m, 5H), 6.47 (m, 1H), 6.14 (br, 1H), 3.92 (m, 1H), 3.52 (s, 2H), 2.86 (m, 2H), 2.25 (m, 2H), 1.97 (m, 2H), 1.56 (m, 2H) ppm.

Example 34

Preparation of 2-(1-Benzylpiperidin-4-ylamino)-N-(4,6-dimethylpyrimidin-2-yl)nicotinamide [407]

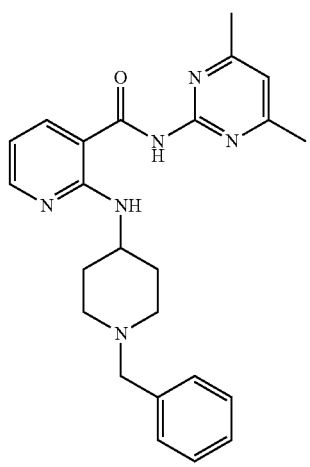 [SMILES: Cc1cc(C)nc(NC(=O)c2cccnc2NC2CCN(Cc3ccccc3)CC2)n1]

The title compound was prepared in the same manner as in Example 32, with the exception that 2-amino-4,6-dimethylpyrimidine, instead of 4-(4-fluorobenzyl)morpholin-2-ylmethylamine, was used in the same molar amount (Total yield: 19.3%). $^1$H NMR (CDCl$_3$) δ 8.26 (d, 1H), 8.10 (m, 1H), 8.05 (m, 1H), 7.36 (m, 6H), 6.50 (m, 1H), 4.12 (m, 1H), 3.57 (s, 2H), 2.83 (m, 2H), 2.29 (m, 2H), 2.05 (m, 2H), 1.64 (m, 2H), 1.28 (s, 6H) ppm.

Example 35

Preparation of 2-(1-Benzylpiperidin-4-ylamino)-N—(S)-pyrrolidin-3-ylnicotinamide [408]

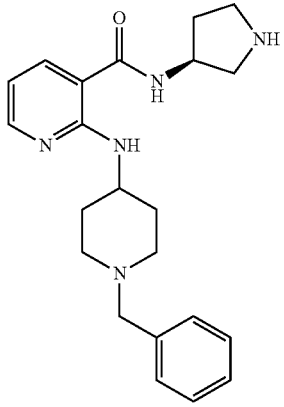 [SMILES: O=C(N[C@H]1CCNC1)c1cccnc1NC1CCN(Cc2ccccc2)CC1]

The title compound was prepared in the same manner as in Example 32, with the exception that (S)-3-amino-pyrrolidine, instead of 4-(4-fluorobenzyl)morpholin-2-ylmethylamine, was used in the same molar amount (Total yield: 13.4%). $^1$H NMR (CDCl$_3$) δ 8.19 (d, 1H), 8.05 (d, 1H), 7.44 (d, 1H), 7.11 (m, 5H), 6.50 (m, 1H), 4.12 (m, 1H), 3.53 (s, 2H), 2.82 (m, 4H), 2.32-1.93 (m, 9H), 1.61 (m, 4H) ppm.

Example 36

Preparation of 2-(1-Benzylpiperidin-4-ylamino)-N-2-(morpholin-1-yl)ethylnicotinamide [409]

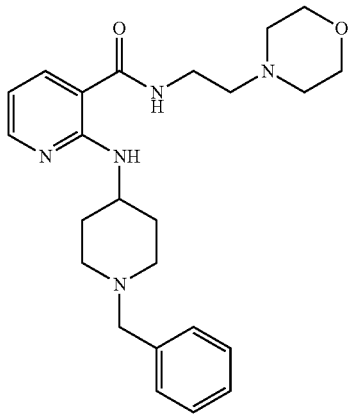 [SMILES: O=C(NCCN1CCOCC1)c1cccnc1NC1CCN(Cc2ccccc2)CC1]

The title compound was prepared in the same manner as in Example 32, with the exception that 1-(2-aminoethyl)morpholine, instead of 4-(4-fluorobenzyl)morpholin-2-ylmethylamine, was used in the same molar amount (Total yield: 74.8%). $^1$H NMR (CD$_3$OD) δ 8.12 (d, 1H), 7.97 (d, 1H), 7.86 (d, 1H), 7.35 (m, 5H), 6.54 (m, 1H), 4.95 (m, 1H), 3.71 (t, 2H), 3.56 (s, 2H), 3.38 (d, 2H), 2.83 (d, 2H), 2.53 (m, 4H), 2.31 (m, 2H), 2.02 (d, 2H), 1.61 (m, 2H) ppm.

Example 37

Preparation of N'-[2-(1-benzylpiperidin-4-ylamino)pyridine-3-carbonyl]hydrazine carboxylic acid tert-butyl ester [410]

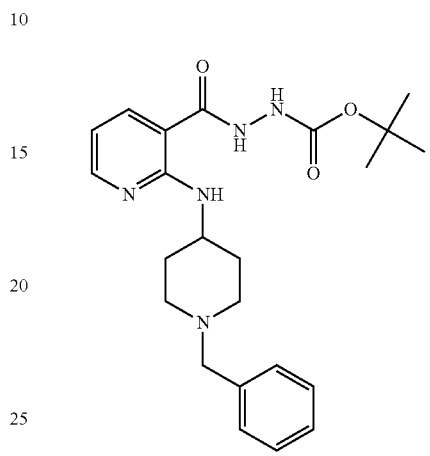

The title compound was prepared in the same manner as in Example 32, with the exception that Boc-hydrazine, instead of 4-(4-fluorobenzyl)morpholin-2-ylmethylamine, was used in the same molar amount (Total yield: 19.3%). $^1$H NMR (CDCl$_3$) δ 8.13 (m, 1H), 7.92 (m, 1H), 7.36 (m, 5H), 6.52 (m, 1H), 3.98 (m, 1H), 3.56 (s, 2H), 2.86 (d, 2H), 2.31 (m, 2H), 2.02 (m, 2H), 1.51 (m, 11H) ppm.

Example 38

Preparation of Methyl 6-{[2-(1-benzylpiperidin-4-ylamino)pyridine-3-carbonyl]amino}nicotinate

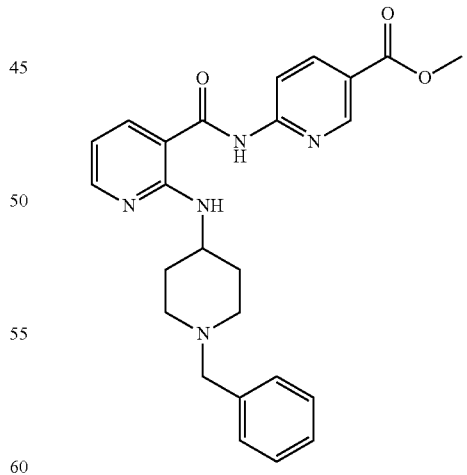

The title compound was prepared in the same manner as in Example 32, with the exception that methyl 6-aminonicotinate, instead of 4-(4-fluorobenzyl)morpholin-2-ylmethylamine, was used in the same molar amount (Total yield: 28.6%). $^1$H NMR (CDCl$_3$) δ 8.92 (s, 1H), 8.63 (s, 1H), 8.35 (s, 1H), 8.29 (d, 1H), 8.18 (d, 1H), 7.78 (d, 1H), 7.35 (m, 5H), 6.53 (m, 1H), 4.13 (m, 1H), 3.97 (s, 3H), 3.56 (s, 2H), 2.86 (d, 2H), 2.28 (t, 2H), 2.09 (d, 2H), 1.65 (m, 2H) ppm.

Example 39

Preparation of 2-(1-benzylpiperidin-4-ylamino)-N-(para-toluenesulfonamino)nicotinamide [424]

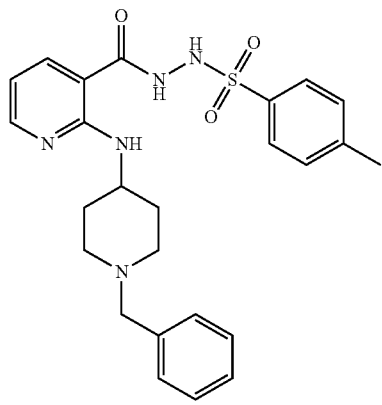 [SMILES: Cc1ccc(S(=O)(=O)NNC(=O)c2cccnc2NC2CCN(Cc3ccccc3)CC2)cc1]

The title compound was prepared in the same manner as in Example 32, with the exception that para-toluenesulfonyl hydrazine, instead of 4-(4-fluorobenzyl)morpholin-2-ylmethylamine, was used in the same molar amount (Total yield: 37.4%). $^1$H NMR (CDCl$_3$) δ 8.15 (d, 1H), 7.82 (d, 2H), 7.41-7.12 (m, 7H), 6.35-6.27 (m, 1H), 3.91-3.78 (m, 1H), 3.51 (s, 2H), 2.28 (d, 2H), 2.41 (s, 3H), 2.13 (t, 2H), 1.89 (d, 2H), 1.37-1.18 (m, 2H) ppm.

Example 40

Preparation of 2-(1-benzylpiperidin-4-ylamino)-N-(pyridin-4-ylmethyl)nicotinamide [425]

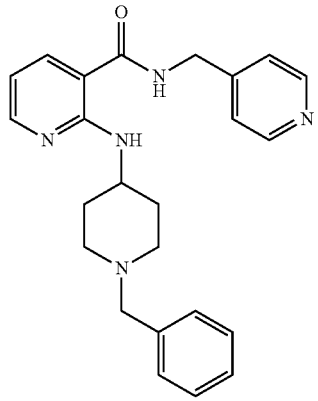 [SMILES: O=C(NCc1ccncc1)c1cccnc1NC1CCN(Cc2ccccc2)CC1]

The title compound was prepared in the same manner as in Example 32, with the exception that 4-aminomethylpyridine, instead of 4-(4-fluorobenzyl)morpholin-2-ylmethylamine, was used in the same molar amount (Total Yield: 67.8%). $^1$H NMR (CDCl$_3$) δ 8.46 (m, 3H), 8.16 (m, 2H), 7.72 (m, 2H), 7.32-7.17 (m, 5H), 6.39 (m, 1H), 4.51 (d, 2H), 4.01 (m, 1H), 3.48 (s, 2H), 2.78 (d, 2H), 2.21 (t, 2H), 1.98 (d, 2H), 1.59 (m, 2H) ppm.

Example 41

Preparation of 2-(1-Benzylpiperidin-4-ylamino)-N-(1,2-diphenylethyl)nicotinamide [426]

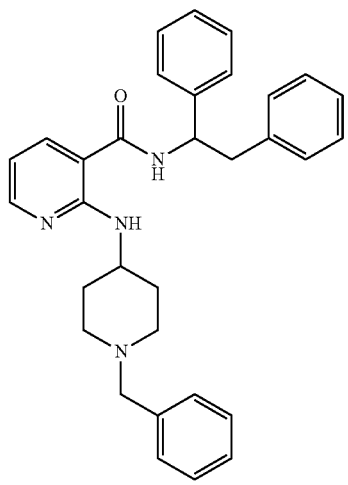 [SMILES: O=C(NC(Cc1ccccc1)c1ccccc1)c1cccnc1NC1CCN(Cc2ccccc2)CC1]

The title compound was prepared in the same manner as in Example 32, with the exception that 1,2-diphenylethylamine, instead of 4-(4-fluorobenzyl)morpholin-2-ylmethylamine, was used in the same molar amount (Total yield: 84.3%). $^1$H NMR (CDCl$_3$) δ 8.19 (d, 1H), 7.98 (d, 1H), 7.46-7.22 (m, 15H), 7.11 (d, 1H), 6.44 (m, 1H), 6.25 (d, 1H), 5.43 (q, 1H), 4.01 (m, 1H), 3.52 (s, 2H), 3.20 (dd, 2H), 2.81 (d, 2H), 2.23 (t, 2H), 2.02 (d, 2H), 1.59 (m, 2H) ppm.

Example 42

Preparation of 2-(1-Benzylpiperidin-4-ylamino)-N-(2-methoxyethyl)nicotinamide [427]

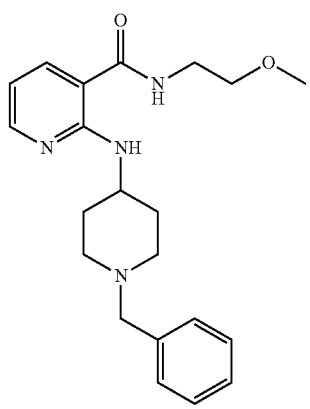 [SMILES: COCCNC(=O)c1cccnc1NC1CCN(Cc2ccccc2)CC1]

The title compound was prepared in the same manner as in Example 32, with the exception that 2-methoxyethylamine, instead of 4-(4-fluorobenzyl)morpholin-2-ylmethylamine, was used in the same molar amount (Total yield: 77.4%). $^1$H NMR (CDCl$_3$) δ 8.17 (s, 1H), 8.16 (s, 1H), 7.55 (d, 1H), 7.31 (m, 5H), 6.60 (br, 1H), 6.42 (m, 1H), 4.02 (m, 1H), 3.58-3.50 (m, 6H), 3.35 (s, 3H), 2.79 (d, 2H), 2.22 (t, 2H), 2.01 (d, 2H), 1.61 (m, 2H) ppm.

Example 43

Preparation of 2-(1-Benzylpiperidin-4-ylamino)-N-(5-methylthiazol-2-yl)nicotinamide [428]

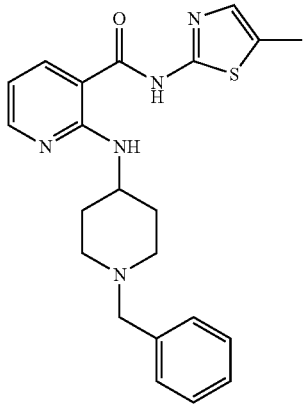 [SMILES: Cc1cnc(NC(=O)c2cccnc2NC2CCN(Cc3ccccc3)CC2)s1]

The title compound was prepared in the same manner as in Example 32, with the exception that 2-amino-5-methylthiazole, instead of 4-(4-fluorobenzyl)morpholin-2-ylmethylamine, was used in the same molar amount (Total yield: 12.1%). $^1$H NMR (CDCl$_3$) δ 8.73 (d, 1H), 8.19 (d, 1H), 7.59 (s, 1H), 7.32 (m, 5H), 6.53 (d, 1H), 4.19 (m, 1H), 3.47 (s, 2H), 2.82 (d, 2H), 2.42 (s, 3H), 2.24 (t, 2H), 2.10 (d, 2H), 1.70 (m, 2H) ppm.

Example 44

Preparation of 2-(1-Benzylpiperidin-4-ylamino)-N-(3-methylpyridin-2-yl)nicotinamide [429]

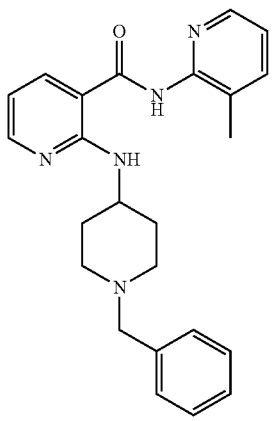 [SMILES: Cc1cccnc1NC(=O)c1cccnc1NC1CCN(Cc2ccccc2)CC1]

The title compound was prepared in the same manner as in Example 32, with the exception that 2-amino-3-methylpyridine, instead of 4-(4-fluorobenzyl)morpholin-2-ylmethylamine, was used in the same molar amount (Total yield: 9.4%). $^1$H NMR (CDCl$_3$) δ 8.28 (d, 1H), 8.27 (s, 1H), 8.11 (m, 1H), 7.89 (m, 1H), 7.64 (d, 1H), 7.32 (m, 5H), 7.11 (m, 1H), 6.52 (m, 1H), 4.08 (m, 1H), 3.54 (s, 2H), 2.83 (d, 2H), 2.34 (s, 3H), 2.26 (t, 2H), 2.06 (d, 2H), 1.58 (m, 2H) ppm.

Example 45

Preparation of 2-(1-Benzylpiperidin-4-ylamino)-N-(azepan-2-on-3-yl)nicotinamide [430]

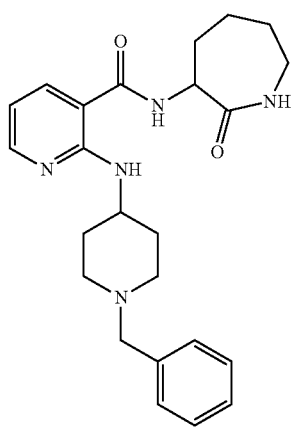 [SMILES: O=C(NC1CCCCNC1=O)c1cccnc1NC1CCN(Cc2ccccc2)CC1]

The title compound was prepared in the same manner as in Example 32, with the exception that 3-amino-azepan-2-one, instead of 4-(4-fluorobenzyl)morpholin-2-ylmethylamine, was used in the same molar amount (Total yield: 50.1%). $^1$H NMR (CDCl$_3$) δ 8.20 (m, 2H), 7.69 (d, 1H), 7.55 (d, 1H), 7.33 (m, 5H), 6.48 (m, 1H), 6.14 (m, 1H), 4.64 (m, 1H), 4.06 (m, 1H), 3.54 (s, 2H), 3.32 (m, 2H), 2.85 (d, 2H), 2.32-1.43 (m, 12H) ppm.

Example 46

Preparation of 2-(1-Benzylpiperidin-4-ylamino)-N-(4-fluorobenzyl)nicotinamide [431]

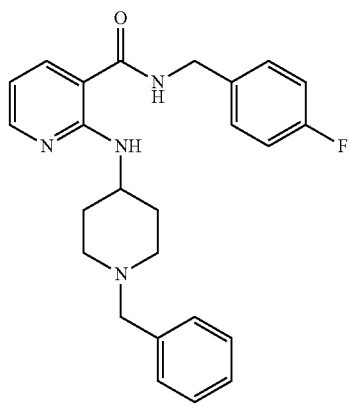 [SMILES: O=C(NCc1ccc(F)cc1)c1cccnc1NC1CCN(Cc2ccccc2)CC1]

The title compound was prepared in the same manner as in Example 32, with the exception that 4-fluorobenzylamine, instead of 4-(4-fluorobenzyl)morpholin-2-ylmethylamine, was used in the same molar amount (Total yield: 81.1%). $^1$H NMR (CDCl$_3$) δ 8.19 (m, 2H), 7.54 (d, 1H), 7.30 (m, 6H), 7.03 (t, 2H), 6.50 (br, 1H), 6.42 (m, 1H), 4.05 (m, 1H), 3.55 (s, 2H), 2.83 (d, 2H), 2.25 (t, 2H), 2.05 (d, 2H), 1.63 (m, 2H) ppm.

Example 47

Preparation of 2-(1-Benzylpiperidin-4-ylamino)-N-(2-ethylhexyl)nicotinamide [436]

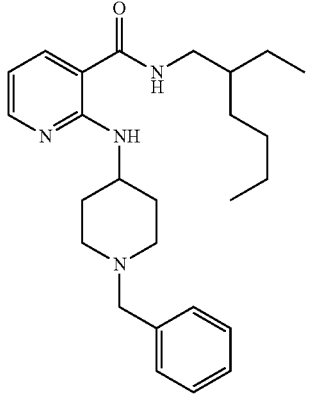 [SMILES: CCCCC(CC)CNC(=O)c1cccnc1NC1CCN(Cc2ccccc2)CC1]

The title compound was prepared in the same manner as in Example 32, with the exception that 2-ethylhexylamine, instead of 4-(4-fluorobenzyl)morpholin-2-ylmethylamine, was used in the same molar amount (Total yield: 89.4%). $^1$H NMR (CDCl$_3$) δ 8.27 (d, 1H), 8.08 (d, 1H), 7.51 (d, 1H), 7.30 (m, 5H), 6.44 (m, 1H), 6.05 (m, 1H), 4.02 (m, 1H), 3.52 (s, 2H), 3.34 (t, 2H), 2.27 (t, 2H), 2.06 (d, 2H), 1.62 (m, 2H), 1.45-1.36 (m, 8H), 0.93 (m, 6H) ppm.

Example 48

Preparation of 2-(1-Benzylpiperidin-4-ylamino)-N-(3-methyl-2-methylsulfanyl-3,4-dihydroquinazolin-4-on-6-yl)nicotinamide [439]

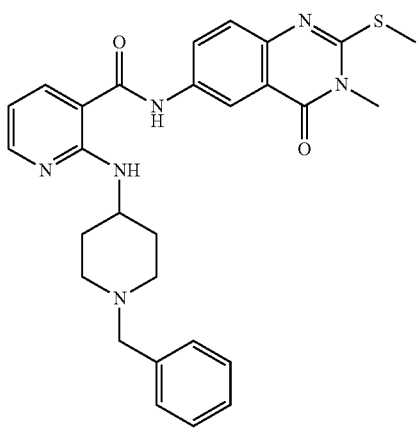 [SMILES: CSc1nc2ccc(NC(=O)c3cccnc3NC3CCN(Cc4ccccc4)CC3)cc2c(=O)n1C]

The title compound was prepared in the same manner as in Example 32, with the exception that 6-amino-3-methyl-2-methylsulfanyl-3H-quinazolin-4-one obtained in Preparation Example 20, instead of 4-(4-fluorobenzyl)morpholin-2-ylmethylamine, was used in the same molar amount (Total yield: 77.0%). $^1$H NMR (DMSO-d$_6$) δ 8.28-7.95 (m, 5H), 7.73-7.46 (m, 6H), 6.72 (m, 1H), 4.31 (m, 1H), 3.53 (s, 3H), 3.47 (s, 2H), 3.24-3.11 (m, 2H), 2.66 (s, 3H), 2.58 (m, 2H), 2.20 (m, 2H), 1.78 (m, 2H) ppm.

Example 49

Preparation of 6-benzyl-2-{[2-(1-benzylpiperidin-4-ylamino)pyridine-3-carbonyl]amino}-4,5,6,7-tetrahydro-thieno[2,3-c]pyridine-3-carboxylic acid methyl ester [440]

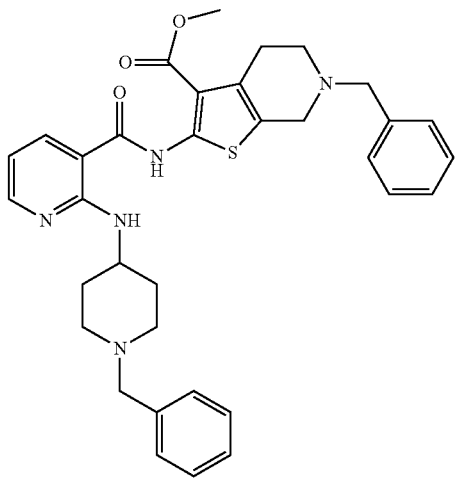 [SMILES: COC(=O)c1c(NC(=O)c2cccnc2NC2CCN(Cc3ccccc3)CC2)sc2c1CCN(Cc1ccccc1)C2]

The title compound was prepared in the same manner as in Example 32, with the exception that methyl 2-amino-6-benzyl-4,5,6,7-tetrahydro-thieno[2,3-c]pyridine-3-carboxylate obtained in Preparation Example 2, instead of 4-(4-fluorobenzyl)morpholin-2-ylmethylamine, was used in the same molar amount (Total yield: 84.4%). $^1$H NMR (CDCl$_3$) δ 8.42 (d, 1H), 8.28 (d, 1H), 7.88 (d, 1H), 7.35 (m, 10H), 6.57 (m, 1H), 4.12 (m, 1H), 3.91 (s, 3H), 3.72 (s, 2H), 3.61 (s, 2H), 3.55 (s, 2H), 2.93-2.82 (m, 6H), 2.27 (t, 2H), 2.07 (d, 2H), 1.67 (m, 2H) ppm.

Example 50

Preparation of 6-Ethoxycarbamate-2-{[2-(1-benzylpiperidin-4-ylamino)pyridine-3-carbonyl]amino}-4,5,6,7-tetrahydro-thieno[2,3-c]pyridine-3-carboxylic acid methyl ester [441]

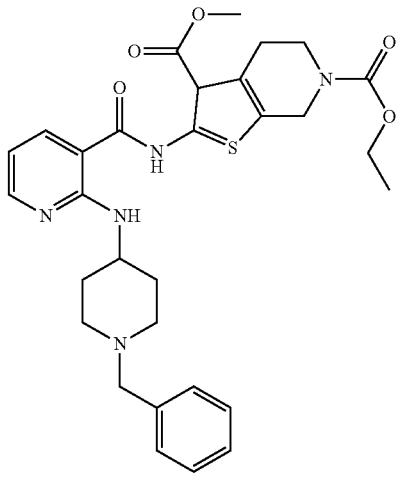

The title compound was prepared in the same manner as in Example 32, with the exception that 2-amino-4,7-dihydro-5H-thieno[2,3-c]pyridine-3,6-dicarboxylic acid 6-ethyl ester 3-methyl ester obtained in Preparation Example 3, instead of 4-(4-fluorobenzyl)morpholin-2-ylmethylamine, was used in the same molar amount (Total yield: 81.1%). $^1$H NMR (CDCl₃) δ 8.43 (d, 1H), 8.26 (d, 2H), 7.88 (d, 1H), 7.41 (m, 5H), 6.61 (m, 1H), 4.58 (s, 2H), 4.23-4.15 (m, 3H), 3.91 (s, 3H), 3.82 (s, 2H), 3.73 (st, 2H), 3.09 (d, 2H), 2.90 (t, 2H), 2.57 (t, 2H), 2.20 (d, 2H), 1.91 (m, 2H) ppm.

Example 51

Preparation of 2-{[2-(1-Benzylpiperidin-4-ylamino)pyridine-3-carbonyl]amino}-4,5,6,7-tetrahydro-thieno[2,3-c]pyridine-3-carboxylic acid methyl ester [442]

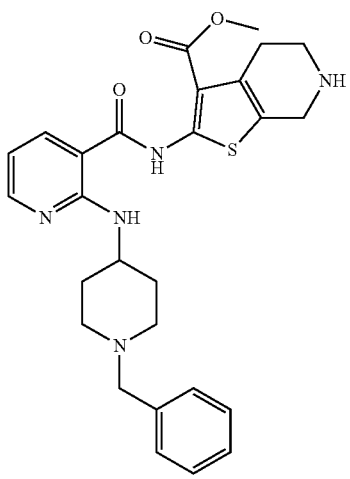 [SMILES: COC(=O)c1c(NC(=O)c2cccnc2NC2CCN(Cc3ccccc3)CC2)sc2c1CCNC2]

The title compound was prepared in the same manner as in Example 32, with the exception that methyl 2-amino-4,5,6,7-tetrahydro-thien[2,3-c]pyridine-3-carboxylate hydrochloride obtained in Preparation Example 1, instead of 4-(4-fluorobenzyl)morpholin-2-ylmethylamine, was used in the same molar amount while the amount of triethylamine was increased to 4.0 eq (Total yield: 83.1%). ¹H NMR (CDCl₃) δ 8.40 (d, 1H), 8.20 (d, 1H), 7.75 (d, 1H), 7.25-7.18 (m, 5H), 6.49 (m, 1H), 4.07 (m, 1H), 3.82 (m, 5H), 3.09-2.72 (m, 6H), 2.22 (t, 2H), 2.07 (d, 2H), 1.64 (m, 2H) ppm.

Example 52

Preparation of 2-(1-Benzylpiperidin-4-ylamino)-N-(3,4-dimethoxyphenyl)nicotinamide [443]

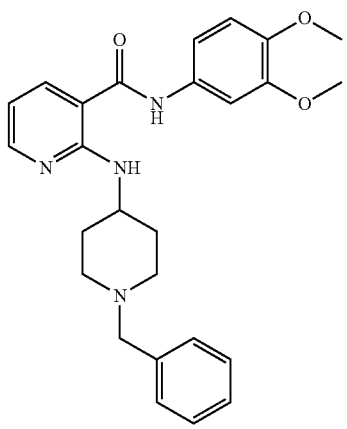 [SMILES: COc1ccc(NC(=O)c2cccnc2NC2CCN(Cc3ccccc3)CC2)cc1OC]

The title compound was prepared in the same manner as in Example 32, with the exception that 3,4-dimethoxyaniline, instead of 4-(4-fluorobenzyl)morpholin-2-ylmethylamine, was used in the same molar amount (Total yield: 89.9%). ¹H NMR (CDCl₃) δ 8.23 (d, 1H), 8.01 (d, 1H), 7.68 (d, 1H), 7.59 (s, 1H), 7.34-7.25 (m, 5H), 6.90 (m, 2H), 6.51 (m, 1H), 4.06 (m, 1H), 3.91 (s, 3H), 3.89 (s, 3H), 3.52 (s, 2H), 2.82 (d, 2H), 2.24 (t, 2H), 2.03 (t, 2H), 1.61 (m, 2H) ppm.

Example 53

Preparation of 2-{[2-(1-Benzylpiperidin-4-ylamino)-6-chloropyridine-3-carbonyl]amino}-4,5,6,7-tetrahydrothieno[2,3-c]pyridine-3-carboxylic acid methyl ester

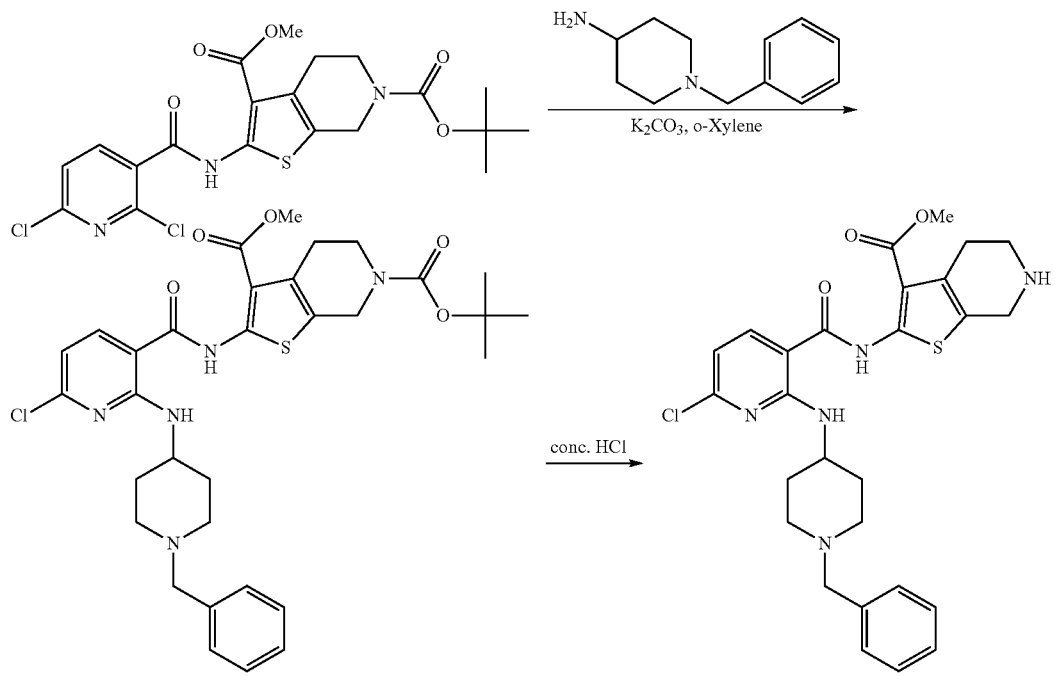

A solution of 2-[(2,6-dichloropyridine-3-carbonyl)amino]-4,7-dihydro-5H-thieno[2,3-c]pyridine-3,6-dicarboxylic acid 6-tert-butyl ester 3-methyl ester (510 mg, 1.05 mmol, 1.05 eq) obtained in Preparation Example 11, 4-amino-1-benzylpiperidine (1.0 mmol), and anhydrous potassium carbonate (1.2 mmol) in ortho-xylene was stirred for 24 hrs under reflux. The reaction mixture was cooled to a room temperature, and further stirred for 3 hrs in conc. HCl aqueous solution (excess) under reflux. The reaction mixture was cooled to a room temperature, added with 10 ml of ethylacetate, and extracted twice with 20 ml of distilled water per round. Thereafter, the aqueous layer was again washed 20 ml of ethylacetate, and adjusted to a pH of about 9-10 with a 2 N sodium hydroxide aqueous solution. The resulting mixture was extracted twice with 20 ml of methylene chloride per round, washed with 30 ml of saturated saline, and dried over a desiccant to remove water. Then the solvent was removed by concentration in a reduced pressure. In order to a desired fraction, purification through silica gel column chromatography (mobile phase=10 (v/v) % methanol in chloroform) was performed to afford the title compound. Yield: 72.3% $^1$H NMR (DMSO-d$_6$) δ 7.46 (d, 1H), 7.39 (d, 1H), 7.32 (m, 5H), 6.62 (d, 1H), 6.41 (d, 1H), 4.43 (s, 2H), 3.83 (m, 1H), 3.69 (s, 2H), 3.59 (m, 2H), 2.73 (m, 4H), 2.08 (t, 2H), 1.82 (d, 2H), 1.51 (m, 2H) ppm.

Example 54

Preparation of 2-{[2-(1-Benzylpiperidin-4-ylamino)-6-chloropyridine-3-carbonyl]amino}-4,5,6,7-tetrahydrothieno[2,3-c]pyridine-3-carboxylic acid methyl ester

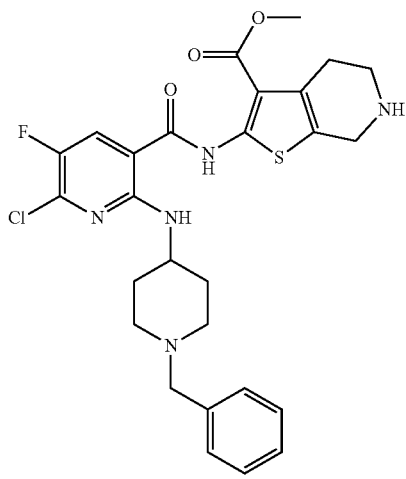 [SMILES: COC(=O)c1c(NC(=O)c2cc(F)c(Cl)nc2NC2CCN(Cc3ccccc3)CC2)sc2c1CCNC2]

The title compound was prepared in the same manner as in Example 53, with the exception that 2-[(2,6-dichloro-5-fluoro-pyridine-3-carbonyl)amino]-4,7-dihydro-5H-thieno[2,3-c]pyridine-3,6-dicarboxylic acid 6-tert-butyl ester 3-methyl ester obtained in Preparation Example 12, instead of 2-[(2,6-dichloropyridine-3-carbonyl)amino]-4,7-dihydro-5H-thieno[2,3-c]pyridine-3,6-dicarboxylic acid 6-tert-butyl ester 3-methyl ester, was used in the same molar amount. Yield: 51.4%, $^1$H NMR (CDCl$_3$) δ 7.83 (d, 1H), 7.34 (m, 5H), 5.04 (m, 1H), 4.06 (m, 1H), 3.92 (m, 5H), 3.54 (s, 3H), 3.12 (t, 2H), 2.88 (m, 4H), 2.21 (m, 2H), 2.07 (m, 2H), 1.59 (m, 2H) ppm.

Example 55

Preparation of 2-{[2-(1-(2-hydroxyethyl)piperidin-4-ylamino)pyridine-3-carbonyl]amino}-4,5,6,7-tetrahydrothieno[2,3-c]pyridine-3-carboxylic acid methyl ester [503]

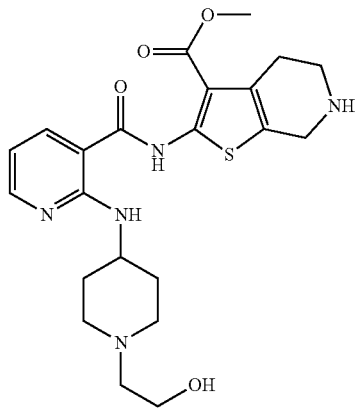 [SMILES: COC(=O)c1c(NC(=O)c2cccnc2NC2CCN(CCO)CC2)sc2c1CCNC2]

The title compound was prepared in the same manner as in Example 53, with the exception that 2-[(2-chloropyridine-3-carbonyl)-amino]-4,7-dihydro-5H-thieno[2,3-c]pyridine-3,6-dicarboxylic acid 6-tert-butyl ester 3-methyl ester obtained in Preparation Example 10, instead of 2-[(2,6-dichloropyridine-3-carbonyl)amino]-4,7-dihydro-5H-thieno[2,3-c]pyridine-3,6-dicarboxylic acid 6-tert-butyl ester 3-methyl ester, and 4-amino-1-(2-hydroxyethyl)piperidine obtained in Preparation Example 17, instead of 4-amino-1-benzylpiperidine, were used in the same molar amounts. Yield: 67.7%, $^1$H NMR (CDCl$_3$) δ 8.52 (m, 1H), 8.26 (d, 1H), 7.88 (d, 1H), 6.61 (m, 1H), 4.26 (m, 1H), 3.99-3.87 (m, 5H), 3.73 (t, 2H), 3.12 (m, 2H), 2.98-2.80 (m, 4H), 2.59-2.12 (m, 6H), 1.68 (m, 2H) ppm.

Example 56

Preparation of 2-{[6-Chloro-2-(1-(2-hydroxyethyl)piperidin-4-ylamino)pyridine-3-carbonyl]amino}-4,5,6,7-tetrahydrothieno[2,3-c]pyridine-3-carboxylic acid methyl ester [504]

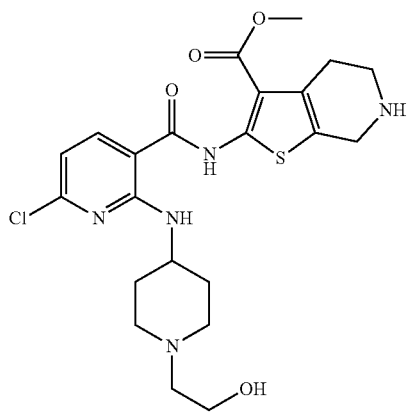 [SMILES: COC(=O)c1c(NC(=O)c2ccc(Cl)nc2NC2CCN(CCO)CC2)sc2c1CCNC2]

The title compound was prepared in the same manner as in Example 53, with the exception that 4-amino-1-(2-hydroxyethyl)piperidine obtained in Preparation Example 17, instead of 4-amino-1-benzylpiperidine, was used in the same molar amount. Yield: 74.4%, $^1$H NMR (CDCl$_3$) δ 7.31 (d, 1H), 6.55 (d, 1H), 6.23 (m, 1H), 6.09 (br, 1H), 4.02 (m, 1H), 4.82 (s, 3H), 3.77 (t, 2H), 3.64 (t, 2H), 2.93-2.82 (m, 4H), 2.58 (d, 2H), 2.33 (t, 2H), 2.11-1.75 (m, 4H), 1.54 (m, 2H) ppm.

Example 57

Preparation of 2-{[6-Chloro-5-fluoro-2-(1-(2-hydroxyethyl)piperidin-4-ylamino)pyridine-3-carbonyl]amino}-4,5,6,7-tetrahydrothieno[2,3-c]pyridine-3-carboxylic acid methyl ester [505]

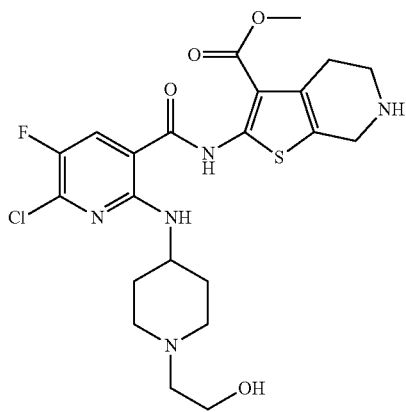 [SMILES: COC(=O)c1c(NC(=O)c2cc(F)c(Cl)nc2NC2CCN(CCO)CC2)sc2c1CCNC2]

The title compound was prepared in the same manner as in Example 53, with the exception that 2-[(2,6-dichloro-5-fluoro-pyridine-3-carbonyl)amino]-4,7-dihydro-5H-thieno[2,3-c]pyridine-3,6-dicarboxylic acid 6-tert-butyl ester 3-methyl ester obtained in Preparation Example 12, instead of 2-[(2,6-dichloropyridine-3-carbonyl)amino]-4,7-dihydro-5H-thieno[2,3-c]pyridine-3,6-dicarboxylic acid 6-tert-butyl ester 3-methyl ester, and 4-amino-1-(2-hydroxyethyl)piperidine obtained in Preparation Example 17, instead of 4-amino-1-benzylpiperidine, were used in the same molar amounts. Yield: 50.3%, $^1$H NMR (CDCl$_3$) δ 7.83 (d, 1H), 5.02 (m, 1H), 4.06 (m, 1H), 3.92 (m, 5H), 3.62 (t, 2H), 3.13 (t, 2H), 2.96-2.81 (m, 4H), 2.58 (t, 2H), 2.34 (t, 2H), 2.11 (d, 2H), 1.58 (m, 2H) ppm.

Example 58

Preparation of 2-{[2-(2,2,6,6-tetramethylpiperidin-4-ylamino)pyridine-3-carbonyl]amino}-4,5,6,7-tetrahydrothieno[2,3-c]pyridine-3-carboxylic acid methyl ester [506]

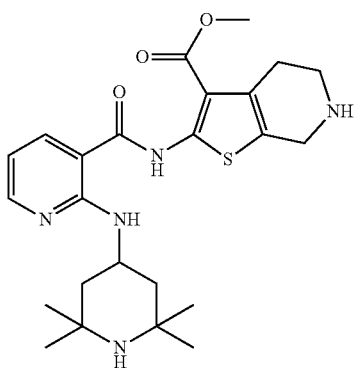 [SMILES: COC(=O)c1c(NC(=O)c2cccnc2NC2CC(C)(C)NC(C)(C)C2)sc2c1CCNC2]

The title compound was prepared in the same manner as in Example 55, with the exception that 4-amino-2,2,6,6-tetramethylpiperidine, instead of 4-amino-1-(2-hydroxyethyl)piperidine, was used in the same molar amount. Yield: 86.0%, $^1$H NMR (CDCl$_3$) δ 8.33-8.24 (m, 2H), 7.88 (d, 1H), 6.58 (m, 1H), 4.59 (m, 1H), 3.92 (m, 5H), 3.11 (t, 2H), 2.78 (st, 2H), 2.08 (d, 2H), 1.33 (s, 6H), 1.26-1.1 (m, 8H) ppm.

Example 59

Preparation of 2-{[2-(2,2,6,6-tetramethylpiperidin-4-ylamino)6-chloropyridine-3-carbonyl]amino}-4,5,6,7-tetrahydrothieno[2,3-c]pyridine-3-carboxylic acid methyl ester [507]

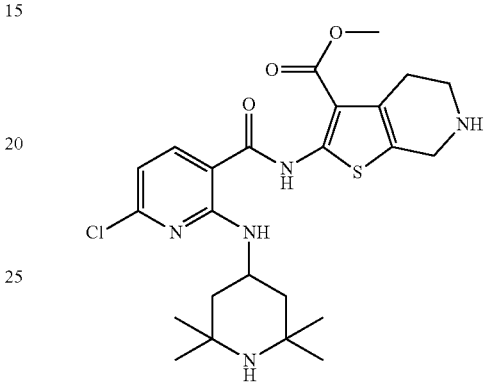

The title compound was prepared in the same manner as in Example 53, with the exception that 4-amino-2,2,6,6-tetramethylpiperidine, instead of 4-amino-1-benzylpiperidine, was used in the same molar amount. Yield: 77.9%, $^1$H NMR (CDCl$_3$) δ 8.28 (d, 1H), 7.42 (d, 1H) 6.39 (m, 1H), 6.15 (m, 1H), 5.99 (br, 1H), 4.39 (m, 1H), 3.97-3.75 (m, 5H), 3.52 (m, 2H), 2.03 (m, 2H), 1.68 (m, 2H), 1.42 (s, 6H), 1.18 (s, 6H) ppm.

Example 60

Preparation of 2-{[6-chloro-5-fluoro-2-(2,2,6,6-tetramethylpiperidin-4-ylamino)pyridine-3-carbonyl]amino}-4,5,6,7-tetrahydrothieno[2,3-c]pyridine-3-carboxylic acid methyl ester [508]

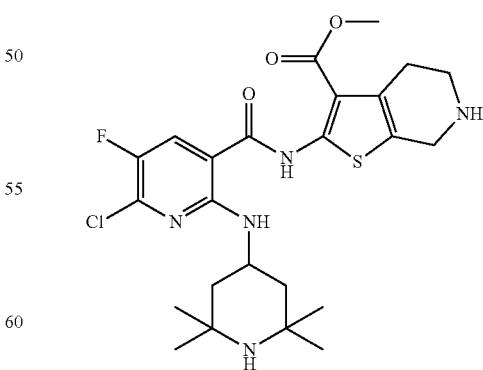

The title compound was prepared in the same manner as in Example 53, with the exception that 2-[(2,6-dichloro-5-fluoro-pyridine-3-carbonyl)amino]-4,7-dihydro-5H-thieno[2,3-c]pyridine-3,6-dicarboxylic acid 6-tert-butyl ester 3-methyl ester obtained in Preparation Example 12, instead of 2-[(2,6-dichloropyridine-3-carbonyl)amino]-4,7-dihydro-5H-thieno[2,3-c]pyridine-3,6-dicarboxylic acid 6-tert-butyl ester 3-methyl ester, and 4-amino-2,2,6,6-tetramethylpiperidine, instead of 4-amino-1-benzylpiperidine, were used in the same molar amounts. Yield: 49.2%, $^1$H NMR (CDCl$_3$) δ 7.83 (d, 1H), 4.91 (m, 1H), 4.48 (m, 1H), 3.92 (m, 5H), 3.12 (d, 2H), 2.80 (m, 2H), 2.06 (d, 2H), 1.33 (s, 6H), 1.25 (m, 2H), 1.17 (s, 6H) ppm.

Example 61

Preparation of 2-{[2-(1-benzylpiperidin-3-ylamino)pyridine-3-carbonyl]amino}-4,5,6,7-tetrahydrothieno[2,3-c]pyridine-3-carboxylic acid methyl ester

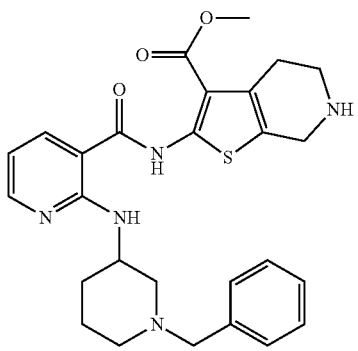 [SMILES: COC(=O)c1c(NC(=O)c2cccnc2NC2CCCN(Cc3ccccc3)C2)sc2c1CCNC2]

The title compound was prepared in the same manner as in Example 55, with the exception that 3-amino-1-benzylpiperidine obtained in Preparation Example 18, instead of 4-amino-1-(2-hydroxyethyl)piperidine, was used in the same molar amount. Yield: 80.1%, $^1$H NMR (CDCl$_3$) δ 8.52 (m, 1H) 8.26 (d, 1H), 7.83 (d, 1H), 7.51-7.11 (m, 5H), 6.54 (m, 1H), 4.38 (m, 1H), 4.18 (s, 2H), 3.89 (s, 3H), 3.59 (m, 2H), 3.33 (d, 2H), 3.04 (m, 2H), 2.74-2.43 (m, 4H), 1.89-1.64 (m, 4H) ppm.

Example 62

Preparation of 2-{[2-(1-Benzylpiperidin-3-ylamino)-6-chloropyridine-3-carbonyl]amino}-4,5,6,7-tetrahydrothieno[2,3-c]pyridine-3-carboxylic acid methyl ester

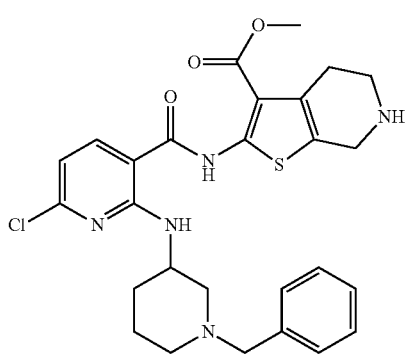 [SMILES: COC(=O)c1c(NC(=O)c2ccc(Cl)nc2NC2CCCN(Cc3ccccc3)C2)sc2c1CCNC2]

The title compound was prepared in the same manner as in Example 53, with the exception that 3-amino-1-benzylpiperidine obtained in Preparation Example 18, instead of 4-amino-1-benzylpiperidine, was used in the same molar amount. Yield: 73.5%, $^1$H NMR (CDCl$_3$) δ 7.30 (m, 6H), 6.55 (m, 1H), 6.51 (d, 1H), 6.09 (br, 1H), 4.54 (s, 2H), 4.23 (m, 1H), 3.86-3.72 (m, 5H), 3.49 (m, 2H), 2.92 (t, 2H), 2.63-2.28 (m, 4H), 1.80-1.59 (m, 6H) ppm.

Example 63

Preparation of 2-{[2-(1-Benzylpiperidin-3-ylamino)-6-chloro-5-fluoropyridine-3-carbonyl]amino}-4,5,6,7-tetrahydrothieno[2,3-c]pyridine-3-carboxylic acid methyl ester

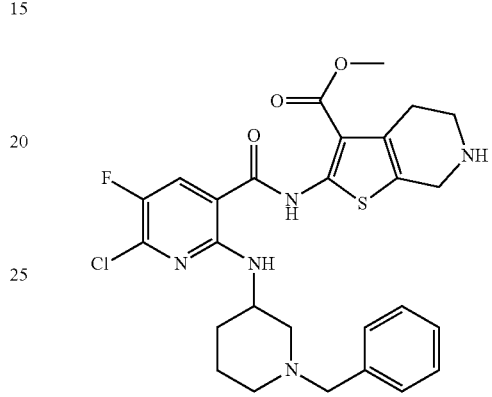

The title compound was prepared in the same manner as in Example 57, with the exception that 3-amino-1-benzylpiperidine obtained in Preparation Example 18, instead of 4-amino-1-(2-hydroxyethyl)piperidine, was used in the same molar amount. Yield: 53.7%, $^1$H NMR (CDCl$_3$) δ 7.83 (d, 1H), 7.34 (m, 5H), 5.89 (m, 1H), 4.33 (m, 1H), 3.92 (m, 5H), 3.51 (m, 2H), 3.12 (t, 2H), 2.81 (t, 2H), 2.74-2.48 (m, 2H), 2.34-2.15 (m, 2H), 1.80-1.62 (m, 4H) ppm.

Example 64

Preparation of 6-Chloro-N-(2-ethylhexyl)-2-[1-(2-hydroxyethyl)piperidin-4-ylamino]nicotinamide

[515]

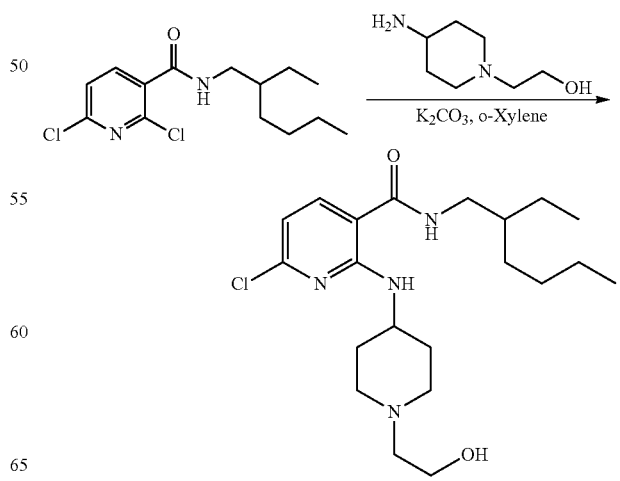

A solution of 2,6-dichloro-N-(2-ethylhexyl)-nicotinamide (318 mg, 1.05 mmol, 1.05 eq) prepared in Preparation Example 14, 4-amino-1-(2-hydroxyethyl)piperidine (1.0 mmol) obtained in Preparation Example 17, and anhydrous potassium carbonate (1.2 mmol) in 5 ml of ortho-xylene was stirred for 24 hrs under reflux. The reaction mixture was cooled to room temperature, added with 15 ml of ethylacetate, and extracted twice with 30 ml of 1 N aqueous HCl solution per round. The aqueous layer thus obtained was again washed with ethylacetate and adjusted to a pH of about 9-10 with a 2 N aqueous sodium hydroxide solution. Subsequently, the reaction mixture was extracted twice with 20 ml of methylene chloride, washed with saturated saline, and water was removed by a desiccant. In order to obtain a desired fraction, the solvent was removed by concentration in a reduced pressure. The purification through silica gel column chromatography (mobile phase: 20 (v/v) % EA in hexane) was performed to afford the title compound. Yield: 77.9% $^1$H NMR (CDCl$_3$) δ 8.35 (d, 1H), 7.45 (d, 1H), 6.44 (d, 1H), 6.01 (br, 1H), 4.03 (m, 1H), 3.62 (t, 2H), 3.32 (t, 2H), 2.87 (d, 2H), 2.56 (t, 2H), 2.33 (t, 2H), 2.07 (d, 2H), 1.59 (m, 2H), 1.42-1.16 (m, 8H), 0.98-0.91 (m, 6H) ppm.

Example 65

Preparation of N-(2-ethylhexyl)-2-(2,2,6,6-tetramethylpiperidin-4-ylamino)nicotinamide [517]

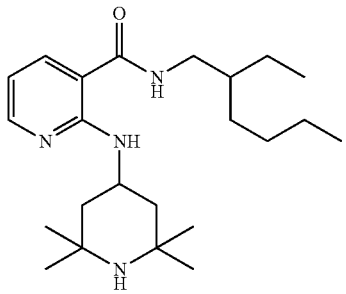 [SMILES: CCCCC(CC)CNC(=O)c1cccnc1NC1CC(C)(C)NC(C)(C)C1]

The title compound was prepared in the same manner as in Example 64, with the exception that 2-chloro-N-(2-ethylhexyl)nicotinamide obtained in Preparation Example 13, instead of 2,6-dichloro-N-(2-ethylhexyl)nicotinamide, and 4-amino-2,2,6,6-tetramethylpiperidine, instead of 4-amino-1-(2-hydroxyethyl)piperidine, were used in the same molar amounts. Yield: 84.4% $^1$H NMR (CDCl$_3$) δ 8.13 (d, 1H), 7.82 (d, 1H), 7.49 (d, 1H), 6.40 (m, 1H), 6.21 (br, 1H), 4.44 (m, 1H), 3.26 (t, 2H), 1.98 (dd, 2H), 1.49 (m, 1H), 1.22 (m, 14H), 1.07 (m, 8H), 0.89-0.81 (m, 6H) ppm.

Example 66

Preparation of 6-chloro-N-(2-ethylhexyl)-5-fluoro-2-(2,2,6,6-tetramethylpiperidin-4-ylamino)nicotinamide

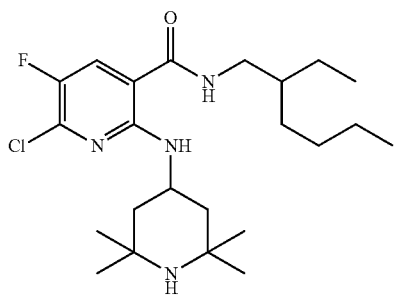 [SMILES: CCCCC(CC)CNC(=O)c1cc(F)c(Cl)nc1NC1CC(C)(C)NC(C)(C)C1]

The title compound was prepared in the same manner as in Example 64, with the exception that 2,6-dichloro-N-(2-ethylhexyl)-5-fluoronicotinamide obtained in Preparation Example 15, instead of 2,6-dichloro-N-(2-ethylhexyl)nicotinamide, and 4-amino-2,2,6,6-tetramethylpiperidine, instead of 4-amino-1-(2-hydroxyethyl)piperidine, were used in the same molar amounts. Yield: 61.7% $^1$H NMR (CDCl$_3$) δ 7.85 (d, 1H), 7.34 (d, 1H), 4.37 (m, 1H), 3.42-3.28 (m, 2H), 2.02 (dd, 2H), 1.53 (m, 1H), 1.30 (m, 14H), 1.13 (m, 8H), 1.01-0.87 (m, 6H) ppm.

Example 67

Preparation of 2-(1-benzylpiperidin-3-ylamino)-N-(2-ethylhexyl)nicotinamide [520]

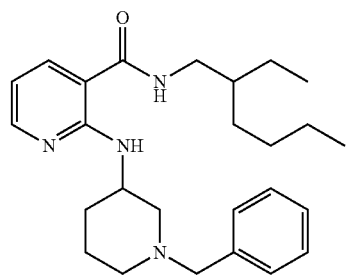 [SMILES: CCCCC(CC)CNC(=O)c1cccnc1NC1CCCN(Cc2ccccc2)C1]

The title compound was prepared in the same manner as in Example 65, with the exception that 3-amino-1-benzylpiperidine obtained in Preparation Example 18, instead of 4-amino-2,2,6,6-tetramethylpiperidine, was used in the same molar amount. Yield: 87.3% $^1$H NMR (CDCl$_3$) δ 8.29 (d, 1H), 8.15 (d, 1H), 7.53 (d, 1H), 7.41-7.21 (m, 5H), 6.40 (m, 1H), 6.31 (br, 1H), 4.28 (m, 1H), 3.48 (s, 2H), 3.34 (m, 2H), 2.90-2.27 (m, 5H), 1.86-1.54 (m, 4H), 1.41-1.22 (m, 8H), 0.95-0.90 (m, 6H) ppm.

Example 68

Preparation of 2-(1-Benzylpiperidin-3-ylamino)-6-chloro-N-(2-ethylhexyl)-5-fluoronicotinamide [522]

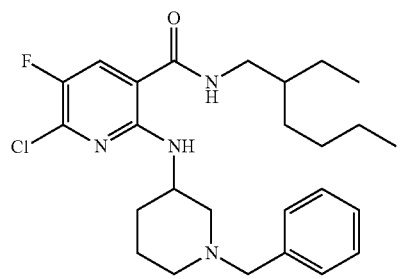 [SMILES: CCCCC(CC)CNC(=O)c1cc(F)c(Cl)nc1NC1CCCN(Cc2ccccc2)C1]

The title compound was prepared in the same manner as in Example 66, with the exception that 3-amino-1-benzylpiperidine obtained in Preparation Example 18, instead of 4-amino-2,2,6,6-tetramethylpiperidine, was used in the same molar amount. Yield: 70.2% $^1$H NMR (CDCl$_3$) δ 7.83 (d, 1H), 7.31 (m, 5H), 6.94 (m, 1H), 5.70 (br, 1H), 4.29 (m, 1H), 3.52 (d, 2H), 3.41 (t, 2H), 2.68-2.52 (m, 3H), 1.73-1.56 (m, 4H), 1.33-1.21 (m, 8H), 0.93-0.87 (m, 6H) ppm.

EXPERIMENTAL EXAMPLES

For test results of the following Experimental Examples, the mark "#" is provided to denote significance with $p<0.05$ relative to a non-treated control, the mark "*" to denote significance with $p<0.05$ relative to a VEGF-stimulated HUVEC group, the mark "" to denote significance with $p<0.01$ relative to a VEGF-stimulated HUVEC group, the mark "*" to denote significance with $p<0.001$ relative to a VEGF-stimulated HUVEC group. These statistical significance levels were determined using ANOVA and Dunnett's post-hoc test.

Experimental Example 1

Cell Viability—MTS Assay

1) Method

A-431 (melanoma, human, ATCC CRL-1555™) cells grown in DMEM (Dulbeco's Modified Eagle's Medium, Gibco #11885) were seeded at a density of $1\times10^4$ cells/well into 96-well plates and incubated at 37° C. for 18 hrs under the supply of 5% $CO_2$ until the cells stably adhered to the bottom. The test substance sunitinib (synthesized by Boryung Pharmaceutical Synthesis Institute, S. Korea) (100, 50, 25, 12.5, 6.25, 3.125, 1.56, 0.78 μM), compounds of Chemical Formula I (100, 50, 25, 12.5, 6.25, 3.125, 1.56, 0.78 μM), and the control (medium) were serially diluted and applied to the 96-well plates. After incubation for 48 hrs in the presence of the test compound, the cells were assayed for viability.

The cells in each well was added with 21 μl of a mixture of 20:1 (v/v) of an MTS solution [(3-(4,5-dimethylthiazol-2-yl)-5-(3-carboxymethoxyphenyl)-2-(4-sulfophenyl)-2H-tetrazolium, Promega, Cat#65421; 2 mg/ml] and a PMS solution [Phenazine methosulfate, Sigma #P9625; 1 mg/ml], and incubated for 2 hrs, followed by measuring absorbance at 490 nm on a microplate reader (Molecular device, spectraMax M2). Relative to the control (media), viability by drug concentration was determined from the measurements of formazan, and the results are given in Table 2, below.

2) Results

Test Materials and their Concentrations:

Negative control: medium

Positive control: sunitinib, 100, 50, 25, 12.5, 6.25, 3.125, 1.56, 0.78 μM,

Compound of Chemical Formula I: 100, 50, 25, 12.5, 6.25, 3.125, 1.56, 0.78 μM.

TABLE 2

MTS Assay of Compounds of Chemical Formula I and Sunitinib for Cytotoxicity against Human Melanocyte (A-431)

| Test Compound | $IC_{50}$ (μM) |
| --- | --- |
| Control | — |
| Sunitinib | 22 |
| 103 | 40.6 |
| 104 | 28.6 |
| 110 | 22.2 |
| 111 | 135 |
| 117 | 91.1 |
| 201 | 54.5 |
| 208 | 86.1 |
| 241 | 164 |
| 242 | 81.9 |
| 243 | 170 |
| 244 | 94.6 |
| 246 | 100.7 |
| 249 | 102.5 |

TABLE 2-continued

MTS Assay of Compounds of Chemical Formula I and Sunitinib for Cytotoxicity against Human Melanocyte (A-431)

| Test Compound | $IC_{50}$ (μM) |
| --- | --- |
| 250 | 26.1 |
| 267 | 20.9 |
| 269 | 88.9 |
| 273 | 40.9 |
| 274 | 110.9 |
| 275 | 94.6 |
| 290 | 54.8 |
| 301 | 67.6 |
| 302 | 38.1 |
| 311 | 62.3 |
| 312 | 20.68 |
| 426 | 39.7 |
| 428 | 125 |
| 436 | 34 |
| 443 | 140 |
| 515 | 23.8 |
| 517 | 50.7 |

As can be seen in Table 2, compounds of Chemical Formula I have $IC_{50}$ values similar to or higher than that of sunitinib, an anticancer agent currently used for endstage renal cancer, demonstrating that they are of lower toxicity and higher safety.

Experimental Example 2

Suppressive Effect on VEGF-Induced Cell Migration in HUVECs 2-1. Transwell Assay 1) Method To examine the inhibitory effect of the compounds obtained in the Examples on VEGF (Vascular endothelial growth factor)-induced cell migration in HUVECs (human umbelical vein endothelial cells), a transwell assay was performed as follows.

HUVECs, provided from ATCC (American Type Culture Collection), were incubated in EGM-2 (Endothelial growth Medium-2 Medium) including 10% FBS, penicillin (100 unit/ml) and 100 μg/ml streptomycin sulfate plus various growth factors at 37° C. in an atmosphere of 5% $CO_2$. After the change of the medium with growth factor-free EBM-2 (Endothelial Basal Medium-2 Medium), the cells were subjected to transwell assay. Various concentrations of test compounds (Compounds 103, 110, 218, 275, 276, 290, 312, 428, 442 and 509, and sunitinib) in DMSO (dimethylsulfoxide) were added together with VEGF.

The HUVECs were seeded at a density of $2\times10^5$ cells/well to 24-transwell plates, and incubated with sunitinib (1 μM) and various concentrations of compounds of Chemical Formula I for 1 hr, and then for 24 hrs with 10 ng/ml VEGF, which functions to induce the growth and proliferation of cells.

After for 24 hours, the cells were fixed for 1 min with ethanol and were stained with a dye. Cell migration was evaluated by counting cells which moved through the pores.

In addition, cells were treated with Compound No. 250 (Example 26) at various concentrations given in Table 3, and assayed for cell migration, as conducted with Compounds 103, 110, 218, 273, 275, 276, 290, 312, 428, 442, and 509. The results were compared with those obtained after non-treatment (no treat) or treatment with 10 ng/mL VEGF.

2) Results

Results were expressed as average numbers (n=3) of HUVECs which moved cross the membrane. Test results are summarized in Table 3 for compounds 103, 110, 218, 273, 275, 276, 290, 312, 428, 442, and 509, and in Table 4 for compound 250.

TABLE 3

| Test Compound | No. of migration cells/field |
|---|---|
| No treat | 7 |
| VEGF treated control | 22[#] |
| 103 (0.1 μM) | 16*** |
| 103 (0.5 μM) | 12*** |
| 103 (1 μM) | 8*** |
| 110 (25 μM) | 10*** |
| 218 (25 μM) | 7.5*** |
| 273 (50 μM) | 12*** |
| 275 (50 μM) | 11*** |
| 276 (50 μM) | 12.5*** |
| 290 (50 μM) | 14.5*** |
| 312 (50 μM) | 14*** |
| 428 (25 μM) | 14.5*** |
| 442 (25 μM) | 15*** |
| 509 (25 μM) | 7*** |
| Sunitinib (1 μM) | 16.5*** |

TABLE 4

| Test Compound | No. of migration cells/field |
|---|---|
| no treat | 3.8 ± 1.29 |
| VEGF (10 ng/ml) | 42.5 ± 2.69[#] |
| VEGF + 250 (25 nM) | 33 ± 2.54** |
| VEGF + 250 (50 nM) | 20.3 ± 1.08*** |
| VEGF + 250 (100 nM) | 12.5 ± 2.5*** |
| 250 (100 nM) | 4.5 ± 1.11 |

As is apparent from the data of Tables 3 and 4, compounds of Chemical Formula I suppressed VEGF-induced migration of HUVECs. Compound 103 was, inter alia, more suppressive than the anticancer agent sunitinib in VEGF-induced migration of HUVECs. Moreover, Compound 250 showed a remarkable suppressive effect on the VEGF-induced HUVEC migration even at a low concentration.

2-2. Wound Healing Assay

1) Method

Using a sterile, disposable cell scraper (BD Falcon, Bedford, USA), a monolayer of HUVECs was scraped, and the cells were gently washed with PBS. The cells were treated with sunitinib (1 μM) or Compound 103 (0.1, 0.5, 1 μM) for 1 hr and then with 10 ng/ml VEGF for 24 hrs. After 24 hours, the cell migration were monitored through the scraped monolayer of the cell and photographed under a microscope equipped with a camera (Canon Powershot640).

Also, Compound 250 (Example 26) was applied at various concentrations shown in Table 6 in the same manner as Compound 103, followed by monitoring and photographing the migration of the cells under the microscope. For comparison, the cells were not treated (control) or were treated with 10 ng/mL VEGF, alone.

2) Results

Figure 2:
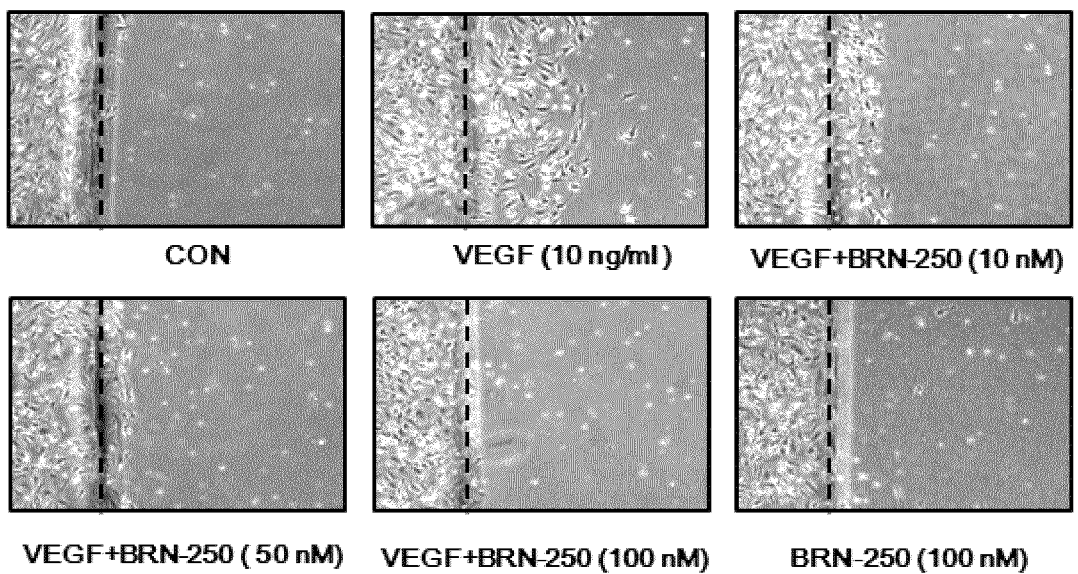
Figure 3:
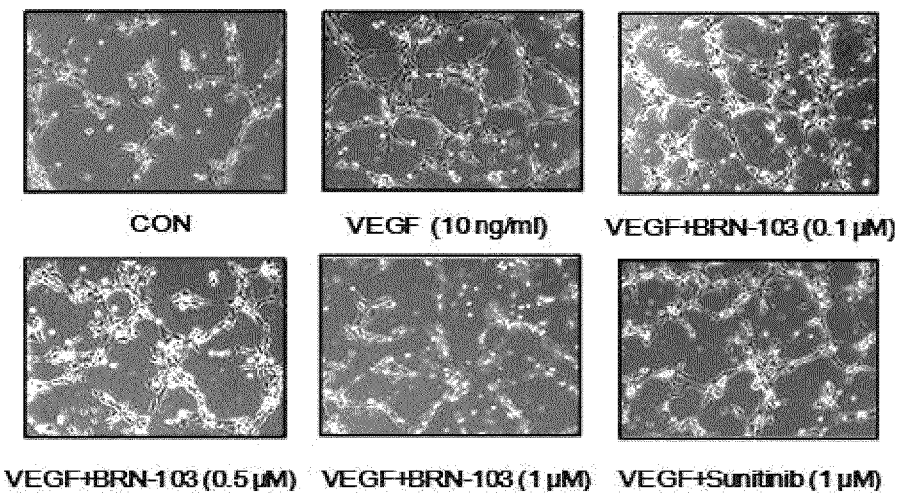
FIGS. 3 and 4 are photographs showing results of Experimental Example 4.

Results are shown in Table 5 and FIG. 1 for Compound 103 and in Table 6 and FIG. 2 for Compound 250.

TABLE 5

| Test Compound | Wound closure (μM) |
|---|---|
| Control | 110 |
| VEGF (10 ng/ml) | 380[#] |
| VEGF + 103 (0.1 μM) | 200*** |
| VEGF + 103 (0.5 μM) | 180*** |

TABLE 5-continued

| Test Compound | Wound closure (μM) |
|---|---|
| VEGF + 103 (1 μM) | 155*** |
| VEGF + Sunitinib (1 μM) | 210*** |

TABLE 6

| Test Compound | Wound Closure (μM) |
|---|---|
| Control | 120 |
| VEGF (10 ng/ml) | 290[#] |
| VEGF + 250 (25 nM) | 210** |
| VEGF + 250 (50 nM) | 165*** |
| VEGF + 250 (100 nM) | 120*** |
| 250 (100 nM) | 125 |

As illustrated in Table 5, it is confirmed that Compound 103 has the suppression effects on VEGF-induced migration of HUVECs and suppresses VEGF-induced migration of HUVECs at higher efficiency than sunitinib.

Also, as can be seen in Table 6, Compound 250 was highly suppresses VEGF-induced migration of HUVECs even at as low concentrations as nM levels.

Experimental Example 3

Suppressive Effect on VEGF-Induced Cell Proliferation in HUVECs (BrdU Incorporation Assay)

1) Method

A BrdU incorporation assay was carried out to examine whether the proliferation of HUVECs through VEGF-induced DNA synthesis is suppressed by BRN-103. HUVECs grown as in Experimental Example 2 were seeded at a density of $1 \times 10^4$ cells/well into 96-well plates. The cells were incubated with sunitinib (1 μM), or Compound 103 (0.1, 0.5, or 1 μM) for 1 hr and then with 10 ng/ml VEGF for 24 hrs. Thereafter, DNA synthesis in the cells was fluorescently measured using a BrdU incorporation assay kit (Roche).

Likewise, the cells were treated with various concentrations of Compound 250 (Example 26) given in Table 8, and then with VEGF, as the same manner of that of Compound 103. Intracellular DNA was also quantified, as the same manner of that of Compound 103. For comparison, the cells were not treated (control), or were treated with 10 ng/mL VEGF, alone.

2) Result

Results are given in Table 7 for Compound 103 and in Table 8 for Compound 250.

TABLE 7

| Test Compound | BrdU incorporation (OD 450 nm) |
|---|---|
| Control | 0.65 |
| VEGF (10 ng/ml) | 1.3[#] |
| VEGF + 103 (0.1 μM) | 1.0*** |
| VEGF + 103 (0.5 μM) | 0.8*** |
| VEGF + 103 (1 μM) | 0.7*** |
| 103 (1 μM) | 0.7 |
| VEGF + Sunitinib (1 μM) | 0.84*** |

TABLE 8

| Test Compound | BrdU incorporation (OD 450 nM) |
| --- | --- |
| Control | 0.65 ± 0.05 |
| VEGF (10 ng/ml) | 0.9 ± 0.01# |
| VEGF + 250 (25 nM) | 0.79 ± 0.02** |
| VEGF + 250 (50 nM) | 0.75 ± 0.03*** |
| VEGF + 250 (100 nM) | 0.7 ± 0.05*** |
| 250 (100 nM) | 0.7 ± 0.05 |

As can be seen in Table 7, Compound 103 of the present invention inhibited VEGF-induced proliferation in HUVECs in a dose-dependent manner. Compound 103 of the present invention showed higher efficacy than sunitinib.

As can be seen in Table 8, Compound 250 also inhibited VEGF-induced proliferation in HUVECs. Additionally, Compound 250 has excellent suppressive effects on VEGF-induced proliferation of HUVECs even at a very low concentration.

Experimental Example 4

Suppressive Effect on VEGF-Induced Tube Formation of HUVECs (Ex Vivo Capillary Structure Formation Assay)

1) Method

HUVECs were pretreated with sunitinib (1 µM) or Compound 103 (0.1, 0.5, or 1 µM) for 1 hr. After HUVECs were seeded at a density of $3 \times 10^5$ cells/well into Matrigel-coated 48-well plates, HUVECs were with 10 ng/ml VEGF for 4 hrs. The HUVECs where tubes were formed were monitored and photographed under a microscope equipped with a camera to count cells.

HUVECs were also treated with Compound 250 (Example 26) at various concentrations given in Table 10, The HUVECs where tubes were formed were monitored and photographed under a microscope equipped with a camera, like Compound 103.

2) Result

Figure 4:
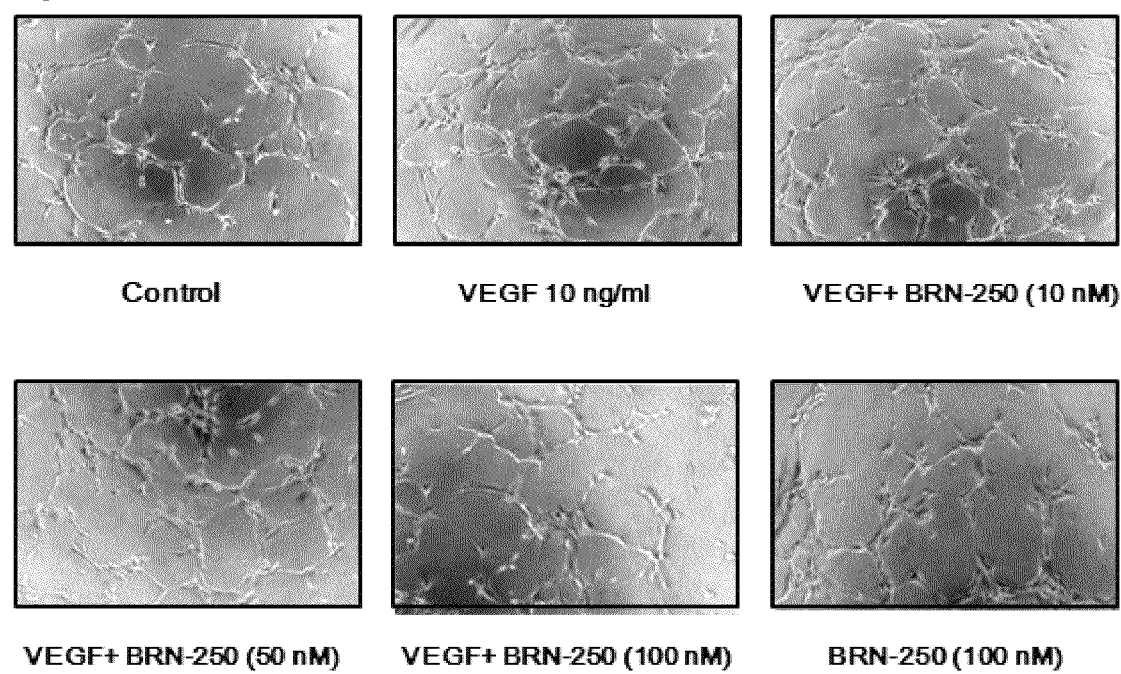

Results are summarized in FIG. 4 and in Table 9 for Compound 103 and shown in FIG. 4 and Table 10 for Compound 250.

TABLE 9

| Test Compound | Number of tubes/Field |
| --- | --- |
| Control | 50 |
| VEGF (10 ng/ml) | 140# |
| VEGF + 103 (0.1 µM) | 90** |
| VEGF + 103 (0.5 µM) | 80*** |
| VEGF + 103 (1 µM) | 60*** |
| VEGF + Sunitinib (1 µM) | 100*** |

TABLE 10

| Test Compound | Number of tubes/field |
| --- | --- |
| Control | 30 ± 5 |
| VEGF (10 ng/ml) | 60 ± 4# |
| VEGF + 250 (25 nM) | 45 ± 6** |
| VEGF + 250 (50 nM) | 35 ± 2*** |
| VEGF + 250 (100 nM) | 28 ± 4*** |
| 250 (100 nM) | 27 ± 2 |

As is apparent from data of Table 9, VEGF-induced tube formation was suppressed by Compound 103, indicating that the compound of the present invention blocks VEGF-induced angiogenesis. Also, Compound 103 was more efficient in the inhibition of tube formation than sunitinib.

As is apparent from data of Table 10, VEGF-induced tube formation was also suppressed by Compound 103, indicating that the compound of the present invention blocks VEGF-induced angiogenesis. Particularly, Compound 250 retains high suppressive effect on tube formation even at a low concentration.

Experimental Example 5

Suppressive Effect on VEGF-Induced Sprouting in Mouse Aorta 5-1 Ex Vivo Microvessel Sprouting Assay 1) Method Aortic rings excised from 5-week-old C57BL/6 mice were placed in Matrigel-coated 48-well plates, and incubated with sunitinib (1 µM) or Compound 103 (0.1, 0.5, 1 µM) for 1 hr and then with 10 ng/ml VEGF for 7 days. Sprouts from margins of the aortic rings were photographed under a microscope equipped with a camera.

Likewise, after the aortic rings excised from six-week-old Spague-Dawley rats were treated with various concentrations (10 nM, 50 nM, 100 nM) of Compound 250 (Example 26) and then with VEGF, Sprouts from margins of the aortic rings were photographed under a microscope equipped with a camera, like Compound 103.

2) Result

Figure 5:
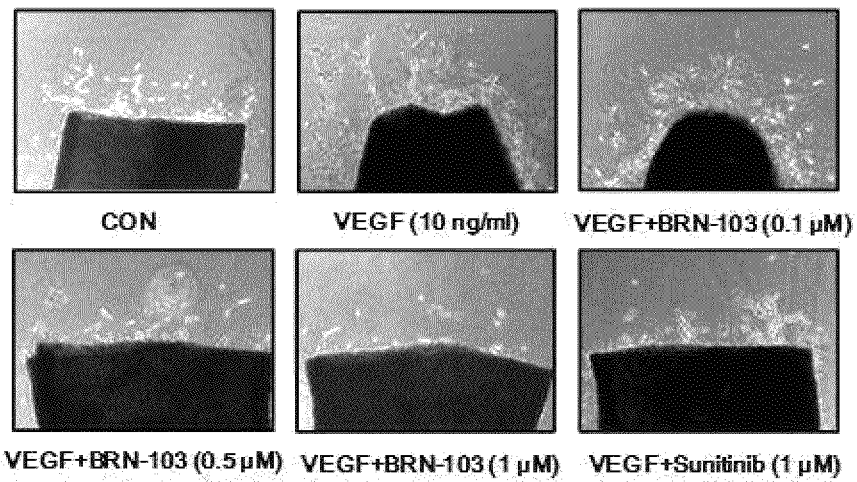
FIGS. 5 and 6 are photographs showing results of Experimental Example 5.
Figure 6:
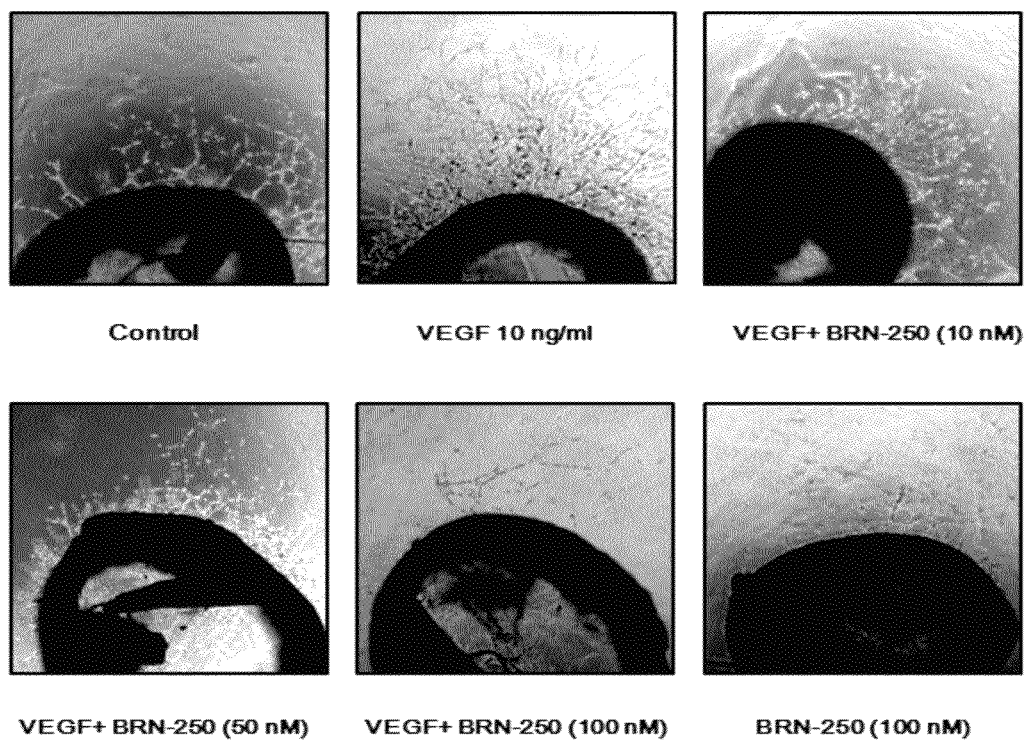

As is illustrated in FIGS. 5 and 6, Compounds 103 and 250 inhibited VEGF-induced aortic sprouting.

Particularly, it is confirmed that Compound 250 has effective, inhibitory activity against aortic sprouting even at as low concentrations as nM levels.

Experimental Example 6

Inhibitory Effect on VEGF-Induced VEGFR2 Activation in HUVECs (Western Blot Analysis)

1) Method

An examination was made to see the effect of compounds of Chemical Formula I on VEGF-induced VEGFR2 activation, as follows.

HUVECs were pretreated for 1 hr with sunitinib (1 µM) or Compound 103 (0.1, 0.5, 1 µM) and then treated with VEGF (10 ng/ml) of 5 min. After 3 min of centrifugation at 4000 rpm to collect the cells, the cell pellet was washed once with PBS (phosphate buffered saline). The washed cell pellet was suspended in a lysis buffer (50 mM HEPES pH 7.0, 250 mM NaCl, 5 mM EDTA, 0.1% Nonidet P-40, 1 mM phenylmethylsulfonyl fluoride and 0.5 mM Na orthovanadate) containing 5 µl/mL of leupeptin and aprotinin, each and reaction was performed at 4° C. for 20. After the cell debris was removed by microcentrifugation, the supernatant was swiftly cooled, and quantified for protein level using a Bio-Rad protein assay reagent. Forty µg of the cell protein from each test group was run by 10% SDS-PAGE, and transferred onto a PVDF membrane.

For immunoblotting, the membrane was incubated overnight at 4° C. in a blocking solution (5% skim milk), and reacted with a primary antibody for 4 hrs. After 4 washes with Tween 20/Tris-buffered saline (TTBS), the membrane was reacted with a 1:1000 (v/v) dilution of a horseradish peroxidase-conjugated secondary antibody at room temperature for 1 hr, washed three times with TTBS, and identified by a chemical luminescence method (Amersham Life Science).

As with Compound 103, HUVECs were treated with various concentrations (10 nM, 50 nM, 100 nM) of Compound 250 (Example 26) and then with VEGF, and analyzed for inhibitory activity against VEGF-induced VEGFR2 activation.

2) Result

Figure 7:
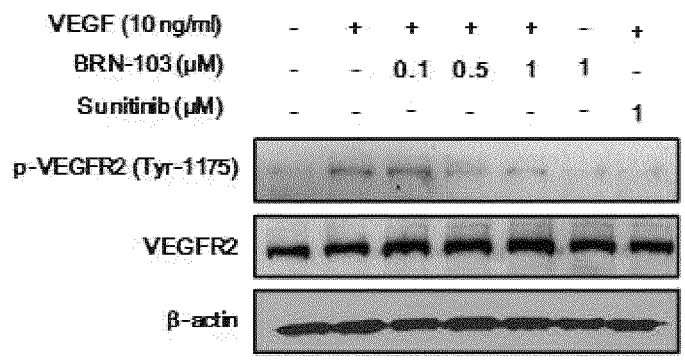
FIGS. 7 and 8 are photographs showing results of Experimental Example 6.
Figure 8:
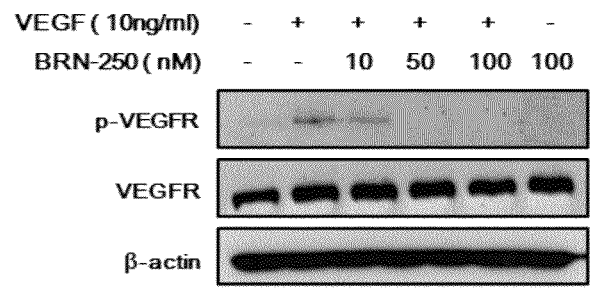

Results are given in FIG. 7 for Compound 103 and in FIG. 8 for Compound 250.

In FIGS. 7 and 8, the mark "−" denotes the absence of the corresponding ingredients listed left while the mark "+" denotes the presence of the corresponding ingredients listed left. As can be seen in FIGS. 7 and 8, VEGF induced the expression of p-VEGFR (Tyr-1175) whereas compounds of Chemical Formula I, like sunitibib, inhibited the expression of p-VEGFR (Tyr-1175). Accordingly, 6-HMA is found to inhibit the production of $PGE_2$ by down-regulating the expression of COX-2, a $PGE_2$ synthase. Therefore, compounds of Chemical Formula I according to the present invention act against the VEGFR2 pathway which has important influences on the migration and proliferation of cells.

Experimental Example 7

Inhibitory Effect on VEGF-Induced AKT/ERK and eNOS Activation in HUVECs (Western Blot Analysis)

1) Method

An examination was made to see the effect of compounds of Chemical Formula I, prepared in the Examples above, on VEGF-induced activation of AKT (serine/threonine protein kinase B)/ERK (Extracellular signal-regulated kinases) and eNOS (endothelial nitric oxide synthase) in HUVECs, as follows (endothelial nitric oxide synthase).

HUVECs were pretreated for 1 hr with sunitinib (1 µM) or Compound 103 (0.1, 0.5, 1 µM) and then treated with VEGF (10 ng/ml) for 10 min (p-ERK), 30 min (p-AKT), and 1 hr (p-eNOS). After 3 min of centrifugation at 4000 rpm to collect the cells, the cell pellet was washed once with PBS (phosphate buffered saline). The cell pellet suspended in a lysis buffer (50 mM HEPES pH 7.0, 250 mM NaCl, 5 mM EDTA, 0.1% Nonidet P-40, 1 mM phenylmethylsulfonyl fluoride and 0.5 mM Na orthovanadate) containing 5 µl/mL of leupeptin and aprotinin, each and the reaction was performed at 4° C. for 20 min. After the cell debris was removed by microcentrifugation, the supernatant was swiftly cooled.

Protein quantification was carried out using a Bio-Rad protein assay reagent. Forty µg of the cell protein from each test group was run by 10% SDS-PAGE, and transferred onto a PVDF membrane.

For immunoblotting, the membrane was incubated overnight at 4° C. in a blocking solution (5% skim milk), and reacted with a primary antibody for 4 hrs. After 4 washes with Tween 20/Tris-buffered saline (TTBS), the membrane was reacted with a 1:1000 (v/v) dilution of a horseradish peroxidase-conjugated secondary antibody at room temperature for 1 hr, washed three times with TTBS, and visualized by a chemical luminescence method (Amersham Life Science). Of measurements from three independent experiments, a representative is shown in FIG. 5.

2) Result

Figure 9:
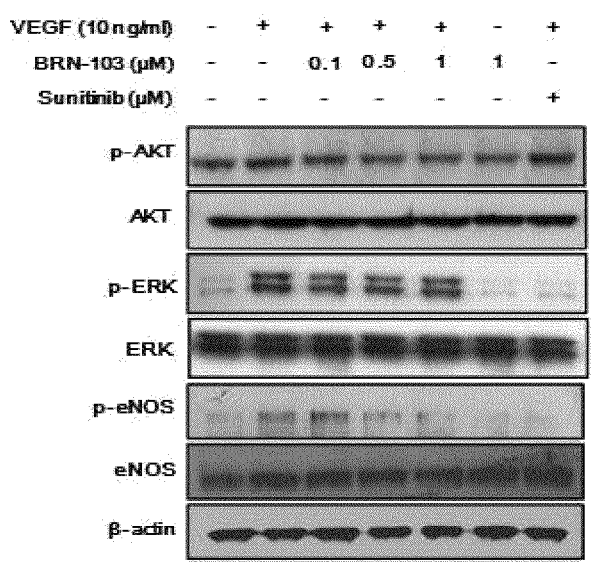
FIG. 9 is a photograph showing results of Experimental Example 7.

In FIG. 9, the mark "−" denotes the absence of the corresponding ingredients listed left while the mark "+" denotes the presence of the corresponding ingredients listed left. As can be seen in FIG. 5, VEGF induced the expression of p-ERK at 10 min and p-AKT at 30 min. Compound 103 decreased the expression of p-AKT, but did not suppress the expression of p-ERK. In contrast, sunitinib was observed to decrease levels of both p-AKT and p-ERK. In addition, p-eNOS, a factor downstream of AKT and ERK, was downregualted in both the groups treated with Compound 103 or sunitinib. Consequently, compounds of Chemical Formula I according to the present invention inhibit the migration and proliferation of cells by downregulating eNOS, which is involved in cell migration and proliferation in HUVECs, in a different pathway from that of sunitinib.

The invention claimed is:

1. A compound of Chemical Formula I, or a pharmaceutically acceptable salt thereof:

[Chemical Formula I]

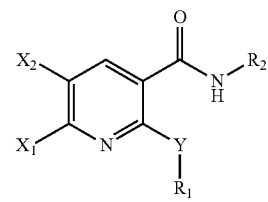

wherein, $X_1$ and $X_2$ are independently a halogen atom selected from the group consisting of F, Cl, Br, and I, or a hydrogen atom, Y is —NH—; —S—; or —O—, $R_1$ is piperidinyl, piperazinyl, azabicyclo[2.2.2]octanyl, or phenyl, each independently having 1 to 5 substituents selected from the group consisting of benzyl, phenyloxy, 1-pyrimidinylethyl, pyridine methyl, $C_{1-4}$ alkyl, $C_{3-6}$ alkene, t-butoxycarboxyl, and malon-2-yl; 1-azabicyclo [2.2.2]oct-3-yl; piperidin-4-yl; piperidin-3-yl; or 1-(6-chloro-5-fluoropyrimidin-4-yl)ethyl piperidin-4-yl, wherein the $C_{1-4}$ alkyl is substituted with 0 to 3 substituents selected from the group consisting of $R_3R_4N$—, hydroxyl, and a halogen atom, wherein $R_3$ and $R_4$ are each independently a $C_{1-4}$ alkyl, wherein the benzyl, the phenyloxy, the pyrimidinylethyl and the pyridine methyl are independently substituted with 0 to 4 halogen atoms, $R_2$ is $C_{1-4}$ alkyl with 1 or 2 substituents selected from the group consisting of morpholinyl substituted with 0 to 3 benzyl groups having 0 to 3 halogen substituents, phenyl substituted with 0 to 3 halogen atoms, pyridinyl, pyrimidinyl, piperidinyl and piperazinyl; $C_{5-10}$ alkyl; $C_{1-4}$ alkyloxycarbonylamino; $C_{1-4}$alkoxy$C_{1-4}$alkyl; toluenesulfonamino; phenyl with 0 to 3 substituents selected from the group consisting of $C_{1-4}$ alkyl, halogen, nitro and phenoxy; (3,4-dimethoxy)phenyl; pyridinyl with 0 to 3 substituents selected from the group consisting of $C_{1-4}$ alkyloxycarbonyl and $C_{1-4}$ alkyl; azepan-2-onyl; 1,3,4-triazolyl; pyrimidinyl substituted with 0 to 3 $C_{1-4}$ alkyl groups; pyrrolidinyl; thiazolyl substituted with 0 to 2 $C_{1-4}$ alkyl groups; 2,3-dihydroxy indole substituted with 0 to 3 $C_{1-4}$ alkyl groups;

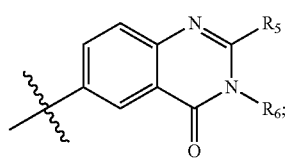

-continued

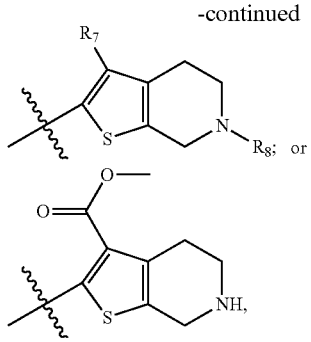

wherein $R_5$ and $R_6$ are each independently $C_{1-4}$alkyl, $C_{1-4}$alkyl sulfanyl or thiol, and $R_7$ and $R_8$ are each independently $C_{1-4}$ alkyloxycarbonyl, phenyl or benzyl.

2. The compound or the pharmaceutically acceptable salt thereof according to claim 1, wherein $R_1$ is 1-benzylpiperidin-4-yl; 1-benzylpiperidin-3-yl; 4-phenoxyphenyl; 1-(2-hydroxyethyl)-piperidine-4-yl; 1-(2-hydroxyethyl)-piperidin-3-yl; 1-(2-hydroxyethyl)-piperazin-4-yl; 2,2,6,6-tetramethylpiperidine-4-yl; t-butoxycarbonylpiperidin-4-yl; t-butoxycarbonylpiperidin-3-yl; 1-azabicyclo[2.2.2]oct-3-yl; methylpiperidin-4-yl; methylpiperazin-4-yl; piperidin-4-yl; piperidin-3-yl; 1-(2-hydroxyethyl)-2,2,6,6-tetramethylpiperidin-4-yl; 1-allylic piperidin-4-yl; [2-(N,N-dimethylamino)ethyl]piperidine-4-yl; (t-butyloxycarbonyl) piperidin-3-yl; (malon-2-yl)piperidin-4-yl; (pyridin-2-yl) methylpiperidin-4-yl; (pyridin-3-yl)methylpiperidin-4-yl; or 1-(6-chloro-5-fluoropyrimidin-4-yl)ethyl piperidin-4-yl.

3. The compound or the pharmaceutically acceptable salt thereof according to claim 2, wherein $R_1$ is 1-(6-chloro-5-fluoropyrimidin-4-yl)ethyl piperidin-4-yl, 1-benzylpiperidin-4-yl; 1-benzylpiperidin-3-yl; 1-(2-hydroxyethyl)-piperidin-4-yl; piperidin-3-yl; or t-butoxycarbonylpiperidin-3-yl.

4. The compound or the pharmaceutically acceptable salt thereof according to claim 1, wherein $R_2$ is 3-chlorophenyl; 4-phenoxyphenyl; 3,3-dimethyl-2,3-dihydro-1H-indol-6-yl; 4-(4-fluorobenzyl)-morpholin-2-ylmethyl; 1,3,4-triazol-2-yl; 4,6-dimethylpyrimidin-2-yl; (S)-pyrrolidin-3yl; 2-(morpholin-1-yl)ethyl; t-butoxycarbonylamino; (3-methoxycarbonyl)pyridin-6-yl; p-toluenesulfonamino; pyridine-4-ylmethyl; 1,2-diphenylethyl; 2-methoxyethyl; 5-methylthiazol-2-yl; 3-methylpyridin-2-yl; azepan-2-on-3-yl; 4-fluorobenzyl; 2-ethylhexyl; 3-methyl-2-methylsulfanyl-3,4-dihydroquinazolin-4-on-6-yl; (3,4-dimethoxy)phenyl;

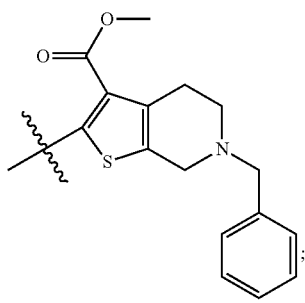

-continued

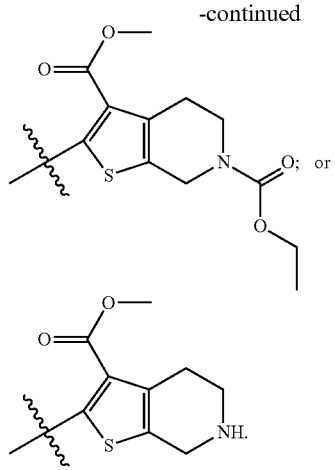

5. The compound or the pharmaceutically acceptable salt thereof according to claim 4, wherein $R_2$ is 3-chlorophenyl; 4-phenoxyphenyl; 5-methylthiazol-2-yl; or

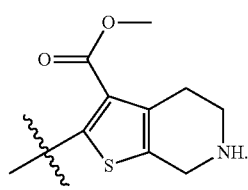 [SMILES: *c1sc2c(c1C(=O)OC)CCNC2]

6. The compound or the pharmaceutically acceptable salt thereof according to claim 1, being selected from the group consisting of:
2-(1-benzylpiperidin-4-ylamino)-N-(3-chlorophenyl) nicotinamide [103],
N-(3-chlorophenyl)-2-(4-phenoxyanilino)nicotinamide [104],
2-(1-benzylpiperidin-4-ylamino)-N-(4-phenoxyphenyl) nicotinamide [110],
2-(4-phenoxyanilino)-N-(4-phenoxyphenyl)nicotinamide [111],
N-(3-chlorophenyl)-2-(2,2,6,6-tetramethylpiperidin-4-ylamino)nicotinamide [201],
N-(3-chlorophenyl)-2-(1-tert-butoxycarbamoylpiperidin-4-ylamino)nicotinamide [208],
2-(1-azabicyclo[2.2.2]oct-3-ylamino)-N-(3-chlorophenyl)nicotinamide [210],
N-(3-chlorophenyl)-2-(1-methylpiperidin-4-ylamino) nicotinamide [214],
N-(3-chlorophenyl)-2-[1-(2-hydroxyethyl)piperidin-4-ylamino]nicotinamide [218],
N-(3-chlorophenyl)-2-(4-methylpiperazin-1-ylamino) nicotinamide [240],
N-(3-chlorophenyl)-2-[4-(2-hydroxyethyl)piperazin-1-ylamino)nicotinamide [241],
(R)-2-(1-benzylpiperidin-3-ylamino)-N-(3-chlorophenyl) nicotinamide [267],
(S)-2-(1-benzylpiperidin-3-ylamino)-N-(3-chlorophenyl) nicotinamide [273],
(R)—N-(3-chlorophenyl)-2-(1-tert-butoxycarbamoylpiperidin-3-ylamino)nicotinamide [270],
(S)—N-(3-chlorophenyl)-2-(1-tert-butoxycarbamoylpiperidin-3-ylamino)nicotinamide [276], 2-(1-benzylpiperidin-4-ylamino)-6-chloro-N-(3-chlorophenyl)nicotinamide [301],
2-(1-benzylpiperidin-4-ylamino)-6-chloro-N-(3-chlorophenyl)-5-fluoronicotinamide [302],
6-chloro-N-(3-chlorophenyl)-2-[1-(2-hydroxyethyl)benzylpiperidin-4-ylamino]nicotinamide [311],
6-chloro-N-(3-chlorophenyl)-5-fluoro-2-[1-(2-hydroxyethyl)piperidin-4-ylamino]nicotinamide [312],
2-(1-benzylpiperidin-4-ylamino)-N-(3,3-dimethyl-2,3-dihydro-1H-indol-6-yl)nicotinamide [117],
N-(3,3-dimethyl-2,3-dihydro-1H-indol-6-yl)-2-(4-phenoxyanilino)nicotinamide [118],
N-(3-chlorophenyl)-2-(4-piperidylamino)nicotinamide [224],
(R)—N-(3-chlorophenyl)-2-(3-piperidylamino)nicotinamide [269],
(S)—N-(3-chlorophenyl)-2-(3-piperidylamino)nicotinamide [275],
N-(3-chlorophenyl)-2-(1-(2-hydroxyethyl)-2,2,6,6-tetramethylpiperidin-4-ylamino)nicotinamide [242],
2-(1-allylic piperidin-4-ylamino)-N-(3-chlorophenyl)nicotinamide [243],
N-(3-chlorophenyl)-2-[1-(2-N,N-diethylamino-ethyl)piperidin-4-ylamino]nicotinamide [244],
N-(3-chlorophenyl)-2-[1-(pyridin-2-ylmethyl)piperidin-4-ylamino]nicotinamide [248],
N-(3-chlorophenyl)-2-[1-(pyridin-3-ylmethyl)piperidin-4-ylamino]nicotinamide [249],
2-{1-[1-(6-chloro-5-fluoropyrimidin-4-yl)ethyl]piperidin-4-ylamino}-N-(3-chlorophenyl)nicotinamide [250],
(R)—N-(3-chlorophenyl)-2-[1-(2-hydroxyethyl)piperidin-3-ylamino]nicotinamide [268],
(S)—N-(3-chlorophenyl)-2-[1-(2-hydroxyethyl)piperidin-3-ylamino]nicotinamide [274],
2-(4-(3-(3-chlorophenylcarbamoyl)pyridin-2-ylamino)piperidin-1-yl)malonic acid [246],
2-(1-benzylpiperidin-4-yloxy)-N-(3-chlorophenyl)nicotinamide [289],
2-(1-benzylpiperidin-4-ylsulfanyl)-N-(3-chlorophenyl)nicotinamide [290],
2-(1-benzylpiperidin-4-ylamino)-N-[4-(4-fluorobenzyl)morpholin-2-ylmethyl]nicotinamide [404],
2-(1-benzylpiperidin-4-ylamino)-N-(1,3,4-triazol-2-yl)nicotinamide [406],
2-(1-benzylpiperidin-4-ylamino)-N-(4,6-dimethylpyrimidin-2-yl)nicotinamide [407],
2-(1-benzylpiperidin-4-ylamino)-N—(S)-pyrrolidin-3-ylnicotinamide [408],
2-(1-benzylpiperidin-4-ylamino)-N-2-(morpholin-1-yl)ethylnicotinamide [409],
N'-[2-(1-benzylpiperidin-4-ylamino)pyridine-3-carbonyl]hydrazine carboxylic acid tert-butyl ester [410],
methyl 6-{[2-(1-benzylpiperidin-4-ylamino)pyridine-3-carbonyl]amino}nicotinate [412],
2-(1-benzylpiperidin-4-ylamino)-N-(para-toluenesulfonamino)nicotinamide [424],
2-(1-benzylpiperidin-4-ylamino)-N-(pyridin-4-ylmethyl)nicotinamide [425],
2-(1-benzylpiperidin-4-ylamino)-N-(1,2-diphenylethyl)nicotinamide [426],
2-(1-benzylpiperidin-4-ylamino)-N-(2-methoxyethyl)nicotinamide [427],
2-(1-benzylpiperidin-4-ylamino)-N-(5-methylthiazol-2-yl)nicotinamide [428],
2-(1-benzylpiperidin-4-ylamino)-N-(3-methylpyridin-2-yl)nicotinamide [429],
2-(1-benzylpiperidin-4-ylamino)-N-(azepan-2-on-3-yl)nicotinamide [430],
2-(1-benzylpiperidin-4-ylamino)-N-(4-fluorobenzyl)nicotinamide [431],
2-(1-benzylpiperidin-4-ylamino)-N-(2-ethylhexyl)nicotinamide [436],
2-(1-benzylpiperidin-4-ylamino)-N-(3-methyl-2-methylsulfanyl-3,4-dihydroquinazolin-4-on-6-yl)nicotinamide [439],
6-benzyl-2-{[2-(1-benzylpiperidin-4-ylamino)pyridine-3-carbonyl]amino}-4,5,6,7-tetrahydro-thieno[2,3-c]pyridine-3-carboxylic acid methyl ester [440],
6-ethoxycarbamate-2-{[2-(1-benzylpiperidin-4-ylamino)pyridine-3-carbonyl]amino}-4,5,6,7-tetrahydro-thieno[2,3-c]pyridine-3-carboxylic acid methyl ester [441],
2-{[2-(1-benzylpiperidin-4-ylamino)pyridine-3-carbonyl]amino}-4,5,6,7-tetrahydro-thieno[2,3-c]pyridine-3-carboxylic acid methyl ester [442],
2-(1-benzylpiperidin-4-ylamino)-N-(3,4-dimethoxyphenyl)nicotinamide [443],
2-{[2-(1-benzylpiperidin-4-ylamino)-6-chloropyridine-3-carbonyl]amino})-4,5,6,7-tetrahydrothieno[2,3-c]pyridine-3-carboxylic acid methyl ester [501],
2-{[2-(1-benzylpiperidin-4-ylamino)-6-chloropyridine-3-carbonyl]amino}-4,5,6,7-tetrahydrothieno[2,3-c]pyridine-3-carboxylic acid methyl ester [502],
2-{[2-(1-(2-hydroxyethyl)piperidin-4-ylamino)pyridine-3-carbonyl]amino}-4,5,6,7-tetrahydrothieno[2,3-c]pyridine-3-carboxylic acid methyl ester [503],
2-{[6-chloro-2-(1-(2-hydroxyethyl)piperidin-4-ylamino)pyridine-3-carbonyl]amino}-4,5,6,7-tetrahydrothieno[2,3-c]pyridine-3-carboxylic acid methyl ester [504],
2-{[6-chloro-5-fluoro-2-(1-(2-hydroxyethyl)piperidin-4-ylamino)pyridine-3-carbonyl]amino}-4,5,6,7-tetrahydrothieno[2,3-c]pyridine-3-carboxylic acid methyl ester [505],
2-{[2-(2,2,6,6-tetramethylpiperidin-4-ylamino)pyridine-3-carbonyl]amino}-4,5,6,7-tetrahydrothieno[2,3-c]pyridine-3-carboxylic acid methyl ester [506],
2-{[2-(2,2,6,6-tetramethylpiperidin-4-ylamino)6-chloropyridine-3-carbonyl]amino}-4,5,6,7-tetrahydrothieno[2,3-c]pyridine-3-carboxylic acid methyl ester [507],
2-{[6-chloro-5-fluoro-2-(2,2,6,6-tetramethylpiperidin-4-ylamino)pyridine-3-carbonyl]amino}-4,5,6,7-tetrahydrothieno[2,3-c]pyridine-3-carboxylic acid methyl ester [508],
2-{[2-(1-benzylpiperidin-3-ylamino)pyridine-3-carbonyl]amino}-4,5,6,7-tetrahydrothieno[2,3-c]pyridine-3-carboxylic acid methyl ester [509],
2-{[2-(1-benzylpiperidin-3-ylamino)-6-chloropyridine-3-carbonyl]amino}-4,5,6,7-tetrahydrothieno[2,3-c]pyridine-3-carboxylic acid methyl ester [510],
2-{[2-(1-benzylpiperidin-3-ylamino)-6-chloro-5-fluoropyridine-3-carbonyl]amino}-4,5,6,7-tetrahydrothieno[2,3-c]pyridine-3-carboxylic acid methyl ester [511],
6-chloro-N-(2-ethylhexyl)-2-[1-(2-hydroxyethyl)piperidin-4-ylamino]nicotinamide [515],
N-(2-ethylhexyl)-2-(2,2,6,6-tetramethylpiperidin-4-ylamino)nicotinamide [517],
6-chloro-N-(2-ethylhexyl)-5-fluoro-2-(2,2,6,6-tetramethyl piperidin-4-ylamino)nicotinamide [519],
2-(1-benzylpiperidin-3-ylamino)-N-(2-ethylhexyl)nicotinamide [520],
2-(1-benzylpiperidin-3-ylamino)-6-chloro-N-(2-ethylhexyl)-5-fluoronicotinamide [522], and pharmaceutically acceptable salts thereof.

7. The compound or the pharmaceutically acceptable salt according to claim 6, being selected from the group consisting of:
2-(1-benzylpiperidin-4-ylamino)-N-(3-chlorophenyl) nicotinamide [103],
2-(1-benzylpiperidin-4-ylamino)-N-(4-phenoxy phenyl) nicotinamide [110],
N-(3-chlorophenyl)-2-[1-(2-hydroxyethyl)piperidin-4-ylamino]nicotinamide [218],
2-{1-[1-(6-chloro-5-fluoropyrimidin-4-yl)ethyl]piperidin-4-ylamino}-N-(3-chlorophenyl)nicotinamide [250],
(S)-2-(1-benzylpiperidin-3-ylamino)-N-(3-chlorophenyl) nicotinamide [273],
(S)—N-(3-chlorophenyl)-2-(1-tert-butoxycarbamoylpiperidin-3-ylamino)nicotinamide [276],
6-chloro-N-(3-chlorophenyl)-5-fluoro-2-[1-(2-hydroxyethyl)piperidin-4-ylamino]nicotinamide [312],
(S)—N-(3-chlorophenyl)-2-(3-piperidylamino)nicotinamide [275],
2-(1-benzylpiperidin-4-ylsulfanyl)-N-(3-chlorophenyl) nicotinamide [290],
2-(1-benzylpiperidin-4-ylamino)-N-(5-methylthiazol-2-yl)nicotinamide [428],
2-{[2-(1-benzylpiperidin-4-ylamino)pyridine-3-carbonyl]amino}-4,5,6,7-tetrahydro-thieno[2,3-c]pyridine-3-carboxylic acid methyl ester [442],
2-{[2-(1-benzylpiperidin-3-ylamino)pyridine-3-carbonyl]amino}-4,5,6,7-tetrahydrothieno[2,3-c]pyridine-3-carboxylic acid methyl ester [509], and pharmaceutically acceptable salts thereof.

8. The compound or the pharmaceutically acceptable salt thereof according to claim 7, being 2-(1-benzylpiperidin-4-ylamino)-N-(3-chlorophenyl)nicotinamide [103] or a pharmaceutically acceptable salt thereof.

9. A method for preparing a compound of claim 1, comprising reacting a compound of Chemical Formula II, with a compound of Chemical Formula III, in the presence of a base;

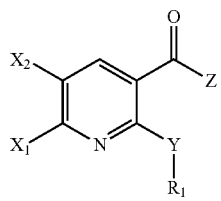

[Chemical Formula II]

[Chemical Formula III]

wherein,
X$_1$, X$_2$, R$_1$, and R$_2$ are respectively as defined in claim 1, and
Z is chloro or bromo.

10. The method of claim 9, wherein the base is selected from the group consisting of triethylamine, N,N-diisopropylethylamine, N-methylmorpholine, DBU (1,8-Diazabicyclo[5.4.0]undec-7-ene), N-methylpiperidine, 4-dimethylaminopyridine, N,N-dimethylaniline, 2,6-lutidine, 4-N,N-dimethylaminopyridine and pyridine.

11. The method of preparing the compound, represented by Chemical Formula I, of claim 1, comprising reacting a compound, represented by the following Chemical Formula IV, with a compound, represented by the following Chemical Formula V, in the presence of a base:

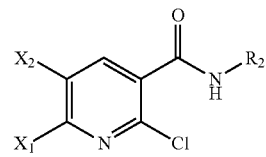

[Chemical Formula IV]

[Chemical Formula V]

wherein,
X$_1$, X$_2$, R$_1$, and R$_2$ are respectively as defined in claim 1, and
Y is —NH$_2$, —SH or —OH.

12. The method of claim 11, wherein the base is selected from the group consisting of potassium carbonate, potassium hydrogen carbonate, sodium carbonate, sodium hydrogen carbonate, sodium hydroxide, potassium hydroxide, calcium hydroxide, barium hydroxide, sodium methoxide, sodium ethoxide, sodium-t-butoxide, potassium-t-butoxide, sodium hydride, potassium hydride, sodium borohydride, sodium cyanoborohydride, and 4-N,N-dimethylaminopyridine.

13. The method of claim 11, wherein the reacting is carried out in xylene.

14. The method of claim 13, wherein the xylene is o-xylene.

15. A method for treating a disease or symptom caused by aberrant activity of vascular endothelial growth factor (VEGF), comprising administering a compound, represented by the following Chemical Formula I, or a pharmaceutically acceptable salt thereof to a subject:

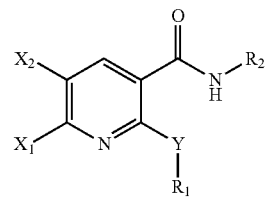

[Chemical Formula I]

wherein,
X$_1$ and X$_2$ are independently a halogen atom selected from the group consisting of F, Cl, Br, and I, or a hydrogen atom,
Y is —NH—; —S—; or —O—,
R$_1$ represents piperidinyl, piperazinyl, azabicyclo[2.2.2]octanyl, or phenyl, each independently having 1 to 5 substituents selected from the group consisting of benzyl, phenyloxy, 1-pyrimidinylethyl, pyridine methyl, C$_{1-4}$ alkyl, C$_{3-6}$ alkene, t-butoxycarboxyl, and malon-2-yl; 1-azabicyclo[2.2.2]oct-3-yl; piperidin-4-yl; piperidin-3-yl; or 1-(6-chloro-5-fluoropyrimidin-4-yl)ethyl piperidin-4-yl,
wherein the C$_{1-4}$ alkyl is substituted with 0 to 3 substituents selected from among R$_3$R$_4$N—, hydroxyl, and a halogen atom, wherein R$_3$ and R$_4$ are independently a C$_{1-4}$ alkyl,
wherein the benzyl, the phenyloxy, the pyrimidinylethyl and the pyridine methyl are independently substituted with 0 to 4 halogen atoms, $R_2$ represents $C_{1-4}$ alkyl with 1 or 2 substituents selected from among morpholinyl substituted with 0 to 3 benzyl groups having 0 to 3 halogen substituents, phenyl substituted with 0 to 3 halogen atoms, pyridinyl, pyrimidinyl, piperidinyl and piperazinyl; $C_{5-10}$ alkyl; $C_{1-4}$ alkyloxycarbonylamino; $C_{1-4}$alkoxy$C_{1-4}$ alkyl; toluenesulfonamino; phenyl with 0 to 3 substituents selected from among $C_{1-4}$ alkyl, halogen, nitro and phenoxy; (3,4-dimethoxy)phenyl; pyridinyl with 0 to 3 substituents selected from among $C_1$-4 alkyloxycarbonyl and $C_1$-4 alkyl; azepan-2-onyl; 1,3,4-triazolyl; pyrimidinyl substituted with 0 to 3 $C_1$-4 alkyl groups; pyrrolidinyl; thiazolyl substituted with 0 to 2 $C_1$-4 alkyl groups; 2,3-dihydroxy indole substituted with 0 to 3 $C_{1-4}$ alkyl groups;

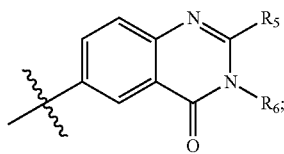

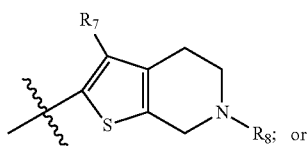

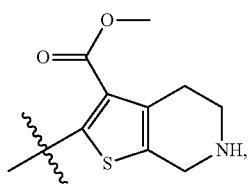

wherein $R_5$ and $R_6$ are each independently $C_{1-4}$alkyl, $C_{1-4}$alkyl sulfanyl or thiol, and $R_7$ and $R_8$ are each independently $C_{1-4}$ alkyloxycarbonyl, phenyl or benzyl, wherein the disease or symptom is selected from the group consisting of cancer, rheumatoid arthritis, diabetic retinopathy, keratitis, macular degeneration, choroidal neovascularization, neovascular glaucoma, ophthalmic diseases of corneal neovascularization, psoriasis and obesity by angiogenesis.

16. A method for inhibiting an activity of vascular endothelial growth factor (VEGF), comprising administering a compound, represented by the following Chemical Formula I, or a pharmaceutically acceptable salt thereof to a subject:

[Chemical Formula I]

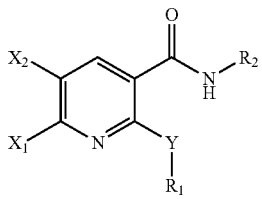

wherein, $X_1$ and $X_2$ are independently a halogen atom selected from the group consisting of F, Cl, Br, and I or a hydrogen atom, Y is —NH—; —S—; or —O—, $R_1$ represents piperidinyl, piperazinyl, azabicyclo[2.2.2]octanyl, or phenyl, each independently having 1 to 5 substituents selected from the group consisting of benzyl, phenyloxy, 1-pyrimidinylethyl, pyridine methyl, $C_{1-4}$ alkyl, $C_{3-6}$ alkene, t-butoxycarboxyl, and malon-2-yl; 1-azabicyclo[2.2.2]oct-3-yl; piperidin-4-yl; piperidin-3-yl; or 1-(6-chloro-5-fluoropyrimidin-4-yl)ethyl piperidin-4-yl, wherein the $C_{1-4}$ alkyl is substituted with 0 to 3 substituents selected from among $R_3R_4N$—, hydroxyl, and a halogen atom, wherein $R_3$ and $R_4$ are independently a $C_{1-4}$ alkyl, wherein the benzyl, the phenyloxy, the pyrimidinylethyl and the pyridine methyl are independently substituted with 0 to 4 halogen atoms, $R_2$ represents $C_{1-4}$ alkyl with 1 or 2 substituents selected from the group consisting of morpholinyl substituted with 0 to 3 benzyl groups having 0 to 3 halogen substituents, phenyl substituted with 0 to 3 halogen atoms, pyridinyl, pyrimidinyl, piperidinyl and piperazinyl; $C_{5-10}$ alkyl; $C_{1-4}$ alkyloxycarbonylamino; $C_{1-4}$alkoxy$C_{1-4}$ alkyl; toluenesulfonamino; phenyl with 0 to 3 substituents selected from among $C_{1-4}$ alkyl, halogen, nitro and phenoxy; (3,4-dimethoxy)phenyl; pyridinyl with 0 to 3 substituents selected from among $C_{1-4}$ alkyloxycarbonyl and $C_{1-4}$ alkyl; azepan-2-onyl; 1,3,4-triazolyl; pyrimidinyl substituted with 0 to 3 $C_{1-4}$ alkyl groups; pyrrolidinyl; thiazolyl substituted with 0 to 2 $C_{1-4}$ alkyl groups; 2,3-dihydroxy indole substituted with 0 to 3 $C_{1-4}$ alkyl groups;

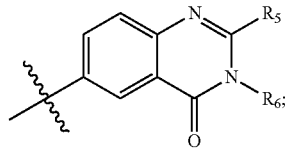

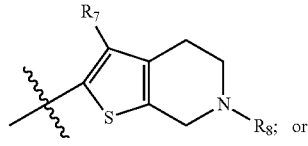

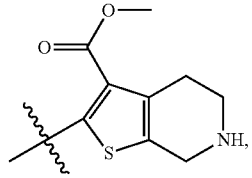

wherein $R_5$ and $R_6$ are each independently $C_{1-4}$alkyl, $C_{1-4}$alkyl sulfanyl or thiol, and $R_7$ and $R_8$ are each independently $C_{1-4}$ alkyloxycarbonyl, phenyl or benzyl.

17. A pharmaceutical composition comprising a compound represented by a following Chemical Formula I or a pharmaceutically acceptable salt thereof, and a pharmaceutically acceptable carrier:

[Chemical Formula I]

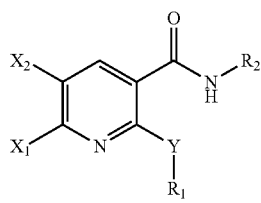

wherein,
- $X_1$ and $X_2$ are independently a halogen atom selected from the group consisting of F, Cl, Br, and I or a hydrogen atom,
- Y is —NH—; —S—; or —O—,
- $R_1$ represents piperidinyl, piperazinyl, azabicyclo[2.2.2]octanyl, or phenyl, each independently having 1 to 5 substituents selected from the group consisting of benzyl, phenyloxy, 1-pyrimidinylethyl, pyridine methyl, $C_{1-4}$ alkyl, $C_{3-6}$ alkene, t-butoxycarboxyl, and malon-2-yl; 1-azabicyclo[2.2.2]oct-3-yl; piperidin-4-yl; piperidin-3-yl; or 1-(6-chloro-5-fluoropyrimidin-4-yl)ethyl piperidin-4-yl,
  wherein the $C_{1-4}$ alkyl is substituted with 0 to 3 substituents selected from among $R_3R_4N$—, hydroxyl, and a halogen atom, wherein $R_3$ and $R_4$ are independently a $C_{1-4}$ alkyl,
  wherein the benzyl, the phenyloxy, the pyrimidinylethyl and the pyridine methyl are independently substituted with 0 to 4 halogen atoms,
- $R_2$ represents $C_{1-4}$ alkyl with 1 or 2 substituents selected from the group consisting of morpholinyl substituted with 0 to 3 benzyl groups having 0 to 3 halogen substituents, phenyl substituted with 0 to 3 halogen atoms, pyridinyl, pyrimidinyl, piperidinyl and piperazinyl; $C_{5-10}$ alkyl; $C_{1-4}$ alkyloxycarbonylamino; $C_{1-4}$alkoxy$C_{1-4}$ alkyl; toluenesulfonamino; phenyl with 0 to 3 substituents selected from among $C_{1-4}$ alkyl, halogen, nitro and phenoxy; (3,4-dimethoxy)phenyl; pyridinyl with 0 to 3 substituents selected from among $C_{1-4}$ alkyloxycarbonyl and $C_{1-4}$ alkyl; azepan-2-onyl; 1,3,4-triazolyl; pyrimidinyl substituted with 0 to 3 $C_{1-4}$ alkyl groups; pyrrolidinyl; thiazolyl substituted with 0 to 2 $C_{1-4}$ alkyl groups; 2,3-dihydroxy indole substituted with 0 to 3 $C_{1-4}$ alkyl groups;

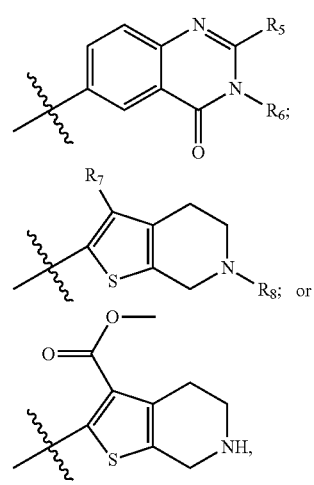

wherein $R_5$ and $R_6$ are each independently $C_{1-4}$alkyl, $C_{1-4}$alkyl sulfanyl or thiol, and
$R_7$ and $R_8$ are each independently $C_{1-4}$ alkyloxycarbonyl, phenyl or benzyl.

* * * * *